(12) United States Patent
Gucky et al.

(10) Patent No.: US 11,028,087 B2
(45) Date of Patent: Jun. 8, 2021

(54) 2,6-DISUBSTITUTED-9-CYCLOPENTYL-9H-PURINES, USE THEREOF AS MEDICAMENTS, AND PHARMACEUTICAL COMPOSITIONS

(71) Applicant: UNIVERZITA PALACKEHO V OLOMOUCI, Olomouc (CZ)

(72) Inventors: Tomas Gucky, Mladejovice (CZ); Eva Reznickova, Olomouc (CZ); Radek Jorda, Olomouc (CZ); Vladimir Krystof, Olomouc (CZ); Miroslav Strnad, Olomouc (CZ); Tereza Radosova Muchova, Vyskov (CZ); Vladimir Divoky, Olomouc (CZ)

(73) Assignee: UNIVERZITA PALACKEHO V OLOMOUCI, Olomouc (CZ)

( * ) Notice: Subject to any disclaimer, the term of this patent is extended or adjusted under 35 U.S.C. 154(b) by 0 days.

(21) Appl. No.: 16/494,650

(22) PCT Filed: Mar. 19, 2018

(86) PCT No.: PCT/CZ2018/050010
§ 371 (c)(1),
(2) Date: Sep. 16, 2019

(87) PCT Pub. No.: WO2018/171819
PCT Pub. Date: Sep. 27, 2018

(65) Prior Publication Data
US 2020/0087306 A1    Mar. 19, 2020

(30) Foreign Application Priority Data

Mar. 20, 2017    (CZ) .................................. CZ2017-157

(51) Int. Cl.
| *C07D 473/34* | (2006.01) |
| *C07D 491/10* | (2006.01) |
| *C07D 487/10* | (2006.01) |
| *A61P 35/00* | (2006.01) |

(52) U.S. Cl.
CPC ............ *C07D 473/34* (2013.01); *A61P 35/00* (2018.01); *C07D 487/10* (2013.01); *C07D 491/10* (2013.01)

(58) Field of Classification Search
CPC ... C07D 473/34; C07D 491/10; C07D 487/10
See application file for complete search history.

(56) References Cited

U.S. PATENT DOCUMENTS

2005/0187228 A1    8/2005    Haesslein

OTHER PUBLICATIONS

International Search Report and Written Opinion for corresponding PCT application No. PCT/CZ2018/050010, dated Jun. 21, 2018.

*Primary Examiner* — Laura L Stockton
(74) *Attorney, Agent, or Firm* — Nortaro, Michalos & Zaccaria P.C.

(57) ABSTRACT

The present invention relates to novel 2,6-disubstituted-9-cyclopentyl-9H-purines of general formula I, capable of inhibiting the activity of kinases such as FLT3, CDKs and PDGFRs in cancer and other related proliferative diseases. The invention further includes pharmaceutical compositions containing the 2,6-disubstituted-9-cyclopentyl-9H-purines. Compounds of the present invention can be used as active ingredients of a pharmaceutical compositions for treating acute myeloid leukemia (AML).

8 Claims, 4 Drawing Sheets

2,6-DISUBSTITUTED-9-CYCLOPENTYL-9H-PURINES, USE THEREOF AS MEDICAMENTS, AND PHARMACEUTICAL COMPOSITIONS

FIELD OF ART

The present invention relates to novel 2,6-disubstituted-9-cyclopentyl-9H-purines, capable of inhibiting the activity of kinases such as FLT3, CDKs and PDGFRs. It further relates to pharmaceutical compositions containing these compounds. The compounds and compositions may be used as medicaments to treat various diseases and conditions related to the above mentioned kinases, such as acute myeloid leukemia (AML) and other cancers.

BACKGROUND ART

AML is an oncological indication characterized by uncontrolled proliferation of myeloid hematopoietic progenitor cells within the bone marrow. It accounts for approximately 33% of all leukemia cases and is particularly common in elderly people; only 5-10% of AML patients over 60 years of age achieve long term survival (Schiffer, N Engl J Med. 2003; 349: 727-729). While younger patients' chances of survival are around 5 times higher, there is still an urgent need for safer and more efficacious AML treatments. Existing AML therapies based on classic cytotoxic chemotherapeutics (e.g. cytarabine, fludarabine, daunorubicin, topotecan) are less efficient than one would like. Recent advances in molecular cancer biology and DNA sequencing have enhanced our understanding of AML biology and led to the discovery of many cancer-related genes (Rahman, Nature. 2014; 505: 302-308). The most common mutation in AML occurs in the FLT3 gene, which encodes the membrane-bound receptor tyrosine kinase FLT3 and is closely related to KIT, FMS and PDGFR (Carow et al, Cytogen Cell Gen. 1995; 70: 255-257). Upon binding to an extracellular ligand, FLT3 dimerizes, gets autophosphorylated, and activates downstream signaling pathways including RAS/MAPK, JAK/STAT5 and PI3K/AKT. These pathways collectively promote cell growth, proliferation, survival and differentiation. FLT3 mutations are observed in approximately 30% of AML patients and are significantly linked to poor prognosis (Gilliland and Griffin; Blood. 2002; 100: 1532-1542). Less frequently, AML can express oncogenic form of receptor tyrosine kinase FIP1L1-PDGFRA, activated by translocation and fusion (Metzgeroth et al.; Leukemia. 2007; 21: 1183-8). Importantly, amplification, mutations or upregulation of PDGFR occurs also in gliomas and sarcomas (Kumabe et al., Oncogene, 1992; 7: 627-633; Ostman and Heldin, Cancer Res. 2001; 80: 1-38), chronic myelomonocytic leukemia (Magnusson et al., Blood 2002; 100: 1088-1091), lung carcinoma (Ramo et al., Cancer Biol Ther. 2009; 8: 2042-50) and gastrointestinal tumors (Heinrich et al., Science 2003; 299: 708-710).

The most common group of FLT3 mutations (found in 23% of all AML patients) are internal tandem duplications (ITD) of variable length and position that promote ligand-independent dimerization (Nakao et al.; Leukemia. 1996; 10: 1911-1918). The length of ITD mutations influences prognosis: patients with longer ITDs have worse outcomes and lower overall survival (Stirewalt et al.; Blood. 2006; 107: 3724-3726). Point mutations within the activation loop of FLT3 are also somewhat common, occurring in approximately 7% of all AML cases. These mutations stabilize the kinase in its active conformation and promote constitutive activation. FLT3 is regarded as a potential drug target because patients with FLT3-ITD mutations respond poorly to standard cytotoxic agents and there is a clear link between AML and the oncogenic properties of FLT3 (Pemmaraju et al.; Cancer. 2011; 117: 3293-304). Consequently, many groups have attempted to develop specific FLT3 inhibitors for AML therapy and a variety of drugs have entered clinical trials (Wander et al.; Ther Adv Hematol. 2014; 5: 65-77; Pemmaraju et al.; Expert Opin Investig Drugs. 2014; 23:943-954).

The toxicity problems and limited efficacy of these drugs are probably due to their broad specificity towards receptor tyrosine kinases (Pemmaraju et al.; Expert Opin Investig Drugs. 2014; 23: 943-954). Therefore, new and more specific FLT3 inhibitors have been developed. These so-called second generation compounds include quizartinib, crenolanib and PLX3397. Quizartinib, a specific nanomolar FLT3 inhibitor, induced rapid and complete regression in subcutaneous tumor xenografts of MV4-11 cells derived from an FLT3-positive AML cell line (Zarrinkar et al.; Blood. 2009; 114: 2984-2992). Moreover, quizartinib was well-tolerated in clinical experiments and demonstrated significant numbers of complete and partial responses in AML patients (Wander et al.; Ther Adv Hematol. 2014; 5:65-77). A second highly potent FLT3 inhibitor, crenolanib, also showed efficacy in clinical trials. This compound was active in quizartinib-resistant AML cells with FLT3 point mutations (Zimmerman et al.; Blood. 2013; 122: 3607-3615). Despite these promising results, acquired resistance to specific FLT3 inhibitors continues to present a major challenge in drug development. Several mechanisms that cause resistance to kinase inhibitors in AML patients with FLT3 mutations have been identified. Acquired resistance to sorafenib, midostaurin and quizartinib has been attributed to point mutations in the kinase domain (Wander et al.; Ther Adv Hematol. 2014; 5: 65-77). Such resistance may also be influenced by the upregulation of downstream cellular signaling pathways and compensatory interactions between them. Studies of these mechanisms may yield treatments with improved therapeutic outcomes that prevent the development of resistance.

The complexity and heterogeneity of AML greatly complicates the development of efficient and safe therapies. However, very promising early results have been obtained with treatments that specifically target AML cells, for example by using drugs that simultaneously inhibit FLT3 and other critical oncogenic kinase(s). Such multi-targeted anti-FLT3 drugs are already being developed for certain indications (Melisi et al.; Curr Opin Pharmacol. 2013; 13: 536-542), including AML. For example, two selective JAK2/FLT3 inhibitors, SB1578 and SB1518 (pacritinib), have recently entered clinical trials (Poulsen et al.; J Comput Aided Mol Des. 2012; 26: 437-450). While SB1578 was developed for the non-oncological indication rheumatoid arthritis, pacritinib was successful in phase 2 clinical trials against myelofibrosis and lymphoma. Another multi-kinase inhibitor, TG02 (SB1317), which targets FLT3, JAK2, and all CDKs, was selected for preclinical development and is now in phase 1 clinical trials (Goh et al.; Leukemia. 2012; 26: 236-243). AMG 925 is yet another compound with double mechanism of action; it selectively targets FLT3 and CDK4/6 (Keegan et al.; Mol Cancer Ther. 2014; 13: 880-889; Li et al.; J Med Chem. 2014; 57: 3430-3449). This compound inhibited proliferation in a panel of cancer cell lines, some of which are resistant to FLT3 inhibitors in clinical development.

Low-molecular protein kinases inhibitors with potential therapeutical use are being developed according to various strategies. However, structural and functional similarities and differences of particular kinases encounter difficulties in their development (Manning et al.; Science. 2002; 5600: 1912-34). For example, FLT3 is a protein kinase, which has a significantly different sequence, structure and function, is, due to its transmembrane domain, located in the cytoplasmic membrane (Meshinchi and Appelbaum, Clin Cancer Res 2009; 13: 4263-9), while for example CDKs mentioned in the previous paragraph are nuclear kinases and their substrates are biochemically different. FLT3 phosphorylates tyrosine residues, CDKs exclusively serine and threonine. Clinically studied CDK inhibitors do not inhibit FLT3 and vice versa, clinically studied FLT3 inhibitors do not inhibit CDK. The exceptions mentioned (eg AMG-925) have a completely different structure from the substances of the present invention (Li et al., J. Med Chem., 2014, 57: 3430-3449). The closest clinically studied CDK inhibitors are roskovitin, CR8 and dinaciclib, which do not inhibit FLT3 nor other receptor PKs (Bach et al., J Biol Chem 2005; 35: 31208-19, Bettayeb et al., Oncogene 2008; 44: 5797-807, Chen et al., Mol Cancer Ther. 2016; 10: 2273-2281).

While there are several anti-AML agents in development, none of them have shown levels of selectivity or efficacy that can be expected to dramatically change the treatment paradigm for this disease. As such there is still a large space in the market for novel drugs for AML patients. The present therefore aims to provide new anti-AML agents based on a previously unknown series of small molecules that exhibit strong cytotoxic activity and unprecedentedly high selectivity towards AML cell lines. The present invention therefore provides a series of novel 2,6-disubstituted-9-cyclopentyl-9H-purines displaying (sub)nanomolar inhibitory potency towards FLT3. The compounds are useful for treatment of AML forms, including those resistant to other therapies, and also other cancers and various other disease conditions caused by or related to deregulated protein kinases. It is the aim of this invention to provide a new generation of unique and effective antileukemic compounds having improved selectivity and efficacy.

DISCLOSURE OF THE INVENTION

The object of the present invention are 2,6-disubstituted-9-cyclopentyl-9H-purine derivatives of the general formula I.

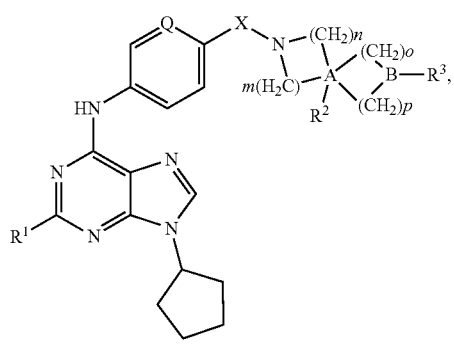

(I)

wherein $R^1$ is selected from the group consisting of

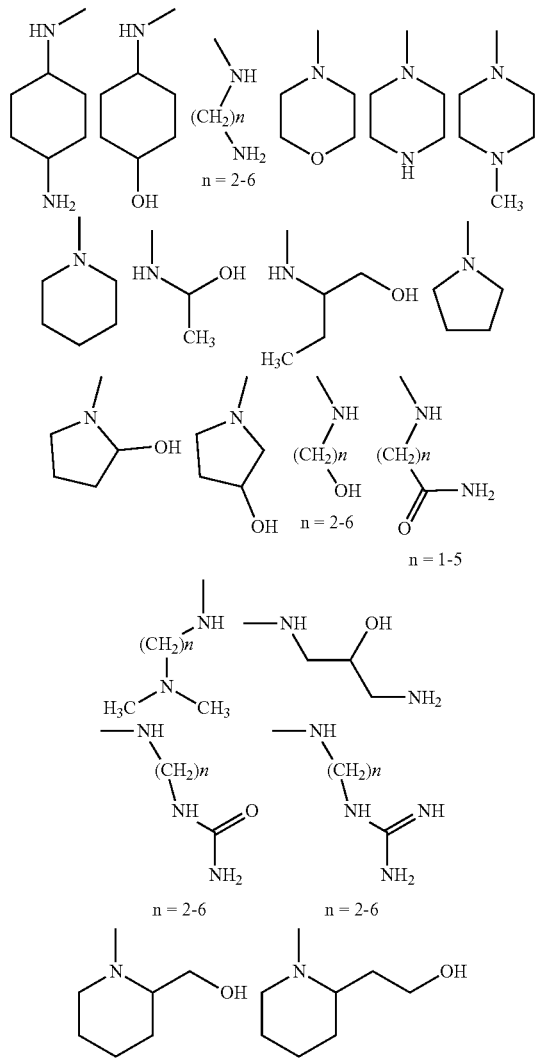

and
Q is =CH— or =N—;
X is a bond, $CH_2$, NH or C=O;
m is 1 or 2 or 3;
n is 1 or 2 or 3; preferably m is equal to n;
A is selected from the group containing O, N, CH, C; with the proviso that:
if A is 0, then o=p=0 and $R^2$, B and $R^3$ are not present,
if A is N or CH, then $R^2$ is selected from H, $CH_3$, $CH_2CH_3$, and o=p=0 and B and $R^3$ are not present,
if A is C, then $R^2$ is not represent, o is 1 or 2 or 3, p is 1 or 2 or 3, and B and $R^3$ are as defined bellow;
B is selected from O and N, with the proviso that:
if B is O, then $R^3$ is not present,
if B is N, then $R^3$ is selected from H, $CH_3$, $CH_2CH_3$;
and pharmaceutically acceptable salts thereof, in particular salts with alkali metals, ammonium or amines, or addition salts with acids.

When chiral centers are present in the molecule, the present invention encompasses optically active isomers, their mixtures and racemates.

Another object of this invention are 2,6-disubstituted-9-cyclopentyl-9H-purines, of the general formula I for use in the treatment of cancer disorders, including solid tumors, leukemia and lymphoma, and other proliferative diseases and conditions.

A further object of this invention are 2,6-disubstituted-9-cyclopentyl-9H-purines, of the general formula I for use as antileukemic compounds in the treatment of acute myeloid leukemia (AML) associated with wild type or mutant FLT3 kinase. Examples of FLT3 mutants include, but are not limited to, FLT3-ITD, FLT3 with point mutations such as FLT3-D835Y, FLT3-D835H, FLT3-D835V, FLT3-K663Q, and FLT3-N8411.

Yet another object of this invention are 2,6-disubstituted-9-cyclopentyl-9H-purines of the general formula I for use in the treatment of leukemia. The preferred types are selected from, but not limited to, acute lymphocytic leukemia, acute promyelocytic leukemia, chronic lymphocytic leukemia, chronic myeloid leukemia, chronic neutrophilic leukemia, acute undifferentiated leukemia, anaplastic large cell lymphoma, prolymphocytic leukemia, juvenile myelomonocytic leukemia, adult T cell leukemia, myelodysplastic syndrome, or myeloproliferative disorder.

Yet further object of this invention are 2,6-disubstituted-9-cyclopentyl-9H-purines of the general formula I for use in the treatment of diverse eosinophilia-associated hematologic disorders associated with deregulated PDGFRA, PDGFRB or FGFR1 kinase activity, but preferably for chronic eosinophilic leukemia, in which is PDGFRA activated by FIP1L1-PDGFRA oncogenic translocation and fusion. Preferably, the eosinophilia-associated hematologic disorders are hyperseosinophilic syndrome, lymphocyte-variant hypereosinophilia and idiopathic hypereosinophilic syndrome, acute myeloid leukemia, B-cell or T-cell acute lymphoblastic leukemia, lymphoblastic lymphoma, or myeloid sarcoma expressing FIP1L1-PDGFRA.

Another object of this invention are 2,6-disubstituted-9-cyclopentyl-9H-purines of the general formula I for use in the treatment of solid tumors with amplified, activated, deregulated or overexpressed PDGFRA, such as gliomas, sarcomas, gastrointestinal stromal tumors, non-small cell lung carcinomas and others.

Another object of this invention are 2,6-disubstituted-9-cyclopentyl-9H-purines of the general formula I for use as anti-cancer or anti-AML agents with a mode of action based on inhibition of protein kinases selected from the group comprising FLT3, CDKs 1, 2, 3, 5, 7, 9, PDGFRA or PDGFRB, or combinations thereof.

Yet another object of this invention are 2,6-disubstituted-9-cyclopentyl-9H-purines, of the general formula I to treat cancer which is selected from, but not limited to, acute lymphoblastic leukemia, breast cancer, colorectal cancer, small cell lung carcinoma, non-small cell lung carcinoma, head and neck, glioblastoma, pancreatic, gastrointestinal, liver, prostate, ovarian, testicular, endometrial, or bladder cancer, melanoma, osteosarcoma, or another sarcoma.

The invention also includes the use of the compound of general formula I in combination with at least one further therapeutic agent such as a cytotoxic agent or a compound that inhibits another kinase. The at least one further therapeutic agent is selected from cytosine arabinoside, daunorubicin, doxorubicin, cyclophosphamide, etoposide, carboplatin, fludarabine, mitoxantrone, dexamethasone, rituximab, midostaurin, a granulocyte colony-stimulating factor, decitabine, azacitidine, paclitaxel, gemcitibine, motesanib, panitumumab, PI3K, AKT, mTOR, MEK, ERK, JAK or aurora kinase inhibitors.

The invention also includes a pharmaceutical composition comprising at least one 2,6-disubstituted-9-cyclopentyl-9H-purines, of the general formula I, and a pharmaceutically acceptable carrier, and optionally another anticancer agent selected from the group of cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, decitabine, azacitidine, paclitaxel, gemcitibine, motesanib, panitumumab, PI3K, AKT, mTOR, MEK, ERK, JAK or aurora kinase inhibitors.

In one embodiment, the entity of general formula II

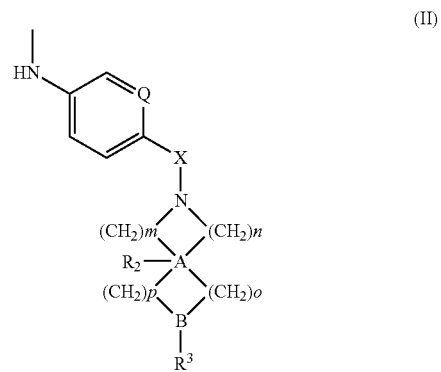

is selected from the group consisting of:
4-morpholin-4-ylcarbonyl-phenylamino, 4-piperazin-1-ylcarbonyl-phenylamino, 4-(4-methyl-piperazin-1-ylcarbonyl)-phenylamino, 4-(4-ethyl-piperazin-1-ylcarbonyl)-phenylamino, 4-(2-oxa-6-aza-spiro[3.3]hept-6-ylcarbonyl)-phenylamino, 4-(2,6-diaza-spiro[3.3]hept-2-ylcarbonyl)-phenylamino, 4-(6-methyl-2,6-diaza-spiro[3.3]hept-2-ylcarbonyl)-phenylamino, 4-(6-ethyl-2,6-diaza-spiro[3.3]hept-2-ylcarbonyl)-phenylamino.

In one embodiment, the entity of general formula II is selected from the group consisting of: 4-morpholin-4-ylmethyl-phenylamino, 4-piperazin-1-ylmethyl-phenylamino, 4-(4-methyl-piperazin-1-ylmethyl)-phenylamino, 4-(4-ethyl-piperazin-1-ylmethyl)-phenylamino, 4-(2-oxa-6-aza-spiro[3.3]hept-6-ylmethyl)-phenylamino, 4-(2,6-diaza-spiro[3.3]hept-2-ylmethyl)-phenylamino, 4-(6-methyl-2,6-diaza-spiro[3.3]hept-2-ylmethyl)-phenylamino, 4-(6-ethyl-2,6-diaza-spiro[3.3]hept-2-ylmethyl)-phenylamino.

In one embodiment, the entity of general formula II is selected from the group consisting of: 4-morpholin-4-ylcarbonyl-phenylamino, 4-piperazin-1-ylcarbonyl-phenylamino, 4-(4-methyl-piperazin-1-ylcarbonyl)-phenylamino, 4-(4-ethyl-piperazin-1-ylcarbonyl)-phenylamino, 4-(2-oxa-6-aza-spiro[3.3]hept-6-ylcarbonyl)-phenylamino, 4-(2,6-diaza-spiro[3.3]hept-2-ylcarbonyl)-phenylamino, 4-(6-methyl-2,6-diaza-spiro[3.3]hept-2-ylcarbonyl)-phenylamino, 4-(6-ethyl-2,6-diaza-spiro[3.3]hept-2-ylcarbonyl)-phenylamino.

In yet another embodiment, the entity of the general formula II is selected from the group consisting of:
6-morpholin-4-yl-pyridin-3-ylamino, 6-piperazin-1-yl-pyridin-3-ylamino, 6-(4-methyl-piperazin-1-yl)-pyridin-3-ylamino, 6-(4-ethyl-piperazin-1-yl)-pyridin-3-ylamino, 6-(2-oxa-6-aza-spiro[3.3]hept-6-yl)-pyridin-3-ylamino, 6-(2,6-diaza-spiro[3.3]hept-2-yl)-pyridin-3-ylamino, 6-(6-methyl-2,6-diaza-spiro[3.3]hept-2-yl)-pyridin-3-ylamino, 6-(6-ethyl-2,6-diaza-spiro[3.3]hept-2-yl)-pyridin-3-ylamino, 6-pyrrolidin-1-yl-pyridin-3-ylamino.

In yet another preferred embodiment, the entity of general formula II is selected from the group consisting of: 6-morpholin-4-ylmethyl-pyridin-3-ylamino, 6-piperazin-1-ylmethyl-pyridin-3-ylamino, 6-(4-methyl-piperazin-1-ylmethyl)-pyridin-3-ylamino, 6-(4-ethyl-piperazin-1-ylmethyl)-pyridin-3-ylamino, 6-(2-oxa-6-aza-spiro[3.3]hept-6-ylmethyl)-pyridin-3-ylamino, 6-(2,6-diaza-spiro[3.3]hept-2-ylmethyl)-pyridin-3-ylamino, 6-(6-methyl-2,6-diaza-spiro[3.3]hept-2-ylmethyl)-pyridin-3-ylamino, 6-(6-ethyl-2,6-diaza-spiro[3.3]hept-2-ylmethyl)-pyridin-3-ylamino.

In yet another preferred embodiment, the entity of general formula II is selected from the group consisting of: 6-morpholin-4-ylcarbonyl-pyridin-2-ylamino, 6-piperazin-1-ylcarbonyl-pyridin-2-ylamino, 6-(4-methyl-piperazin-1-ylcarbonyl)-pyridin-2-ylamino, 6-(4-ethyl-piperazin-1-ylcarbonyl)-pyridin-2-ylamino, 6-(2-oxa-6-aza-spiro[3.3]hept-6-ylcarbonyl)-pyridin-2-ylamino, 6-(2,6-diaza-spiro[3.3]hept-2-ylcarbonyl)-pyridin-2-ylamino, 6-(6-methyl-2,6-diaza-spiro[3.3]hept-2-ylcarbonyl)-pyridin-2-ylamino, 6-(6-ethyl-2,6-diaza-spiro[3.3]hept-2-ylcarbonyl)-pyridin-2-ylamino.

In one embodiment is $R^1$ 4-amino-cyclohexylamino, Q is CH, X is a bond or $CH_2$, m=2, n=2, A is O or N, $R^2$ is not present or $R^2$ is H, $CH_3$, $CH_2CH_3$.

In one embodiment is $R^1$ 4-amino-cyclohexylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-amino-cyclohexylamino, Q is CH, X is C=O, m=2, n=2, A is O or N, $R^2$ is not present or $R^2$ is H, $CH_3$, $CH_2CH_3$.

In one embodiment is $R^1$ 4-amino-cyclohexylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 4-amino-cyclohexylamino, Q is N, X is a bond or $CH_2$, m=2, n=2, A is O or N, $R^2$ is not present or $R^2$ is H, $CH_3$, $CH_2CH_3$.

In one embodiment is $R^1$ 4-amino-cyclohexylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-amino-cyclohexylamino, Q is N, X is C=O, m=2, n=2, A is O or N, $R^2$ is not present or $R^2$ is H, $CH_3$, $CH_2CH_3$.

In one embodiment is $R^1$ 4-amino-cyclohexylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 4-hydroxy-cyclohexylamino, Q is CH, X is a bond or $CH_2$, m=2, n=2, A is O nebo N, $R^2$ is not present or $R^2$ is H, $CH_3$, $CH_2CH_3$.

In one embodiment is $R^1$ 4-hydroxy-cyclohexylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-hydroxy-cyclohexylamino, Q is CH, X is C=O, m=2, n=2, A is O or N, $R^2$ is not present or $R^2$ is H, $CH_3$, $CH_2CH_3$.

In one embodiment is $R^1$ 4-hydroxy-cyclohexylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 4-hydroxy-cyclohexylamino, Q is N, X is a bond or $CH_2$, m=2, n=2, A is O or N, $R^2$ is not present or $R^2$ is H, $CH_3$, $CH_2CH_3$.

In one embodiment is $R^1$ 4-hydroxy-cyclohexylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-hydroxy-cyclohexylamino, Q is N, X is C=O, m=2, n=2, A is O or N, $R^2$ is not present or $R^2$ is H, $CH_3$, $CH_2CH_3$.

In one embodiment is $R^1$ 4-hydroxy-cyclohexylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 2-aminoethylamino, Q is CH, X is a bond or $CH_2$, m=2, n=2, A is O or N, $R^2$ is not present or $R^2$ is H, $CH_3$, $CH_2CH_3$.

In one embodiment is $R^1$ 2-aminoethylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 2-aminoethylamino, Q is CH, X is C=O, m=2, n=2, A is O or N, $R^2$ is not present or $R^2$ is H, $CH_3$, $CH_2CH_3$.

In one embodiment is $R^1$ 2-aminoethylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 2-aminoethylamino, Q is N, X is a bond or $CH_2$, m=2, n=2, A is O or N, $R^2$ is not present or $R^2$ is H, $CH_3$, $CH_2CH_3$.

In one embodiment is $R^1$ 2-aminoethylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 2-aminoethylamino, Q is N, X is C=O, m=2, n=2, A is O or N, $R^2$ is not present or $R^2$ is H, $CH_3$, $CH_2CH_3$.

In one embodiment is $R^1$ 2-aminoethylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 3-aminopropylamino, Q is CH, X is a bond or $CH_2$, m=2, n=2, A is O or N, $R^2$ is not present or $R^2$ is H, $CH_3$, $CH_2CH_3$.

In one embodiment is $R^1$ 3-aminopropylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 3-aminopropylamino, Q is CH, X is C=O, m=2, n=2, A is O or N, $R^2$ is not present or $R^2$ is H, $CH_3$, $CH_2CH_3$.

In one embodiment is $R^1$ 3-aminopropylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 3-aminopropylamino, Q is N, X is a bond or $CH_2$, m=2, n=2, A is O or N, $R^2$ is not present or $R^2$ is H, $CH_3$, $CH_2CH_3$.

In one embodiment is $R^1$ 3-aminopropylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 3-aminopropylamino, Q is N, X is C=O, m=2, n=2, A is O or N, $R^2$ is not present or $R^2$ is H, $CH_3$, $CH_2CH_3$.

In one embodiment is $R^1$ 3-aminopropylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 4-aminobutylamino, Q is CH, X is a bond or $CH_2$, m=2, n=2, A is O or N, $R^2$ is not present or $R^2$ is H, $CH_3$, $CH_2CH_3$.

In one embodiment is $R^1$ 4-aminobutylamino, Q is CH, X is binding or $CH_2$, A is C, m=1, n=1, o=1, p=1, B is O or N, $R^3$ is not present or $R^3$ is H, $CH_3$, $CH_2CH_3$.

In one embodiment is $R^1$ 4-aminobutylamino, Q is CH, X is C=O, m=2, n=2, A is O or N, $R^2$ is not present or $R^2$ is H, $CH_3$, $CH_2CH_3$.

In one embodiment is $R^1$ 4-aminobutylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 4-aminobutylamino, Q is N, X is a bond or $CH_2$, m=2, n=2, A is O or N, $R^2$ is not present or $R^2$ is H, $CH_3$, $CH_2CH_3$.

In one embodiment is $R^1$ 4-aminobutylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-aminobutylamino, Q is N, X is C=O, m=2, n=2, A is O or N, $R^2$ is not present or $R^2$ is H, $CH_3$, $CH_2CH_3$.

In one embodiment is $R^1$ 4-aminobutylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 5-aminopentylamino, Q is CH, X is a bond or $CH_2$, m=2, n=2, A is O or N, $R^2$ is not present or $R^2$ is H, $CH_3$, $CH_2CH_3$.

In one embodiment is $R^1$ 5-aminopentylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 5-aminopentylamino, Q is CH, X is C=O, m=2, n=2, A is O or N, $R^2$ is not present or $R^2$ is H, $CH_3$, $CH_2CH_3$.

In one embodiment is $R^1$ 5-aminopentylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 5-aminopentylamino, Q is N, X is a bond or $CH_2$, m=2, n=2, A is O or N, $R^2$ is not present or $R^2$ is H, $CH_3$, $CH_2CH_3$.

In one embodiment is $R^1$ 5-aminopentylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 5-aminopentylamino, Q is N, X is C=O, m=2, n=2, A is O or N, $R^2$ is not present or $R^2$ is H, $CH_3$, $CH_2CH_3$.

In one embodiment is $R^1$ 5-aminopentylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 6-aminohexylamino, Q is CH, X is a bond or $CH_2$, m=2, n=2, A is O or N, $R^2$ is not present or $R^2$ is H, $CH_3$, $CH_2CH_3$.

In one embodiment is $R^1$ 6-aminohexylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 6-aminohexylamino, Q is CH, X is C=O, m=2, n=2, A is O or N, $R^2$ is not present or $R^2$ is H, $CH_3$, $CH_2CH_3$.

In one embodiment is $R^1$ 6-aminohexylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 6-aminohexylamino, Q is N, X is a bond or $CH_2$, m=2, n=2, A is O or N, $R^2$ is not present or $R^2$ is H, $CH_3$, $CH_2CH_3$.

In one embodiment is $R^1$ 6-aminohexylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 6-aminohexylamino, Q is N, X is C=O, m=2, n=2, A is O or N, $R^2$ is not present or $R^2$ is H, $CH_3$, $CH_2CH_3$.

In one embodiment is $R^1$ 6-aminohexylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ morpholin-4-ylamino, Q is CH, X is a bond or $CH_2$, m=2, n=2, A is O or N, $R^2$ is not present or $R^2$ is H, $CH_3$, $CH_2CH_3$.

In one embodiment is $R^1$ morpholin-4-ylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ morpholin-4-ylamino, Q is CH, X is C=O, m=2, n=2, A is O or N, $R^2$ is not present or $R^2$ is H, $CH_3$, $CH_2CH_3$.

In one embodiment is $R^1$ morpholin-4-ylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ morpholin-4-ylamino, Q is N, X is a bond or $CH_2$, m=2, n=2, A is O or N, $R^2$ is not present or $R^2$ is H, $CH_3$, $CH_2CH_3$.

In one embodiment is $R^1$ morpholin-4-ylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ morpholin-4-ylamino, Q is N, X is C=O, m=2, n=2, A is O or N, $R^2$ is not present or $R^2$ is H, $CH_3$, $CH_2CH_3$.

In one embodiment is $R^1$ morpholin-4-ylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ piperazin-1-ylamino, Q is CH, X is a bond or $CH_2$, m=2, n=2, A is O or N, $R^2$ is not present or $R^2$ is H, $CH_3$, $CH_2CH_3$.

In one embodiment is $R^1$ piperazin-1-ylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ piperazin-1-ylamino, Q is CH, X is C=O, m=2, n=2, A is O or N, $R^2$ is not present or $R^2$ is H, $CH_3$, $CH_2CH_3$.

In one embodiment is $R^1$ piperazin-1-ylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ piperazin-1-ylamino, Q is N, X is a bond or $CH_2$, m=2, n=2, A is O or N, $R^2$ is not present or $R^2$ is H, $CH_3$, $CH_2CH_3$.

In one embodiment is $R^1$ piperazin-1-ylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ piperazin-1-ylamino, Q is N, X is C=O, m=2, n=2, A is O or N, $R^2$ is not present or $R^2$ is H, $CH_3$, $CH_2CH_3$.

In one embodiment is $R^1$ piperazin-1-ylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 4-methylpiperazin-1-ylamino, Q is CH, X is a bond or $CH_2$, m=2, n=2, A is O or N, $R^2$ is not present or $R^2$ is H, $CH_3$, $CH_2CH_3$.

In one embodiment is $R^1$ 4-methylpiperazin-1-ylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-methylpiperazin-1-ylamino, Q is CH, X is C=O, m=2, n=2, A is O or N, $R^2$ is not present or $R^2$ is H, $CH_3$, $CH_2CH_3$.

In one embodiment is $R^1$ 4-methylpiperazin-1-ylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 4-methylpiperazin-1-ylamino, Q is N, X is a bond or $CH_2$, m=2, n=2, A is O or N, $R^2$ is not present or $R^2$ is H, $CH_3$, $CH_2CH_3$.

In one embodiment is $R^1$ 4-methylpiperazin-1-ylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-methylpiperazin-1-ylamino, Q is N, X is C=O, m=2, n=2, A is O or N, $R^2$ is not present or $R^2$ is H, $CH_3$, $CH_2CH_3$.

In one embodiment is $R^1$ 4-methylpiperazin-1-ylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ piperidin-1-ylamino, Q is CH, X is a bond or $CH_2$, m=2, n=2, A is O or N, $R^2$ is not present or $R^2$ is H, $CH_3$, $CH_2CH_3$.

In one embodiment is $R^1$ piperidin-1-ylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ piperidin-1-ylamino, Q is CH, X is C=O, m=2, n=2, A is O or N, $R^2$ is not present or $R^2$ is H, CH$_3$, CH$_2$CH$_3$.

In one embodiment is $R^1$ piperidin-1-ylamino, Q is CH, X is C=O, A is C, m=1, n=1, o=1, p=1, B is O or N, $R^3$ is not present or $R^3$ is H, CH$_3$, CH$_2$CH$_3$.

In one embodiment is $R^1$ piperidin-1-ylamino, Q is N, X is a bond or CH$_2$, m=2, n=2, A is O or N, $R^2$ is not present or $R^2$ is H, CH$_3$, CH$_2$CH$_3$.

In one embodiment is $R^1$ piperidin-1-ylamino, Q is N, X is a bond or CH$_2$, A is C, m=1, n=1, o=1, p=1, B is O or N, $R^3$ is not present or $R^3$ is H, CH$_3$, CH$_2$CH$_3$.

In one embodiment is $R^1$ piperidin-1-ylamino, Q is N, X is C=O, m=2, n=2, A is O or N, $R^2$ is not present or $R^2$ is H, CH$_3$, CH$_2$CH$_3$.

In one embodiment is $R^1$ piperidin-1-ylamino, Q is N, X is C=O, A is C, m=1, n=1, o=1, p=1, B is O or N, $R^3$ is not present or $R^3$ is H, CH$_3$, CH$_2$CH$_3$.

In one embodiment is $R^1$ pyrrolidin-1-ylamino, Q is CH, X is a bond or CH$_2$, m=2, n=2, A is O or N, $R^2$ is not present or $R^2$ is H, CH$_3$, CH$_2$CH$_3$.

In one embodiment is $R^1$ pyrrolidin-1-ylamino, Q is CH, X is a bond or CH$_2$, A is C, m=1, n=1, o=1, p=1, B is O or N, $R^3$ is not present or $R^3$ is H, CH$_3$, CH$_2$CH$_3$.

In one embodiment is $R^1$ pyrrolidin-1-ylamino, Q is CH, X is C=O, m=2, n=2, A is O or N, $R^2$ is not present or $R^2$ is H, CH$_3$, CH$_2$CH$_3$.

In one embodiment is $R^1$ pyrrolidin-1-ylamino, Q is CH, X is C=O, A is C, m=1, n=1, o=1, p=1, B is O or N, $R^3$ is not present or $R^3$ is H, CH$_3$, CH$_2$CH$_3$.

In one embodiment is $R^1$ pyrrolidin-1-ylamino, Q is N, X is a bond or CH$_2$, m=2, n=2, A is O or N, $R^2$ is not present or $R^2$ is H, CH$_3$, CH$_2$CH$_3$.

In one embodiment is $R^1$ pyrrolidin-1-ylamino, Q is N, X is a bond or CH$_2$, A is C, m=1, n=1, o=1, p=1, B is O or N, $R^3$ is not present or $R^3$ is H, CH$_3$, CH$_2$CH$_3$.

In one embodiment is $R^1$ pyrrolidin-1-ylamino, Q is N, X is C=O, m=2, n=2, A is O or N, $R^2$ is not present or $R^2$ is H, CH$_3$, CH$_2$CH$_3$.

In one embodiment is $R^1$ pyrrolidin-1-ylamino, Q is N, X is C=O, A is C, m=1, n=1, o=1, p=1, B is O or N, $R^3$ is not present or $R^3$ is H, CH$_3$, CH$_2$CH$_3$.

In one embodiment is $R^1$ 2-hydroxy-cyclopentylamino, 3-hydroxy-cyclopentylamino, Q is CH, X is a bond or CH$_2$, m=2, n=2, A is O or N, $R^2$ is not present or $R^2$ is H, CH$_3$, CH$_2$CH$_3$.

In one embodiment is $R^1$ 2-hydroxy-cyclopentylamino, 3-hydroxy-cyclopentylamino, Q is CH, X is a bond or CH$_2$, A is C, m=1, n=1, o=1, p=1, B is O or N, $R^3$ is not present or $R^3$ is H, CH$_3$, CH$_2$CH$_3$.

In one embodiment is $R^1$ 2-hydroxy-cyclopentylamino, 3-hydroxy-cyclopentylamino, Q is CH, X is C=O, m=2, n=2, A is O or N, $R^2$ is not present or $R^2$ is H, CH$_3$, CH$_2$CH$_3$.

In one embodiment is $R^1$ 2-hydroxy-cyclopentylamino, 3-hydroxy-cyclopentylamino, Q is CH, X is C=O, A is C, m=1, n=1, o=1, p=1, B is O or N, $R^3$ is not present or $R^3$ is H, CH$_3$, CH$_2$CH$_3$.

In one embodiment is $R^1$ 2-hydroxy-cyclopentylamino, 3-hydroxy-cyclopentylamino, Q is N, X is a bond or CH$_2$, m=2, n=2, A is O or N, $R^2$ is not present or $R^2$ is H, CH$_3$, CH$_2$CH$_3$.

In one embodiment is $R^1$ 2-hydroxy-cyclopentylamino, 3-hydroxy-cyclopentylamino, Q is N, X is a bond or CH$_2$, A is C, m=1, n=1, o=1, p=1, B is O or N, $R^3$ is not present or $R^3$ is H, CH$_3$, CH$_2$CH$_3$.

In one embodiment is $R^1$ 2-hydroxy-cyclopentylamino, 3-hydroxy-cyclopentylamino, Q is N, X is C=O, m=2, n=2, A is O or N, $R^2$ is not present or $R^2$ is H, CH$_3$, CH$_2$CH$_3$.

In one embodiment is $R^1$ 2-hydroxy-cyclopentylamino, 3-hydroxy-cyclopentylamino, Q is N, X is C=O, A is C, m=1, n=1, o=1, p=1, B is O or N, $R^3$ is not present or $R^3$ is H, CH$_3$, CH$_2$CH$_3$.

In one embodiment is $R^1$ 2-hydroxymethyl-piperidin-1-yl, Q is CH, X is a bond or CH$_2$, m=2, n=2, A is O or N, $R^2$ is not present or $R^2$ is H, CH$_3$, CH$_2$CH$_3$.

In one embodiment is $R^1$ 2-hydroxymethyl-piperidin-1-yl, Q is CH, X is a bond or CH$_2$, A is C, m=1, n=1, o=1, p=1, B is O or N, $R^3$ is not present or $R^3$ is H, CH$_3$, CH$_2$CH$_3$.

In one embodiment is $R^1$ 2-hydroxymethyl-piperidin-1-yl, Q is CH, X is C=O, m=2, n=2, A is O or N, $R^2$ is not present or $R^2$ is H, CH$_3$, CH$_2$CH$_3$.

In one embodiment is $R^1$ 2-hydroxymethyl-piperidin-1-yl, Q is CH, X is C=O, A is C, m=1, n=1, o=1, p=1, B is O or N, $R^3$ is not present or $R^3$ is H, CH$_3$, CH$_2$CH$_3$.

In one embodiment is $R^1$ 2-hydroxymethyl-piperidin-1-yl, Q is N, X is a bond or CH$_2$, m=2, n=2, A is O or N, $R^2$ is not present or $R^2$ is H, CH$_3$, CH$_2$CH$_3$.

In one embodiment is $R^1$ 2-hydroxymethyl-piperidin-1-yl, Q is N, X is a bond or CH$_2$, A is C, m=1, n=1, o=1, p=1, B is O or N, $R^3$ is not present or $R^3$ is H, CH$_3$, CH$_2$CH$_3$.

In one embodiment is $R^1$ 2-hydroxymethyl-piperidin-1-yl, Q is N, X is C=O, m=2, n=2, A is O or N, $R^2$ is not present or $R^2$ is H, CH$_3$, CH$_2$CH$_3$.

In one embodiment is $R^1$ 2-hydroxymethyl-piperidin-1-yl, Q is N, X is C=O, A is C, m=1, n=1, o=1, p=1, B is O or N, $R^3$ is not present or $R^3$ is H, CH$_3$, CH$_2$CH$_3$.

In one embodiment is $R^1$ 2-hydroxyethyl-piperidin-1-yl, Q is CH, X is a bond or CH$_2$, m=2, n=2, A is O or N, $R^2$ is not present or $R^2$ is H, CH$_3$, CH$_2$CH$_3$.

In one embodiment is $R^1$ 2-hydroxyethyl-piperidin-1-yl, Q is CH, X is a bond or CH$_2$, A is C, m=1, n=1, o=1, p=1, B is O or N, $R^3$ is not present or $R^3$ is H, CH$_3$, CH$_2$CH$_3$.

In one embodiment is $R^1$ 2-hydroxyethyl-piperidin-1-yl, Q is CH, X is C=O, m=2, n=2, A is O or N, $R^2$ is not present or $R^2$ is H, CH$_3$, CH$_2$CH$_3$.

In one embodiment is $R^1$ 2-hydroxyethyl-piperidin-1-yl, Q is CH, X is C=O, A is C, m=1, n=1, o=1, p=1, B is O or N, $R^3$ is not present or $R^3$ is H, CH$_3$, CH$_2$CH$_3$.

In one embodiment is $R^1$ 2-hydroxyethyl-piperidin-1-yl, Q is N, X is a bond or CH$_2$, m=2, n=2, A is O or N, $R^2$ is not present or $R^2$ is H, CH$_3$, CH$_2$CH$_3$.

In one embodiment is $R^1$ 2-hydroxyethyl-piperidin-1-yl, Q is N, X is a bond or CH$_2$, A is C, m=1, n=1, o=1, p=1, B is O or N, $R^3$ is not present or $R^3$ is H, CH$_3$, CH$_2$CH$_3$.

In one embodiment is $R^1$ 2-hydroxyethyl-piperidin-1-yl, Q is N, X is C=O, m=2, n=2, A is O or N, $R^2$ is not present or $R^2$ is H, CH$_3$, CH$_2$CH$_3$.

In one embodiment is $R^1$ 2-hydroxyethyl-piperidin-1-yl, Q is N, X is C=O, A is C, m=1, n=1, o=1, p=1, B is O or N, $R^3$ is not present or $R^3$ is H, CH$_3$, CH$_2$CH$_3$.

In one embodiment is $R^1$ 2-hydroxy-ethylamino, Q is CH, X is a bond or CH$_2$, m=2, n=2, A is O or N, $R^2$ is not present or $R^2$ is H, CH$_3$, CH$_2$CH$_3$.

In one embodiment is $R^1$ 2-hydroxy-ethylamino, Q is CH, X is a bond or CH$_2$, A is C, m=1, n=1, o=1, p=1, B is O or N, $R^3$ is not present or $R^3$ is H, CH$_3$, CH$_2$CH$_3$.

In one embodiment is $R^1$ 2-hydroxy-ethylamino, Q is CH, X is C=O, m=2, n=2, A is O or N, $R^2$ is not present or $R^2$ is H, CH$_3$, CH$_2$CH$_3$.

In one embodiment is $R^1$ 2-hydroxy-ethylamino, Q is CH, X is C=O, A is C, m=1, n=1, o=1, p=1, B is O or N, $R^3$ is not present or $R^3$ is H, CH$_3$, CH$_2$CH$_3$.

In one embodiment is $R^1$ 2-hydroxy-ethylamino, Q is N, X is a bond or $CH_2$, m=2, n=2, A is O or N, $R^2$ is not present or $R^2$ is H, $CH_3$, $CH_2CH_3$.

In one embodiment is $R^1$ 2-hydroxy-ethylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 2-hydroxy-ethylamino, Q is N, X is C=O, m=2, n=2, A is O or N, $R^2$ is not present or $R^2$ is H, $CH_3$, $CH_2CH_3$.

In one embodiment is $R^1$ 2-hydroxy-ethylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 3-hydroxy-propylamino, Q is CH, X is a bond or $CH_2$, m=2, n=2, A is O or N, $R^2$ is not present or $R^2$ is H, $CH_3$, $CH_2CH_3$.

In one embodiment is $R^1$ 3-hydroxy-propylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 3-hydroxy-propylamino, Q is CH, X is C=O, m=2, n=2, A is O or N, $R^2$ is not present or $R^2$ is H, $CH_3$, $CH_2CH_3$.

In one embodiment is $R^1$ 3-hydroxy-propylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 3-hydroxy-propylamino, Q is N, X is a bond or $CH_2$, m=2, n=2, A is O or N, $R^2$ is not present or $R^2$ is H, $CH_3$, $CH_2CH_3$.

In one embodiment is $R^1$ 3-hydroxy-propylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 3-hydroxy-propylamino, Q is N, X is C=O, m=2, n=2, A is O or N, $R^2$ is not present or $R^2$ is H, $CH_3$, $CH_2CH_3$.

In one embodiment is $R^1$ 3-hydroxy-propylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 4-hydroxy-butylamino, Q is CH, X is a bond or $CH_2$, m=2, n=2, A is O or N, $R^2$ is not present or $R^2$ is H, $CH_3$, $CH_2CH_3$.

In one embodiment is $R^1$ 4-hydroxy-butylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-hydroxy-butylamino, Q is CH, X is C=O, m=2, n=2, A is O or N, $R^2$ is not present or $R^2$ is H, $CH_3$, $CH_2CH_3$.

In one embodiment is $R^1$ 4-hydroxy-butylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 4-hydroxy-butylamino, Q is N, X is a bond or $CH_2$, m=2, n=2, A is O or N, $R^2$ is not present or $R^2$ is H, $CH_3$, $CH_2CH_3$.

In one embodiment is $R^1$ 4-hydroxy-butylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-hydroxy-butylamino, Q is N, X is C=O, m=2, n=2, A is O or N, $R^2$ is not present or $R^2$ is H, $CH_3$, $CH_2CH_3$.

In one embodiment is $R^1$ 4-hydroxy-butylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 5-hydroxy-pentylamino, Q is CH, X is a bond or $CH_2$, m=2, n=2, A is O or N, $R^2$ is not present or $R^2$ is H, $CH_3$, $CH_2CH_3$.

In one embodiment is $R^1$ 5-hydroxy-pentylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 5-hydroxy-pentylamino, Q is CH, X is C=O, m=2, n=2, A is O or N, $R^2$ is not present or $R^2$ is H, $CH_3$, $CH_2CH_3$.

In one embodiment is $R^1$ 5-hydroxy-pentylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 5-hydroxy-pentylamino, Q is N, X is a bond or $CH_2$, m=2, n=2, A is O or N, $R^2$ is not present or $R^2$ is H, $CH_3$, $CH_2CH_3$.

In one embodiment is $R^1$ 5-hydroxy-pentylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 5-hydroxy-pentylamino, Q is N, X is C=O, m=2, n=2, A is O or N, $R^2$ is not present or $R^2$ is H, $CH_3$, $CH_2CH_3$.

In one embodiment is $R^1$ 5-hydroxy-pentylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 6-hydroxy-hexylamino, Q is CH, X is a bond or $CH_2$, m=2, n=2, A is O or N, $R^2$ is not present or $R^2$ is H, $CH_3$, $CH_2CH_3$.

In one embodiment is $R^1$ 6-hydroxy-hexylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 6-hydroxy-hexylamino, Q is CH, X is C=O, m=2, n=2, A is O or N, $R^2$ is not present or $R^2$ is H, $CH_3$, $CH_2CH_3$.

In one embodiment is $R^1$ 6-hydroxy-hexylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 6-hydroxy-hexylamino, Q is N, X is a bond or $CH_2$, m=2, n=2, A is O or N, $R^2$ is not present or $R^2$ is H, $CH_3$, $CH_2CH_3$.

In one embodiment is $R^1$ 6-hydroxy-hexylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 6-hydroxy-hexylamino, Q is N, X is C=O, m=2, n=2, A is O or N, $R^2$ is not present or $R^2$ is H, $CH_3$, $CH_2CH_3$.

In one embodiment is $R^1$ 6-hydroxy-hexylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ aminocarbonylmethylamino, Q is CH, X is a bond or $CH_2$, m=2, n=2, A is O or N, $R^2$ is not present or $R^2$ is H, $CH_3$, $CH_2CH_3$.

In one embodiment is $R^1$ aminocarbonylmethylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ aminocarbonylmethylamino, Q is CH, X is C=O, m=2, n=2, A is O or N, $R^2$ is not present or $R^2$ is H, $CH_3$, $CH_2CH_3$.

In one embodiment is $R^1$ aminocarbonylmethylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ aminocarbonylmethylamino, Q is N, X is a bond or $CH_2$, m=2, n=2, A is O or N, $R^2$ is not present or $R^2$ is H, $CH_3$, $CH_2CH_3$.

In one embodiment is $R^1$ aminocarbonylmethylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ aminocarbonylmethylamino, Q is N, X is C=O, m=2, n=2, A is O or N, $R^2$ is not present or $R^2$ is H, $CH_3$, $CH_2CH_3$.

In one embodiment is $R^1$ aminocarbonylmethylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ aminocarbonylethylamino, Q is CH, X is a bond or $CH_2$, m=2, n=2, A is O or N, $R^2$ is not present or $R^2$ is H, $CH_3$, $CH_2CH_3$.

In one embodiment is $R^1$ aminocarbonylethylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ aminocarbonylethylamino, Q is CH, X is C=O, m=2, n=2, A is O or N, $R^2$ is not present or $R^2$ is H, $CH_3$, $CH_2CH_3$.

In one embodiment is $R^1$ aminocarbonylethylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ aminocarbonylethylamino, Q is N, X is a bond or $CH_2$, m=2, n=2, A is O or N, $R^2$ is not present or $R^2$ is H, $CH_3$, $CH_2CH_3$.

In one embodiment is $R^1$ aminocarbonylethylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ aminocarbonylethylamino, Q is N, X is C=O, m=2, n=2, A is O or N, $R^2$ is not present or $R^2$ is H, $CH_3$, $CH_2CH_3$.

In one embodiment is $R^1$ aminocarbonylethylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ aminocarbonylpropylamino, Q is CH, X is a bond or $CH_2$, m=2, n=2, A is O or N, $R^2$ is not present or $R^2$ is H, $CH_3$, $CH_2CH_3$.

In one embodiment is $R^1$ aminocarbonylpropylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ aminocarbonylpropylamino, Q is CH, X is C=O, m=2, n=2, A is O or N, $R^2$ is not present or $R^2$ is H, $CH_3$, $CH_2CH_3$.

In one embodiment is $R^1$ aminocarbonylpropylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ aminocarbonylpropylamino, Q is N, X is a bond or $CH_2$, m=2, n=2, A is O or N, $R^2$ is not present or $R^2$ is H, $CH_3$, $CH_2CH_3$.

In one embodiment is $R^1$ aminocarbonylpropylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ aminocarbonylpropylamino, Q is N, X is C=O, m=2, n=2, A is O or N, $R^2$ is not present or $R^2$ is H, $CH_3$, $CH_2CH_3$.

In one embodiment is $R^1$ aminocarbonylpropylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ aminocarbonylbutylamino, Q is CH, X is a bond or $CH_2$, m=2, n=2, A is O or N, $R^2$ is not present or $R^2$ is H, $CH_3$, $CH_2CH_3$.

In one embodiment is $R^1$ aminocarbonylbutylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ aminocarbonylbutylamino, Q is CH, X is C=O, m=2, n=2, A is O or N, $R^2$ is not present or $R^2$ is H, $CH_3$, $CH_2CH_3$.

In one embodiment is $R^1$ aminocarbonylbutylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ aminocarbonylbutylamino, Q is N, X is a bond or $CH_2$, m=2, n=2, A is O or N, $R^2$ is not present or $R^2$ is H, $CH_3$, $CH_2CH_3$.

In one embodiment is $R^1$ aminocarbonylbutylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ aminocarbonylbutylamino, Q is N, X is C=O, m=2, n=2, A is O or N, $R^2$ is not present or $R^2$ is H, $CH_3$, $CH_2CH_3$.

In one embodiment is $R^1$ aminocarbonylbutylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ aminocarbonylpentylamino, Q is CH, X is a bond or $CH_2$, m=2, n=2, A is O or N, $R^2$ is not present or $R^2$ is H, $CH_3$, $CH_2CH_3$.

In one embodiment is $R^1$ aminocarbonylpentylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ aminocarbonylpentylamino, Q is CH, X is C=O, m=2, n=2, A is O or N, $R^2$ is not present or $R^2$ is H, $CH_3$, $CH_2CH_3$.

In one embodiment is $R^1$ aminocarbonylpentylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ aminocarbonylpentylamino, Q is N, X is a bond or $CH_2$, m=2, n=2, A is O or N, $R^2$ is not present or $R^2$ is H, $CH_3$, $CH_2CH_3$.

In one embodiment is $R^1$ aminocarbonylpentylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ aminocarbonylpentylamino, Q is N, X is C=O, m=2, n=2, A is O or N, $R^2$ is not present or $R^2$ is H, $CH_3$, $CH_2CH_3$.

In one embodiment is $R^1$ aminocarbonylpentylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 2-dimethylamino-ethylamino, Q is CH, X is a bond or $CH_2$, m=2, n=2, A is O or N, $R^2$ is not present or $R^2$ is H, $CH_3$, $CH_2CH_3$.

In one embodiment is $R^1$ 2-dimethylamino-ethylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 2-dimethylamino-ethylamino, Q is CH, X is C=O, m=2, n=2, A is O or N, $R^2$ is not present or $R^2$ is H, $CH_3$, $CH_2CH_3$.

In one embodiment is $R^1$ 2-dimethylamino-ethylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 2-dimethylamino-ethylamino, Q is N, X is a bond or $CH_2$, m=2, n=2, A is O or N, $R^2$ is not present or $R^2$ is H, $CH_3$, $CH_2CH_3$.

In one embodiment is $R^1$ 2-dimethylamino-ethylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 2-dimethylamino-ethylamino, Q is N, X is C=O, m=2, n=2, A is O or N, $R^2$ is not present or $R^2$ is H, $CH_3$, $CH_2CH_3$.

In one embodiment is $R^1$ 2-dimethylamino-ethylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 3-dimethylamino-propylamino, Q is CH, X is a bond or $CH_2$, m=2, n=2, A is O or N, $R^2$ is not present or $R^2$ is H, $CH_3$, $CH_2CH_3$.

In one embodiment is $R^1$ 3-dimethylamino-propylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 3-dimethylamino-propylamino, Q is CH, X is C=O, m=2, n=2, A is O or N, $R^2$ is not present or $R^2$ is H, $CH_3$, $CH_2CH_3$.

In one embodiment is $R^1$ 3-dimethylamino-propylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 3-dimethylamino-propylamino, Q is N, X is a bond or $CH_2$, m=2, n=2, A is O or N, $R^2$ is not present or $R^2$ is H, $CH_3$, $CH_2CH_3$.

In one embodiment is $R^1$ 3-dimethylamino-propylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 3-dimethylamino-propylamino, Q is N, X is C=O, m=2, n=2, A is O or N, $R^2$ is not present or $R^2$ is H, $CH_3$, $CH_2CH_3$.

In one embodiment is $R^1$ 3-dimethylamino-propylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 4-dimethylamino-butylamino, Q is CH, X is a bond or $CH_2$, m=2, n=2, A is O or N, $R^2$ is not present or $R^2$ is H, $CH_3$, $CH_2CH_3$.

In one embodiment is $R^1$ 4-dimethylamino-butylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-dimethylamino-butylamino, Q is CH, X is C=O, m=2, n=2, A is O or N, $R^2$ is not present or $R^2$ is H, $CH_3$, $CH_2CH_3$.

In one embodiment is $R^1$ 4-dimethylamino-butylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 4-dimethylamino-butylamino, Q is N, X is a bond or $CH_2$, m=2, n=2, A is O or N, $R^2$ is not present or $R^2$ is H, $CH_3$, $CH_2CH_3$.

In one embodiment is $R^1$ 4-dimethylamino-butylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 4-dimethylamino-butylamino, Q is N, X is C=O, m=2, n=2, A is O or N, $R^2$ is not present or $R^2$ is H, $CH_3$, $CH_2CH_3$.

In one embodiment is $R^1$ 4-dimethylamino-butylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 5-dimethylamino-pentylamino, Q is CH, X is a bond or $CH_2$, m=2, n=2, A is O or N, $R^2$ is not present or $R^2$ is H, $CH_3$, $CH_2CH_3$.

In one embodiment is $R^1$ 5-dimethylamino-pentylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 5-dimethylamino-pentylamino, Q is CH, X is C=O, m=2, n=2, A is O or N, $R^2$ is not present or $R^2$ is H, $CH_3$, $CH_2CH_3$.

In one embodiment is $R^1$ 5-dimethylamino-pentylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 5-dimethylamino-pentylamino, Q is N, X is a bond or $CH_2$, m=2, n=2, A is O or N, $R^2$ is not present or $R^2$ is H, $CH_3$, $CH_2CH_3$.

In one embodiment is $R^1$ 5-dimethylamino-pentylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 5-dimethylamino-pentylamino, Q is N, X is C=O, m=2, n=2, A is O or N, $R^2$ is not present or $R^2$ is H, $CH_3$, $CH_2CH_3$.

In one embodiment is $R^1$ 5-dimethylamino-pentylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 6-dimethylamino-hexylamino, Q is CH, X is a bond or $CH_2$, m=2, n=2, A is O or N, $R^2$ is not present or $R^2$ is H, $CH_3$, $CH_2CH_3$.

In one embodiment is $R^1$ 6-dimethylamino-hexylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 6-dimethylamino-hexylamino, Q is CH, X is C=O, m=2, n=2, A is O or N, $R^2$ is not present or $R^2$ is H, $CH_3$, $CH_2CH_3$.

In one embodiment is $R^1$ 6-dimethylamino-hexylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 6-dimethylamino-hexylamino, Q is N, X is a bond or $CH_2$, m=2, n=2, A is O or N, $R^2$ is not present or $R^2$ is H, $CH_3$, $CH_2CH_3$.

In one embodiment is $R^1$ 6-dimethylamino-hexylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 6-dimethylamino-hexylamino, Q is N, X is C=O, m=2, n=2, A is O or N, $R^2$ is not present or $R^2$ is H, $CH_3$, $CH_2CH_3$.

In one embodiment is $R^1$ 6-dimethylamino-hexylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ 3-amino-2-hydroxy-propylamino, Q is CH, X is a bond or $CH_2$, m=2, n=2, A is O or N, $R^2$ is not present or $R^2$ is H, $CH_3$, $CH_2CH_3$.

In one embodiment is $R^1$ 3-amino-2-hydroxy-propylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 3-amino-2-hydroxy-propylamino, Q is CH, X is C=O, m=2, n=2, A is O or N, $R^2$ is not present or $R^2$ is H, $CH_3$, $CH_2CH_3$.

In one embodiment is $R^1$ 3-amino-2-hydroxy-propylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ 3-amino-2-hydroxy-propylamino, Q is N, X is a bond or $CH_2$, m=2, n=2, A is O or N, $R^2$ is not present or $R^2$ is H, $CH_3$, $CH_2CH_3$.

In one embodiment is $R^1$ 3-amino-2-hydroxy-propylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ 3-amino-2-hydroxy-propylamino, Q is N, X is C=O, m=2, n=2, A is O or N, $R^2$ is not present or $R^2$ is H, $CH_3$, $CH_2CH_3$.

In one embodiment is $R^1$ 3-amino-2-hydroxy-propylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ ureyl-ethylamino, Q is CH, X is a bond or $CH_2$, m=2, n=2, A is O or N, $R^2$ is not present or $R^2$ is H, $CH_3$, $CH_2CH_3$.

In one embodiment is $R^1$ ureyl-ethylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ ureyl-ethylamino, Q is CH, X is C=O, m=2, n=2, A is O or N, $R^2$ is not present or $R^2$ is H, $CH_3$, $CH_2CH_3$.

In one embodiment is $R^1$ ureyl-ethylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ ureyl-ethylamino, Q is N, X is a bond or $CH_2$, m=2, n=2, A is O or N, $R^2$ is not present or $R^2$ is H, $CH_3$, $CH_2CH_3$.

In one embodiment is $R^1$ ureyl-ethylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ ureyl-ethylamino, Q is N, X is C=O, m=2, n=2, A is O or N, $R^2$ is not present or $R^2$ is H, $CH_3$, $CH_2CH_3$.

In one embodiment is $R^1$ ureyl-ethylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ ureyl-propylamino, Q is CH, X is a bond or $CH_2$, m=2, n=2, A is O or N, $R^2$ is not present or $R^2$ is H, $CH_3$, $CH_2CH_3$.

In one embodiment is $R^1$ ureyl-propylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ ureyl-propylamino, Q is CH, X is C=O, m=2, n=2, A is O or N, $R^2$ is not present or $R^2$ is H, $CH_3$, $CH_2CH_3$.

In one embodiment is $R^1$ ureyl-propylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ ureyl-propylamino, Q is N, X is a bond or $CH_2$, m=2, n=2, A is O or N, $R^2$ is not present or $R^2$ is H, $CH_3$, $CH_2CH_3$.

In one embodiment is $R^1$ ureyl-propylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ ureyl-propylamino, Q is N, X is C=O, m=2, n=2, A is O or N, $R^2$ is not present or $R^2$ is H, $CH_3$, $CH_2CH_3$.

In one embodiment is $R^1$ ureyl-propylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ ureyl-butylamino, Q is CH, X is a bond or $CH_2$, m=2, n=2, A is O or N, $R^2$ is not present or $R^2$ is H, $CH_3$, $CH_2CH_3$.

In one embodiment is $R^1$ ureyl-butylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ ureyl-butylamino, Q is CH, X is C=O, m=2, n=2, A is O or N, $R^2$ is not present or $R^2$ is H, $CH_3$, $CH_2CH_3$.

In one embodiment is $R^1$ ureyl-butylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ ureyl-butylamino, Q is N, X is a bond or $CH_2$, m=2, n=2, A is O or N, $R^2$ is not present or $R^2$ is H, $CH_3$, $CH_2CH_3$.

In one embodiment is $R^1$ ureyl-butylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ ureyl-butylamino, Q is N, X is C=O, m=2, n=2, A is O or N, $R^2$ is not present or $R^2$ is H, $CH_3$, $CH_2CH_3$.

In one embodiment is $R^1$ ureyl-butylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ ureyl-pentylamino, Q is CH, X is a bond or $CH_2$, m=2, n=2, A is O or N, $R^2$ is not present or $R^2$ is H, $CH_3$, $CH_2CH_3$.

In one embodiment is $R^1$ ureyl-pentylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ ureyl-pentylamino, Q is CH, X is C=O, m=2, n=2, A is O or N, $R^2$ is not present or $R^2$ is H, $CH_3$, $CH_2CH_3$.

In one embodiment is $R^1$ ureyl-pentylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ ureyl-pentylamino, Q is N, X is a bond or $CH_2$, m=2, n=2, A is O or N, $R^2$ is not present or $R^2$ is H, $CH_3$, $CH_2CH_3$.

In one embodiment is $R^1$ ureyl-pentylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ ureyl-pentylamino, Q is N, X is C=O, m=2, n=2, A is O or N, $R^2$ is not present or $R^2$ is H, $CH_3$, $CH_2CH_3$.

In one embodiment is $R^1$ ureyl-pentylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ ureyl-hexylamino, Q is CH, X is a bond or $CH_2$, m=2, n=2, A is O or N, $R^2$ is not present or $R^2$ is H, $CH_3$, $CH_2CH_3$.

In one embodiment is $R^1$ ureyl-hexylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ ureyl-hexylamino, Q is CH, X is C=O, m=2, n=2, A is O or N, $R^2$ is not present or $R^2$ is H, $CH_3$, $CH_2CH_3$.

In one embodiment is $R^1$ ureyl-hexylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ ureyl-hexylamino, Q is N, X is a bond or $CH_2$, m=2, n=2, A is O or N, $R^2$ is not present or $R^2$ is H, $CH_3$, $CH_2CH_3$.

In one embodiment is $R^1$ ureyl-hexylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ ureyl-hexylamino, Q is N, X is C=O, m=2, n=2, A is O or N, $R^2$ is not present or $R^2$ is H, $CH_3$, $CH_2CH_3$.

In one embodiment is $R^1$ ureyl-hexylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ guanidyl-ethylamino, Q is CH, X is a bond or $CH_2$, m=2, n=2, A is O or N, $R^2$ is not present or $R^2$ is H, $CH_3$, $CH_2CH_3$.

In one embodiment is $R^1$ guanidyl-ethylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ guanidyl-ethylamino, Q is CH, X is C=O, m=2, n=2, A is O or N, $R^2$ is not present or $R^2$ is H, $CH_3$, $CH_2CH_3$.

In one embodiment is $R^1$ guanidyl-ethylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ guanidyl-ethylamino, Q is N, X is a bond or $CH_2$, m=2, n=2, A is O or N, $R^2$ is not present or $R^2$ is H, $CH_3$, $CH_2CH_3$.

In one embodiment is $R^1$ guanidyl-ethylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ guanidyl-ethylamino, Q is N, X is C=O, m=2, n=2, A is O or N, $R^2$ is not present or $R^2$ is H, $CH_3$, $CH_2CH_3$.

In one embodiment is $R^1$ guanidyl-ethylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ guanidyl-propylamino, Q is CH, X is a bond or $CH_2$, m=2, n=2, A is O or N, $R^2$ is not present or $R^2$ is H, $CH_3$, $CH_2CH_3$.

In one embodiment is $R^1$ guanidyl-propylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ guanidyl-propylamino, Q is CH, X is C=O, m=2, n=2, A is O or N, $R^2$ is not present or $R^2$ is H, $CH_3$, $CH_2CH_3$.

In one embodiment is $R^1$ guanidyl-propylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ guanidyl-propylamino, Q is N, X is a bond or $CH_2$, m=2, n=2, A is O or N, $R^2$ is not present or $R^2$ is H, $CH_3$, $CH_2CH_3$.

In one embodiment is $R^1$ guanidyl-propylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ guanidyl-propylamino, Q is N, X is C=O, m=2, n=2, A is O or N, $R^2$ is not present or $R^2$ is H, $CH_3$, $CH_2CH_3$.

In one embodiment is $R^1$ guanidyl-propylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ guanidyl-butylamino, Q is CH, X is a bond or $CH_2$, m=2, n=2, A is O or N, $R^2$ is not present or $R^2$ is H, $CH_3$, $CH_2CH_3$.

In one embodiment is $R^1$ guanidyl-butylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ guanidyl-butylamino, Q is CH, X is C=O, m=2, n=2, A is O or N, $R^2$ is not present or $R^2$ is H, $CH_3$, $CH_2CH_3$.

In one embodiment is $R^1$ guanidyl-butylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ guanidyl-butylamino, Q is N, X is a bond or $CH_2$, m=2, n=2, A is O or N, $R^2$ is not present or $R^2$ is H, $CH_3$, $CH_2CH_3$.

In one embodiment is $R^1$ guanidyl-butylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ guanidyl-butylamino, Q is N, X is C=O, m=2, n=2, A is O or N, $R^2$ is not present or $R^2$ is H, $CH_3$, $CH_2CH_3$.

In one embodiment is $R^1$ guanidyl-butylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ guanidyl-pentylamino, Q is CH, X is a bond or $CH_2$, m=2, n=2, A is O or N, $R^2$ is not present or $R^2$ is H, $CH_3$, $CH_2CH_3$.

In one embodiment is $R^1$ guanidyl-pentylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ guanidyl-pentylamino, Q is CH, X is C=O, m=2, n=2, A is O or N, $R^2$ is not present or $R^2$ is H, $CH_3$, $CH_2CH_3$.

In one embodiment is $R^1$ guanidyl-pentylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ guanidyl-pentylamino, Q is N, X is a bond or $CH_2$, m=2, n=2, A is O or N, $R^2$ is not present or $R^2$ is H, $CH_3$, $CH_2CH_3$.

In one embodiment is $R^1$ guanidyl-pentylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ guanidyl-pentylamino, Q is N, X is C=O, m=2, n=2, A is O or N, $R^2$ is not present or $R^2$ is H, $CH_3$, $CH_2CH_3$.

In one embodiment is $R^1$ guanidyl-pentylamino, Q is N, X is C=O, A is C, m=1, n=1, o=1, p=1, B is O or N, $R^3$ is not present or $R^3$ is H, $CH_3$, $CH_2CH_3$.

In one embodiment is $R^1$ guanidyl-hexylamino, Q is CH, X is a bond or $CH_2$, m=2, n=2, A is O or N, $R^2$ is not present or $R^2$ is H, $CH_3$, $CH_2CH_3$.

In one embodiment is $R^1$ guanidyl-hexylamino, Q is CH, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ guanidyl-hexylamino, Q is CH, X is C=O, m=2, n=2, A is O or N, $R^2$ is not present or $R^2$ is H, $CH_3$, $CH_2CH_3$.

In one embodiment is $R^1$ guanidyl-hexylamino, Q is CH, X is C=O, A is C, m=1, n=1, o=1, p=1, B is O or N, $R^3$ is not present or $R^3$ is H, $CH_3$, $CH_2CH_3$.

In one embodiment is $R^1$ guanidyl-hexylamino, Q is N, X is a bond or $CH_2$, m=2, n=2, A is O or N, $R^2$ is not present or $R^2$ is H, $CH_3$, $CH_2CH_3$.

In one embodiment is $R^1$ guanidyl-hexylamino, Q is N, X is a bond or $CH_2$, A is C, m=1, n=1, o=1, p=1, B is O or N, $R^3$ is not present or $R^3$ is H, $CH_3$, $CH_2CH_3$.

In one embodiment is $R^1$ guanidyl-hexylamino, Q is N, X is C=O, m=2, n=2, A is O or N, $R^2$ is not present or $R^2$ is H, $CH_3$, $CH_2CH_3$.

In one embodiment is $R^1$ guanidyl-hexylamino, Q is N, X is C=O, A is C, m=1, n=1, o=1, p=1, B is O or N, $R^3$ is not present or $R^3$ is H, $CH_3$, $CH_2CH_3$.

Preferably, the compounds of the general formula I are selected from the group containing: $N^2$-(4-amino-cyclohexyl)-9-cyclopentyl-M-(4-morpholino-4-ylmethyl-phenyl)-9H-purin-2,6-diamin, $N^2$-(4-amino-butyl)-9-cyclopentyl-M-(4-morpholin-4-ylmethyl-phenyl)-9H-purin-2,6-diamin, $N^2$-(4-amino-cyclohexyl)-9-cyclopentyl-M-(4-morpholin-4-yl-phenyl)-9H-purin-2,6-diamin, $N^2$-(4-amino-butyl)-9-cyclopentyl-M-(4-morpholin-4-yl-phenyl)-9H-purin-2,6-diamin, $N^2$-(4-amino-butyl)-9-cyclopentyl-M-[4-(4-ethyl-piperazin-1-yl)-phenyl]-9H-purin-2,6-diamin, $N^2$-(4-amino-cyclohexyl)-9-cyclopentyl-M-[4-(2-oxa-6-aza-spiro[3.3]hept-6-yl)-phenyl]-9H-purin-2,6-diamin, 4-[9-Cyclopentyl-6-(4-morpholin-4-ylmethyl-phenylamino)-9H-purin-2-ylamino]-butan-1-ol, ($N^2$-(4-amino-cyclohexyl)-9-cyclopentyl-M-(4-pyrrolidin-1-yl-phenyl)-9H-purin-2,6-diamin), $N^2$-(4-amino-butyl)-9-cyclopentyl-N-[6-(2-oxa-6-aza-spiro[3.3]hept-6-yl)-pyridin-3-yl]-9H-purin-2,6-diamin, $N^2$-(5-amino-pentyl)-9-cyclopentyl-2V-(4-morpholin-4-ylmethyl-phenyl)-9H-purin-2,6-diamin, 9-cyclopentyl-$N^2$-(4-dimethylamino-butyl)-N-(6-morpholin-4-yl-pyridin-3-yl)-9H-purin-2,6-diamin.

Pharmaceutical Compositions

The therapeutic compositions comprise about 1% to about 95% of the active ingredient, single-dose forms of administration preferably comprising about 20% to about 90% of the active ingredient, and administration forms which are not single-dose preferably comprising about 5% to about 20% of the active ingredient. Unit dose forms may be, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient. The pharmaceutical compositions of the present invention are prepared in a known manner, for example by means of conventional mixing, granulating, coating, dissolving or lyophilizing processes.

Preferably, solutions of the active ingredient, and in addition also suspensions or dispersions, especially isotonic aqueous solutions, dispersions or suspensions, are used, if being possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of conventional dissolving or lyophilising processes. The solutions or suspensions mentioned can comprise viscosity-increasing substances, such as sodium carboxymethylcellulose, dextran, polyvinylpyrrolidone or gelatine.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidonic acid, behenic acid or corresponding unsaturated acids, for example oleic acid, elaidic acid, erucic acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_2$ from Hils AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example into ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatine and soft, closed capsules of gelatine and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycol or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of from about 5% to about 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and, if appropriate, stabilizers. The active ingredient can also be present here in the form of a lyophilisate, if appropriate, together with excipients, and be dissolved before parenteral administration by addition of suitable solvents.

Solutions such as are used, for example, for parental administration can also be used as infusion solutions. Preferred preservatives are, for example, antioxidants, such as ascorbic acid, or microbicides, such as sorbic or benzoic acid.

Ointments are oil-in-water emulsions which comprise not more than 70%, preferably 20-50% of water or aqueous phase. The fatty phase consists, in particular, hydrocarbons, for example vaseline, paraffin oil or hard paraffins, which preferably comprise suitable hydroxy compounds, such as fatty alcohols or esters thereof, for example cetyl alcohol, or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with ethanol, and, if necessary, other excipients and additives, are admixed.

The invention also relates to a process or method of treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of the compound according to the present invention is administered here for a body weight of about 70 kg.

EXAMPLES OF CARRYING OUT THE INVENTION

Figure 1:
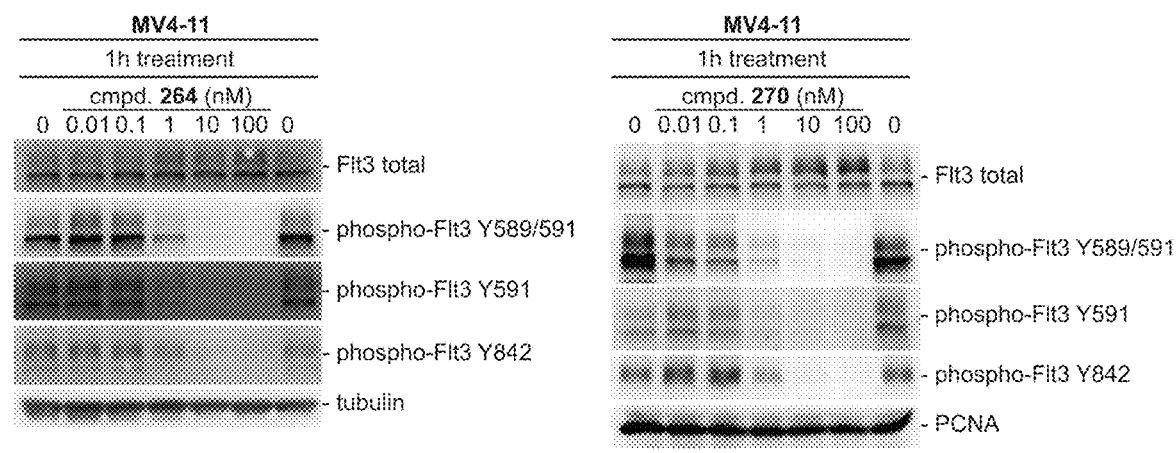
FIG. 1 shows immunoblotting analysis of FLT3 phosphorylation in MV4-11 cells (expressing FLT3-TTD) treated with compounds 264 and 270. Cells were exposed for 1 hour to the indicated concentrations of 264 or 270 and then levels of phosphorylations at specific tyrosine residues of FLT3 were analyzed.

The following examples serve to illustrate the invention without limiting the scope thereof. Unless stated otherwise, all percentages are reported by weight.

The starting materials for the compounds of the formula I are commercially available (Sigma-Aldrich, Fluka, etc.) or may be prepared as described below.

Thin layer chromatography was performed on silica 60 F254 plates (Merck) using $CHCl_3$/MeOH as the mobile phase. Spot detection was done by UV irradiation (254 and 365 nm).

Chromatographic purification of the intermediates and final products was performed on a Davisil 40-63 micron silica column (Grace and Davision). Elemental analysis was performed on an EA 1112 analyzer (Thermo Scientific); their values (C, H, N) agreed with the calculated ones within acceptable limits.

Melting points were determined on a Boetius stage and are corrected. $^1$H NMR spectra were measured in $CDCl_3$ or in DMSO-$d_6$ at 300 K on a Bruker Avance 300 NMR spectrometer (300 MHz) with TMS as an internal standard; chemical shifts are reported in ppm, and coupling constants in Hz. Mass spectra were recorded by using an LCQ ion trap mass spectrometer (Finnigan MAT, San Jose, Calif., USA). Merck silica gel Kieselgel 60 (230-400 mesh) was used for column chromatography. Quadrupole mass spectra were measured on a Micromass ZMD detector with electrospray ionization.

The synthesis started from commercially available 2,6-dichloropurine, which was in the first step alkylated by cyclopentanol via Mitsunobu alkylation to obtain 9-cyclopentyl-2,6-dichloro-9H-purine. Some of the used 4-substituted-anilino or 2-substituted-5-aminopyridine derivatives were commercially available and some of them were synthesized using common synthetic approaches. The substitution of 4-bromonitrobenzene or 2-bromo-5-nitropyridine with corresponding cyclic secondary amine yielded nitroderivatives (3) which were reduced with hydrogen on palladium under atmospheric pressure to corresponding derivatives (4), N,N-disubstituted-benzene-1,4-diamines or $N^2,N^2$-disubstituted-pyridine-2,5-diamines (see Scheme 1).

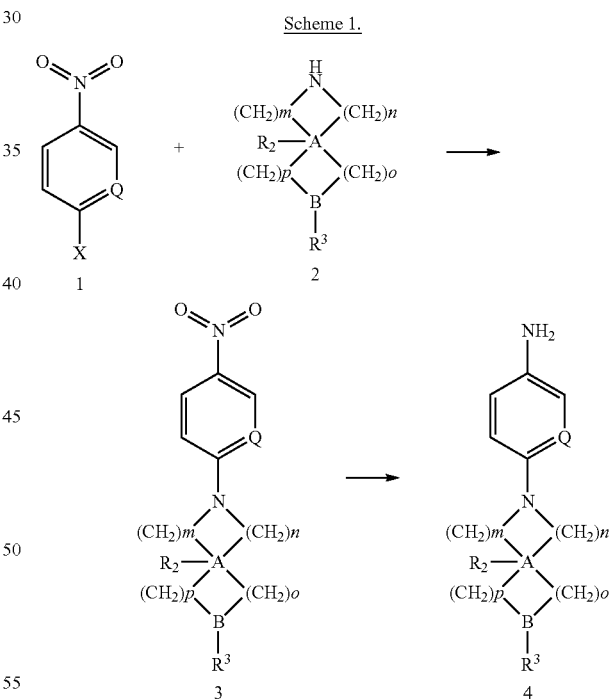

General Procedure for the Preparation of Derivatives (4)

4-Fluoronitrobenzene or 5-bromo-2-nitropyridine (1.00 mmol), corresponding secondary amine (1.05 mmol) and potassium carbonate (2.00 mmol) in ethanol (10 ml) was heated under an argon atmosphere in a sealed tube at 100° C. for 4 hours. The completion of the reaction was checked with TLC on silica (chloroform-methanol 19:1). After cooling to room temperature the reaction mixture was evaporated under reduced pressure. The residue was partitionated between dichloromethane (25 ml) and water (25 ml). The water phase was extracted twice with dichloromethane (25 ml). The combined organic phases were washed with water, brine, dried over sodium sulphate and concentrated under reduced pressure. The crude product was used to further step without purification. The crude product from previous step (0.75 mmol) was hydrogenated under atmospheric pressure in methanol (50 ml) with 5% wt. palladium on a charcoal (50 mg). After consumption of hydrogen the reaction mixture was filtered through celite, washed with methanol and evaporated under reduced pressure. The crude product was dissolved in 2 M hydrochloric acid (50 ml) and extracted with dichloromethane (25 ml). The water phase was neutralised with 5% sodium hydrogencarbonate, the precipitate was filtered off and washed with water. The crude product was dried in vacuum dessicator.

Example 1

6-(4-Nitro-phenyl)-2-oxa-6-aza-spiro[3.3]heptane

Yield: 72%. Elemental analysis: Calcd. for $C_{11}H_{12}N_2O_3$ (220.22): C, 59.99; H, 5.49; N, 12.72.

Found: C, 59.66; H, 5.12; N, 12.19. HPLC-MS (ESI+): 221.36 (99.7%). GC-MS (EI, M+(rel.int. m/z): 220 (21), 150 (100), 120 (57). $^1$H NMR (DMSO-d$_6$): 4.19-4.21 (m, 4H), 4.70-4.72 (m, 4H), 6.44 (d, J=9.15, 2H), 8.04 (d, J=9.15, 2H).

4-(2-Oxa-6-aza-spiro[3.3]hept-6-yl)-phenylamine

Yield: 58%. Elemental analysis: Calcd. for $C_{11}H_{14}N_2O$ (190.24): C, 69.45; H, 7.42; N, 14.73.

Found: C, 69.13; H, 7.12; N, 14.96. HPLC-MS (ESI+): 191.5 (99.7%). GC-MS (EI, M+ (rel.int. m/z): 190 (11), 132 (100). $^1$H NMR (DMSO-d$_6$): 3.72-3.75 (m, 4H), 4.40 (s(br), 2H, NH$_2$), 4.65-4.68 (m, 4H), 6.21 (d, J=8.16, 2H, ArH), 6.46 (d, J=8.15, 2H, ArH).

Similarly the preparation of 4-(N,N-disubstituted-aminomethyl)phenylamines and 6-(N,N-disubstitutedaminomethyl)-pyridin-3-ylamines (8) was performed by the reductive amination of 4-nitrobenzaldehyde or 5-nitropyridine-2-carbaldehyde with corresponding cyclic secondary amine using sodium triacetoxyborohydride/acetic acid in N,N-dimethylformamide. The nitrogroup was reduced with hydrazine hydrate on Raney nickel (see Scheme 2).

Scheme 2.

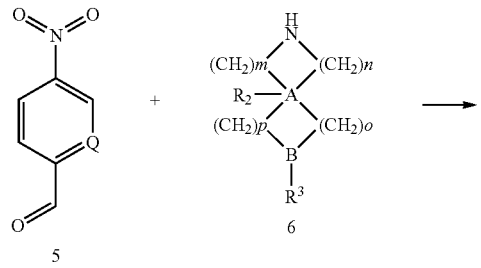

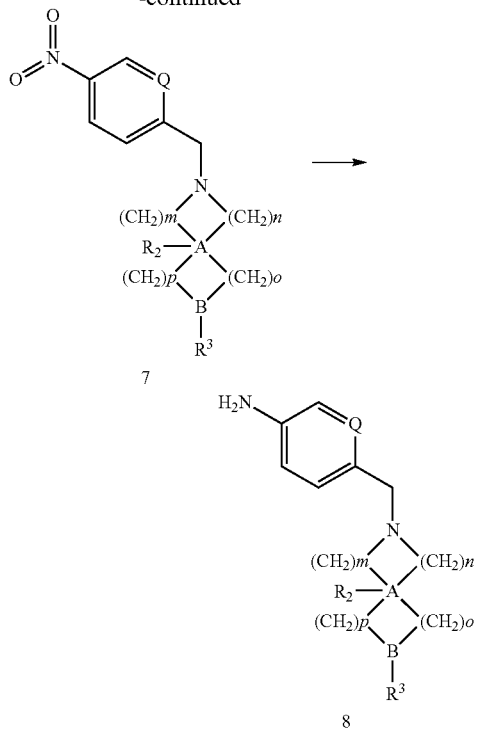

General Procedure for the Preparation of Derivatives 8

To a stirred solution of 4-nitrobenzaldehyde or 5-nitropyridine-2-carbaldehyde (3.00 mmol), sodium triacetoxyborohydride (3.60 mmol) and acetic acid (3.00 mmol) in anhydrous tetrahydrofurane (10 ml) was added dropwise corresponding secondary amine (3.00. mmol) at room temperature. The reaction mixture was stirred for 4 hours at room temperature. Methanol (10 ml was added to the reaction mixture and the solution was evaporated under reduced pressure. The residue was partitionated between saturated sodium hydrogencarbonate water solution (15 ml) and ethylacetate (15 ml). The water phase was extracted twice with ethylacetate. The combined organic phases were washed with brine, dried over sodium sulphate and evaporated under reduced pressure. The crude product was purified by flash chromatography on silica using mobile phase petroleum ether-ethylacetate 3:1.

The nitroderivative (10.0 mmol) was dissolved in ethanol (5 ml) and Raney nickel (50 mg) was added. The reaction mixture was heated to 50° C. and hydrazine hydrate 80% (15.0 mmol) was slowly added with vigorous stirring during a 30 min period. The mixture was heated at 50° C. for further 30 minutes, cooled to room temperature, filtered through celite and washed with ethanol. The filtrate was evaporated under reduced pressure and the crude product was purified by flash chromatography on silica using chloroform-methanol 4:1.

Example 2

6-(4-Nitro-benzyl)-2-oxa-6-aza-spiro[3.3]heptane

Yield: 57%; Elemental analysis: Calcd. for $C_{12}H_{14}N_2O_3$ (234.26): C, 61.53; H, 6.02; N, 11.96.

Found: C, 61.22; H, 6.12; N, 11.92. HPLC-MS (ESI+): 235.27 (98.7%). $^1$H NMR (DMSO-d$_6$): 3.32-3.35 (m, 4H), 3.63 (s, 2H, CH$_2$), 4.60-4.63 (m, 4H), 7.52 (d, J=8.67, 2H, ArH), 8.16 (d, J=8.67, 2H, ArH).

4-(2-Oxa-6-aza-spiro[3.3]hept-6-ylmethyl)-phenylamine

Yield: 86%; Elemental analysis: Calcd. for C$_{12}$H$_{16}$N$_2$O (204.24): C, 70.56; H, 7.90; N, 13.71.

Found: C, 70.45; H, 7.82; N, 13.29. HPLC-MS (ESI+): 205.32 (96.7%). $^1$H NMR (DMSO_d$_6$): 3.70-3.73 (m, 4H), 4.45 (s(br), 2H, NH$_2$), 4.52-4.55 (m, 4H), 6.25 (d, J=7.80, 2H, ArH), 6.49 (d, J=7.80, 2H, ArH).

The last type of used amine precursors, 4-amino-N,N-disubstituted benzamides and 5-aminopyridine-2-carboxylicacid-N,N-disubstituted amides were prepared from 4-nitrobenzoyl chloride and 5-nitro-pyridine-2-carbonyl chloride and corresponding secondary amines. The nitro-group of these intermediates was reduced with hydrazine hydrate on Raney nickel (see Scheme 3).

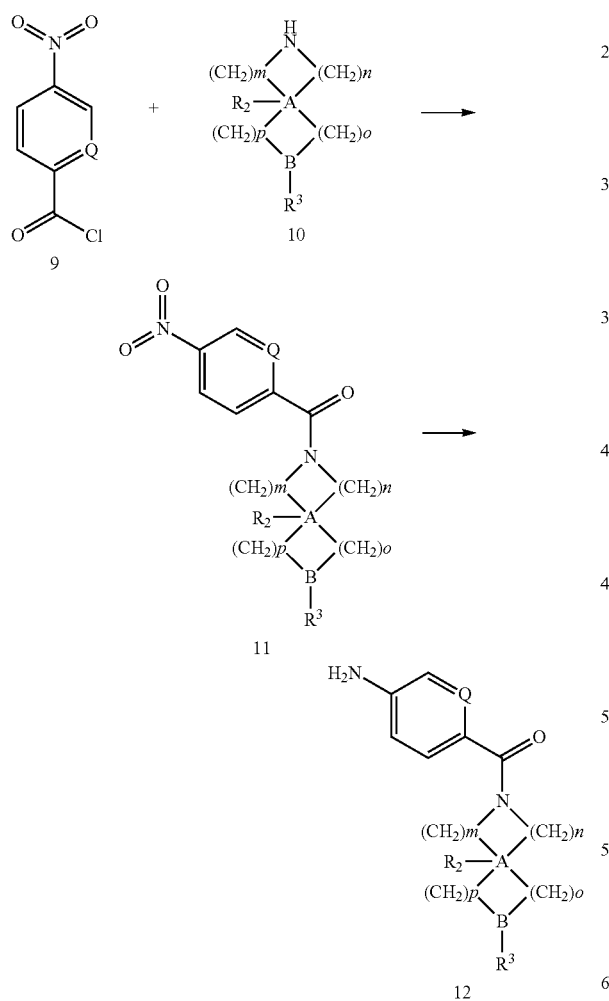

General Procedure for the Preparation of Derivatives 12:

To the solution of 4-nitrobenzoyl chloride or 5-nitro-pyridine-2-carbonyl chloride (20.0 mmol) and trimethylamine (20.0 mmol) in tetrahydrofuran (15 ml) appropriate secondary amine was added dropwise with stirring at room temperature. The reaction mixture was heated at 50° C. for further 2 hours. After cooling to room temperature, the solid was filtered off and washed with tetrahydrofuran. The filtrate was evaporated under reduced pressure and the residue was purified by crystallisation from ethanol.

The nitroderivative (10.0 mmol) was dissolved in ethanol (5 ml) and Raney nickel (50 mg) was added. The reaction mixture was heated to 50° C. and hydrazine hydrate 80% (15.0 mmol) was slowly added with vigorous stirring during a 30 min period. The mixture was heated at 50° C. for further 30 minutes, cooled to room temperature, filtered through celite and washed with ethanol. The filtrate was evaporated under reduced pressure and the crude product was purified by flash chromatography on silica using chloroform-methanol 4:1.

Example 3

6-(4-nitrobenzoyl)-2-oxa-6-azaspiro[3.3]heptan

Yield: 93%; Elemental analysis: Calcd. for C$_{12}$H$_{12}$N$_2$O$_4$ (248.23): C, 58.06; H, 4.87; N, 11.29.

Nalezeno: C, 58.24; H, 5.12; N, 11.01. HPLC-MS (ESI+): 249.26 (99.4%). $^1$H NMR (DMSO_d$_6$): 3.72-3.76 (m, 4H), 4.94-5.02 (m, 4H), 8.02 (d, J=8.32, 2H, ArH), 8.54 (d, J=8.32, 2H, ArH).

4-(2-oxa-6-azaspiro[3.3]hept-6-ylcarbonyl)aniline

Yield: 76%; Elemental analysis: Calcd. for C$_{12}$H$_{14}$N$_2$O$_2$ (218.25): C, 66.04; H, 6.47; N, 11.29.

Nalezeno: C, 65.79; H, 6.58; N, 12.51. HPLC-MS (ES+): 219.30 (95.4%). $^1$H NMR (DMSO_d$_6$): 3.82-3.88 (m, 4H), 4.41 (s(br), 2H, NH$_2$), 4.54-4.58 (m, 4H), 6.51 (d, J=7.55, 2H, ArH), 7.29 (d, J=7.55, 2H, ArH).

The nucleophilic substitution at the position 6 of the purine nucleus position was accomplished by reacting 9-cyclopentyl-2,6-dichloro-9H-purine (13) with the corresponding 4-substituted aniline or 2-substituted 5-aminopyridine in the presence of Hünig's base (15). Some of the compounds (15) were also prepared by reacting the bromoderivative (14) with the corresponding secondary amine under the modified Hartwig-Buchwald amination conditions (see Scheme 4).

Scheme 4.

a) corresponding primary amine; DIPEA, n-propanol, 120° C., pressure tube

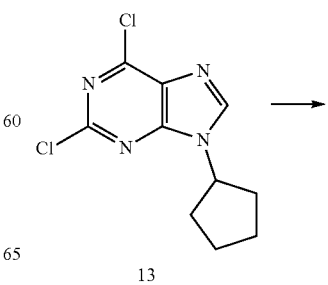

13

-continued

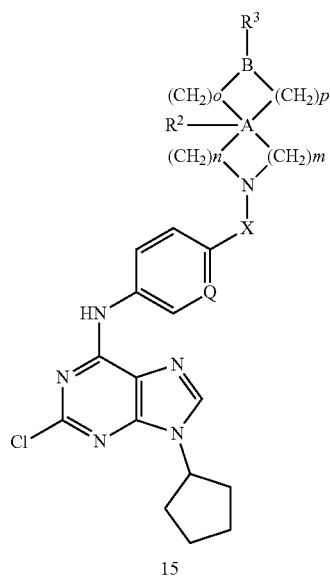

15 b) corresponding secondary amine; Pd(dba)₂, racBINAP, t-BuOK, toluene,100° C., 10-48 h

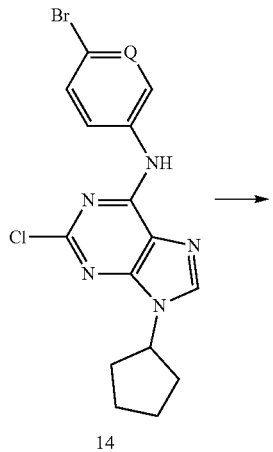

14

→

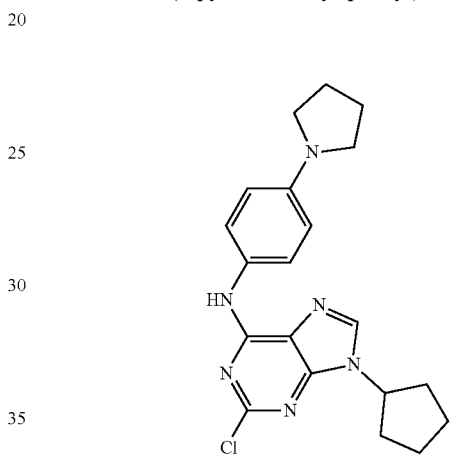

15

General Procedure a for the Preparation of Compounds 15:

To the suspension of 9-cyclopentyl-2,6-dichloro-9H-purine (13) (1.98 mmol) in a mixture of n-propanol (10 ml) and N,N-diisopropyl-N-ethylamine (8.72 mmol), appropriate amine (2.18 mmol) was added. The suspension was heated with stirring in a sealed tube under an argon atmosphere at the temperature 100° C. for 2-6 hours. The reaction was checked by TLC. After completion of the reaction the reaction mixture was cooled to room temperature and evaporated under reduced pressure. The residue was partitioned between water (50 ml) and dichloromethane (50 ml). The water phase was extracted twice with dichloromethane additionally. The combined organic phases were washed with water and brine and evaporated under reduced pressure. The crude product was crystallized from petroleum ether-ethylacetate 3:1.

Example 4 (2-Chloro-9-cyclopentyl-9H-purin-6-yl)-(4-pyrrolidin-1-yl-phenyl)-amine

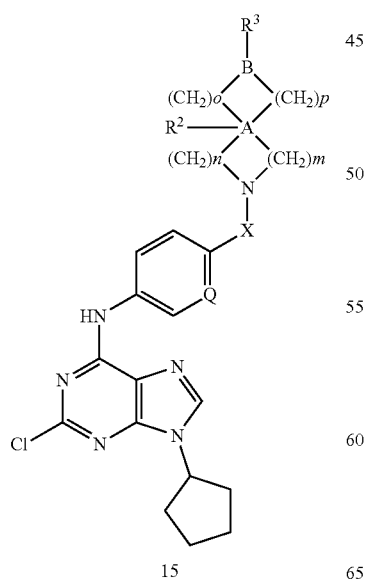

Yield: 92%. Elemental analysis: Calcd. for $C_{20}H_{23}ClN_6$ (382.89): C, 62.74; H, 6.05; N, 21.95.

Found: C, 62.54; H, 5.82; N, 21.83. HPLC-MS (ESI+): 384 (99.9%). $^1$H NMR (DMSO_$d_6$): 1.63-1.81 (m, 2H), 1.86-1.99 (m, 8H), 2.14-2.21 (m, 2H), 3.19-3.23 (m, 4H, $CH_2$), 4.81 (qui, J=7.17, 1H, CH), 6.53 (d, J=8.73, 2H, ArH), 7.519 (d, J=8.73, 2H, ArH), 8.32 (s, 1H, CH), 9.92 (s, 1H, NH).

Example 5 (2-Chloro-9-cyclopentyl-9H-purin-6-yl)-(4-morpholin-4-yl-phenyl)-amine

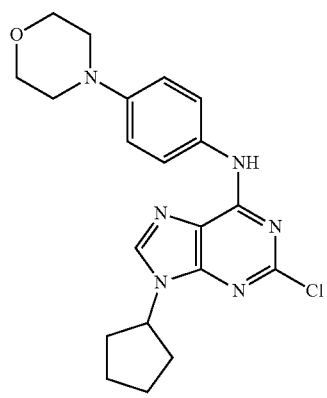 [SMILES: Clc1nc(Nc2ccc(N3CCOCC3)cc2)c2ncn(C3CCCC3)c2n1]

Yield: 72%. Elemental analysis: Calcd. for $C_{20}H_{23}ClN_6O$ (398.89): C, 60.22; H, 5.81; N, 21.07.

Found: C, 60.25; H, 5.88; N, 21.19. HPLC-MS (ESI+): 400.7 (98.5%). $^1$H NMR (DMSO_$d_6$): 1.79-1.83 (m, 2H), 1.85-1.96 (m, 4H), 2.27-2.36 (m, 2H), 3.14-3.18 (m, 2H), 3.88-3.90 (m, 2H), 4.94 (qui, J=7.32, 1H, CH), 6.97 (d, J=8.94, 2H, ArH), 7.65 (d, J=8.94, 2H, ArH), 7.80 (s (br), 1H, NH), 7.83 (s, 1H, CH).

$^{13}$C NMR (DMSO_$d_6$): 23.91, 33.04, 49.89, 55.97, 66.96, 116.54, 119.28, 121.89, 130.84, 138.78, 148.11, 150.70, 152.48, 154.03.

Example 6 ((2-Chloro-9-cyclopentyl-9H-purin-6-yl)-(4-morpholin-4-ylmethyl-phenyl)-amine)

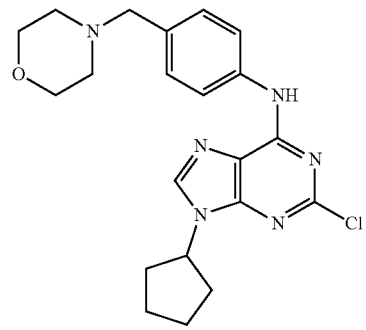 [SMILES: Clc1nc(Nc2ccc(CN3CCOCC3)cc2)c2ncn(C3CCCC3)c2n1]

Yield: 69%. Elemental analysis: Calcd. for $C_{21}H_{25}ClN_6O$ (412.92): C, 61.08; H, 6.10; N, 20.35.

Found: C, 61.33; H, 5.99; N, 20.02. HPLC-MS (ESI+): 414.2 (99.5%). $^1$H NMR (CDCl$_3$): 1.78-1.82 (m, 2H), 1.84-1.99 (m, 4H), 2.28-2.36 (m, 2H), 2.47-2.52 (m, 4H), 3.53 (s, 2H), 3.70-3.74 (m, 4H), 4.95 (qui, J=5.4, 1H), 7.37 (d, J=8.22, 2H, ArH), 7.74 (d, J=8.22, 2H, ArH), 7.86 (s, 1H, CH).

Example 7 (2-Chloro-9-cyclopentyl-9H-purin-6-yl)-[4-(4-ethyl-piperazin-1-yl)-phenyl]-amine)

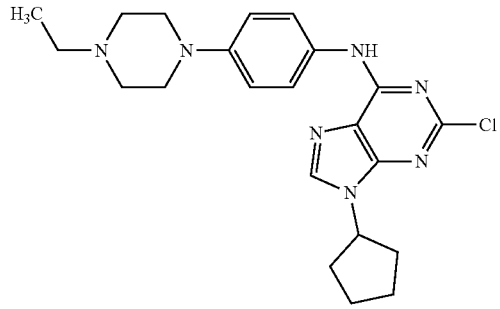 [SMILES: CCN1CCN(c2ccc(Nc3nc(Cl)nc4c3ncn4C3CCCC3)cc2)CC1]

Yield: 82%. Elemental analysis: Calcd. for $C_{22}H_{28}ClN_7$ (425.96): C, 62.03; H, 6.63; N, 23.02.

Found: C, 61.93; H, 6.79; N, 23.22. HPLC-MS (ESI+): 427.3 (99.5%). $^1$H NMR (CDCl$_3$): 1H NMR (CDCl3): 1.16 (t, J=7.2, 3H, CH$_3$), 1.77-1.81 (m, 2H), 1.90-1.95 (m, 4H), 2.26-2.32 (m, 2H), 2.48 (q, J=7.02, 2H, CH$_2$), 2.62-2.66 (m, 4H), 3.21-3.25 (m, 4H), 4.91 (qui, J=6.9, 1H, CH), 6.97 (d, J=9.00, 2H, ArH), 7.63 (d, J=9.00, 2H, ArH), 7.80-7.83 (m, 2H, CH, NH).

$^{13}$C NMR (CDCl$_3$): 11.40, 17.90, 23.26, 32.42, 48.92, 51.82, 52.24, 55.28, 57.79, 116.15, 118.63, 121.18, 129.79, 138.06, 147.64, 150.01, 151.85, 153.40.

Example 8 (2-Chloro-9-cyclopentyl-9H-purin-6-yl)-[4-(2-oxa-6-aza-spiro[3.3]hept-6-yl)-phenyl]-amine)

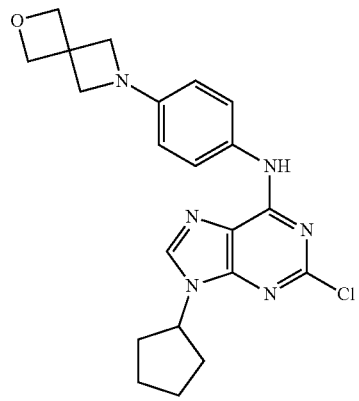 [SMILES: Clc1nc(Nc2ccc(N3CC4(COC4)C3)cc2)c2ncn(C3CCCC3)c2n1]

Yield: 74%. Elemental analysis: Calcd. for $C_{21}H_{23}ClN_6O$ (410.90): C, 61.38; H, 5.64; N, 20.45.

Found: C, 61.14; H, 5.39; N, 20.19. HPLC-MS (ESI+): 411.9 (97.7%). $^1$H NMR (DMSO d-6): 1.67-1.72 (m, 2H), 1.84-1.99 (m, 4H), 2.11-2.18 (m, 2H), 2.45-2.50 (m, 4H), 4.70-4.72 (m, 4H), 3.92-3.94 (m, 4H), 4.81 (qui, J=5.4, 1H), 6.43 (d, J=8.70, 2H, ArH), 7.53 (d, J=8.70, 2H, ArH), 8.33 (s, 1H, CH), 9.99 (s, 1H, NH).

Example 9 (2-Chloro-9-cyclopentyl-9H-purin-6-yl)-(6-morpholin-4-yl-pyridin-3-yl)-amine

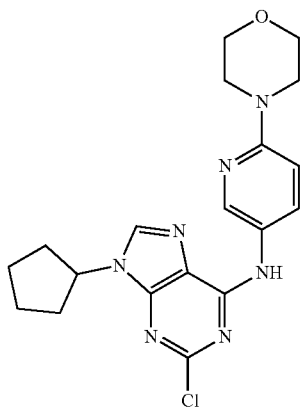 [SMILES: Clc1nc(Nc2ccc(N3CCOCC3)nc2)c2ncn(C3CCCC3)c2n1]

Yield: 88%. Elemental analysis: Calcd. for $C_{19}H_{22}ClN_7O$ (399.88): C, 57.07; H, 5.55; N, 24.52.

Found: C, 57.23; H, 5.21; N, 24.14. HPLC-MS (ESI+): 400.9 (99.5%). $^1$H NMR (DMSO_$d_6$): 1.79-1.83 (m, 2H), 1.85-1.96 (m, 4H), 2.27-2.36 (m, 2H), 3.14-3.18 (m, 2H), 3.88-3.90 (m, 2H), 4.91 (qui, J=6.55, 1H, CH), 6.93 (s, 1H, ArH), 7.41-7.47 (m, 2H, ArH), 7.98 (s, 1H), 8.25 (s(br), 1H, NH).

General Procedure B for the Preparation of Compounds 15

The mixture of bromoderivative 14 (0.35 mmol), appropriate amine (0.40 mmol), potassium tert.butoxide (0.53 mmol), rac-BINAP (30 μmol), palladium bis(dibenzylideneaceton) (15 μmol) in dry toluene (5 ml) was heated under an argon atmosphere in a sealed tube at 100° C. for 10-48 hours. After completion of the reaction the reaction mixture was cooled to room temperature, filtered through celite and washed with small amount of toluene. The filtrate was evaporated under reduced pressure and the residue was partionated between water (15 ml) and ethylacetate (15 ml). The water phase was extracted twice with ethylacetate. Combined organic phases were washed with water, brine, dried over sodium sulphate and evaporated under reduced pressure. The crude product was purified by column chromatography on silica using mobile phase chloroform-methanol (19:1).

Example 10 [4-(2-Chloro-9-cyclopentyl-9H-purin-6-ylamino)-phenyl]-(2-oxa-6-aza-spiro[3.3]hept-6-yl)-methanone

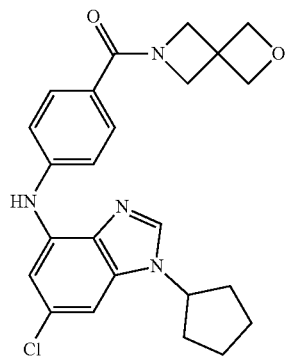

Yield: 58%. Elemental analysis: Calcd. for $C_{22}H_{23}ClN_6O_2$ (438.91): C, 60.20; H, 5.28; N, 19.15.

Found: C, 60.19; H, 5.14; N, 18.89. HPLC-MS (ESI+): 439.9 (95.9%). $^1$H NMR (DMSO d-6): 1.67-1.72 (m, 2H), 1.84-1.99 (m, 4H), 2.11-2.18 (m, 2H), 2.47-2.52 (m, 4H), 4.76 (qui, J=5.5, 11), 4.95-5.06 (m, 4H), 7.78 (d, J=8.90, 2H, ArH), 8.57 (d, J=8.90, 2H, ArH), 8.35 (s, 1H, CH), 9.92 (s, 1H, NH).

The substitution of chlorine in position 2 with primary or secondary amine was performed with a large excess of used amine in 1,2-ethandiole at 160° C. The reaction proceeded smoothly with a good yield and purity of prepared compounds (see Scheme 5).

Scheme 5.

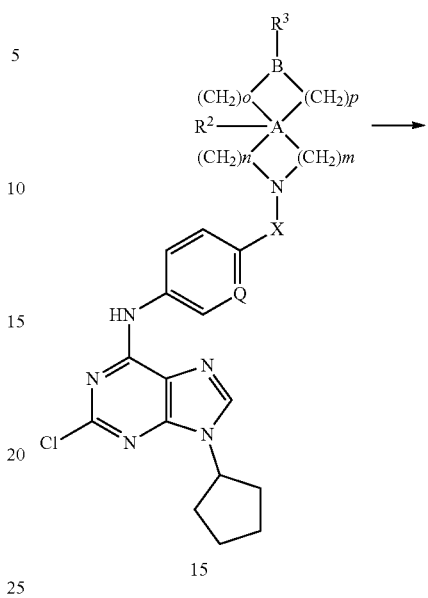

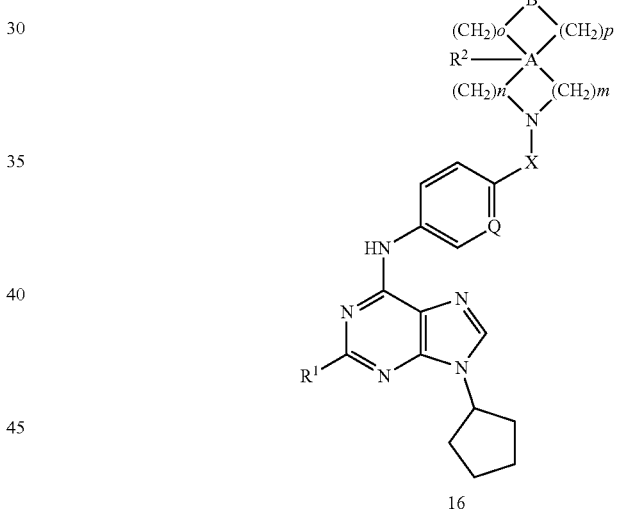

General Procedure for the Preparation of Compounds (16):

The mixture of 2-chloro-9-cyclopentyl-9H-purine-6-subst.amino derivative 15 (1.00 mmol) and trans-1,4-diaminocyclohexane (10.0 mmol) in 1,2-ethandiole (5 ml) was heated with stirring at 160° C. for 4 hours in an argon atmosphere. After cooling to room temperature, the mixture was diluted with ethylacetate (40 ml) and washed with water (40 ml). The organic phase was washed with brine, dried over sodium sulphate and concentrated under reduced pressure. The crude product was purified by column chromatography on silica using mobile phase chloroform—methanol (4:1, v/v).

Example 11 N²-(4-Amino-cyclohexyl)-9-cyclopentyl-N-[4-(2-oxa-6-aza-spiro[3.3]hept-6-yl)-phenyl]-9H-purine-2,6-diamine

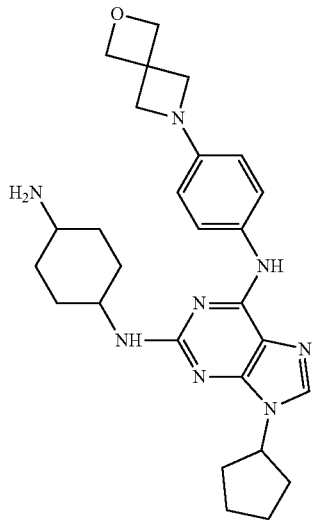 [SMILES: NC1CCC(Nc2nc(Nc3ccc(N4CC5(COC5)C4)cc3)c3ncn(C4CCCC4)c3n2)CC1]

Yield: 82%. Elemental analysis: Calcd. for $C_{27}H_{36}N_8O$ (488.63): C, 66.37; H, 7.43; N, 22.93.

Found: C, 66.11; H, 7.08; N, 22.69. HPLC-MS (ESI+): 489.7 (98.3%). ¹H NMR (DMSO d-6): H NMR (DMSO d-6): 1.67-2.07 (m, 14H), 2.11-2.18 (m, 2H), 2.45-2.50 (m, 4H), 4.71-4.74 (m, 4H), 3.92-3.94 (m, 4H), 4.83 (qui, J=5.4, 1H), 5.48 (d, J=5.44, 1H, NH), 6.48 (d, J=8.50, 2H, ArH), 7.55 (d, J=8.50, 2H, ArH), 8.32 (s, 1H, CH), 9.95 (s, 1H, NH).

Example 12 (N²-(4-Amino-cyclohexyl)-9-cyclopentyl-N⁶-(4-pyrrolidin-1-yl-phenyl)-9H-purine-2,6-diamine)

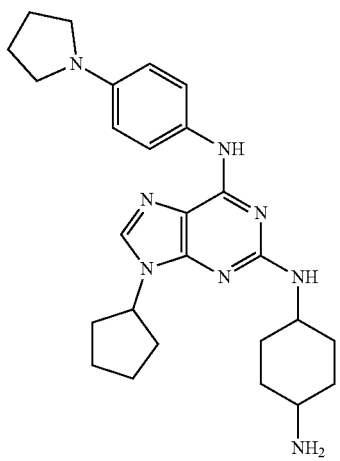 [SMILES: NC1CCC(Nc2nc(Nc3ccc(N4CCCC4)cc3)c3ncn(C4CCCC4)c3n2)CC1]

Yield: 92%. Elemental analysis: Calcd. for $C_{26}H_{36}N_8$ (460.62): C, 67.80; H, 7.88; N, 24.33.

Found: C, 67.71; H, 7.49; N, 24.01. HPLC-MS (ESI+): 461.7 (99.6%). ¹H NMR (DMSO d-6): 1.17-1.38 (m, 2H), 1.74-2.06 (m, 14H), 2.20-2.24 (m, 4H), 2.75 (sep, J=4.26, 1H), 3.27-3.31 (m, 4H), 3.81 (sex, J=5.97, 1H), 4.69-4.79 (m, 2H), 6.56 (d, J=8.73, 2H, ArH), 7.36 (s(br), 1H, NH), 7.52 (s, 1H, CH), 7.58 (d, J=8.73, 2H, ArH).

Example 13 N²-(4-Amino-butyl)-9-cyclopentyl-N⁶-(4-morpholin-4-yl-phenyl)-9H-purine-2,6-diamine

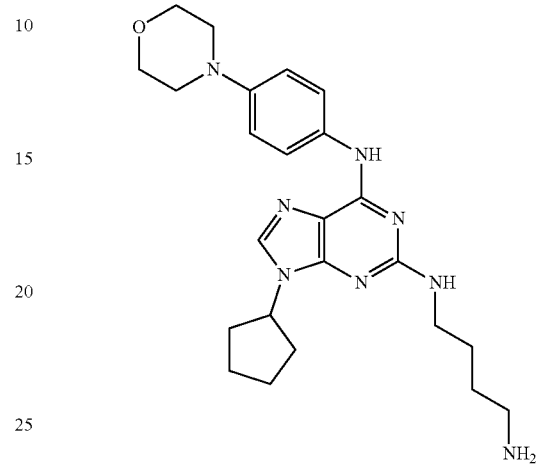

Yield: 88%. Elemental analysis: Calcd. for $C_{24}H_{34}N_8O$ (450.58): C, 63.97; H, 7.61; N, 24.87.

Found: C, 64.11; H, 7.38; N, 24.59. HPLC-MS (ESI+): 451.8 (100.0%). ¹H NMR (DMSO d-6): 1.39-1.45 (m, 2H), 1.54-1.59 (m, 2H), 1.65-1.69 (m, 2H), 1.87-2.10 (m, 6H), 2.58 (t, J=6.60, 2H), 2.97 (s(br), 2H, NH₂), 3.02-3.05 (m, 4H), 3.27 (q, J=6.36, 2H), 3.72-3.75 (m, 4H), 4.68 (qui, J=7.26, 1H), 6.86 (d, J=8.94, 2H, ArH), 7.81 (d, J=8.94, 2H, ArH), 7.85 (s, 1H, CH), 9.14 (s(br), 1H, NH).

¹³C NMR (DMSO_d₆): 23.61, 26.20, 46.03, 49.14, 66.09, 69.05, 77.07, 115.24, 121.08, 132.87, 136.10, 146.16, 152.6, 158.76, 167.19, 168.40, 185.05.

Example 14 N²-(4-amino-butyl)-9-cyclopentyl-N-[4-(4-ethyl-piperazin-1-yl)-phenyl]-9H-purine-2,6-diamine

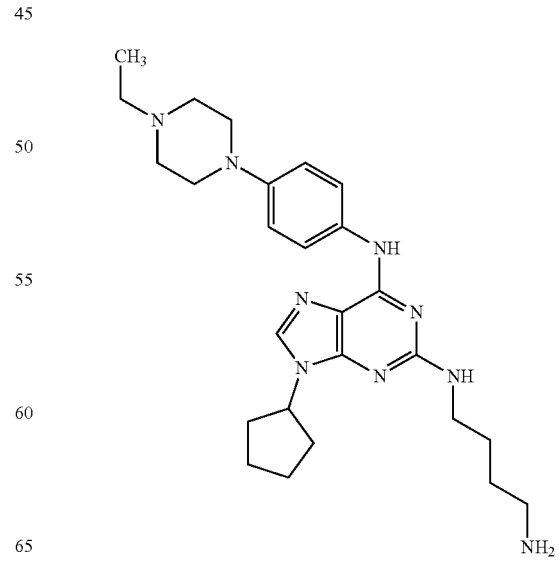

Yield: 92%. Elemental analysis: Calcd. for $C_{26}H_{39}N_9$ (477.65): C, 65.38; H, 8.23; N, 26.39.

Found: C, 65.29; H, 7.89; N, 26.39. HPLC-MS (ESI+): 478.91 (96.7%). $^1$H NMR (DMSO d-6): 1.02 (t, J=7.11, 3H), 1.38-1.42 (m, 2H), 1.51-1.57 (m, 2H), 1.63-1.68 (m, 2H), 1.85-2.09 (m, 6H), 2.35 (q, J=7.11, 2H), 2.55 (t, J=7.26, 2H), 2.98 (s(br), 2H, NH$_2$), 3.03-3.06 (m, 4H), 3.22-3.29 (m, 6H), 4.67 (qui, J=7.62, 1H), 6.52 (t, J=5.94, 1H, NH), 6.85 (d, J=8.70, 2H, ArH), 7.80 (d, J=8.70, 2H, ArH), 7.85 (s, 1H), 9.11 (s(br), 1H, NH).

$^{13}$C NMR (DMSO_d$_6$): 11.94, 23.62, 26.74, 31.69, 40.05, 46.28, 48.88, 51.56, 52.36, 54.28, 112.18, 115.43, 121.10, 132.43, 136.20, 146.23, 151.97, 158.81.

Example 15 1-Amino-3-[6-[4-(4-ethyl-piperazin-1-yl)-phenylamino]-9-cyclopentyl-9H-purin-2-ylamino]-propan-2-ol (BPA237)

Yield: 92%. Elemental analysis: Calcd. for $C_{25}H_{37}N_9O$ (479.62): C, 62.61; H, 7.78; N, 26.28.

Found: C, 62.84; H, 7.52; N, 26.12. HPLC-MS (ESI+): 479.78 (97.5%). 1.01 (t, J=6.92, 3H), 1.81-1.85 (m, 2H), 1.89-1.96 (m, 4H), 2.27-2.36 (m, 2H), 2.37 (q, J=6.92, 2H), 2.53-2.66 (m, 4H), 2.72-2.75 (m, 2H), 2.78 (s(br), 2H, NH$_2$), 3.03-3.06 (m, 4H), 3.10 (t, J=6.25, 2H), 3.18-3.22 (m, 4H), 4.02 (s(br), 1H, OH), 4.65 (qui, J=7.32, 1H), 6.94 (d, J=8.97, 2H, ArH), 7.54 (t, J=6.25, 1H, NH), 7.66 (d, J=8.97, 2H, ArH), 7.85 (s, 1H), 9.12 (s(br), 1H, NH).

Example 16 N$^2$-(4-Amino-cyclohexyl)-9-cyclopentyl-N$^6$-(4-morpholin-4-ylmethyl-phenyl)-9H-purine-2,6-diamine

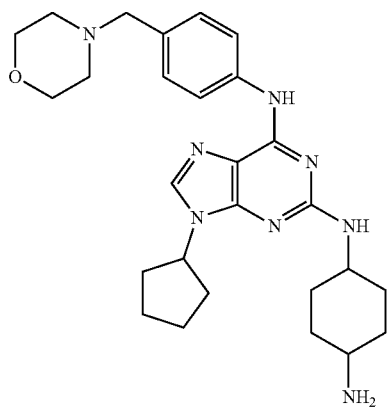 [SMILES: NC1CCC(Nc2nc(Nc3ccc(CN4CCOCC4)cc3)c3ncn(C4CCCC4)c3n2)CC1]

Yield: 94%. Elemental analysis: Calcd. for $C_{27}H_{38}N_8O$ (490.64): C, 66.09; H, 7.81; N, 22.84.

Found: C, 66.04; H, 7.59; N, 22.61. HPLC-MS (ESI+): 491.65 (98.2%). $^1$H NMR (CDCl$_3$): 1.14-1.28 (m, 4H), 1.77-1.81 (m, 2H), 1.81-1.86 (m, 4H), 1.88-1.96 (m, 4H), 2.26-2.38 (m, 2H), 2.48 (sep, J=3.65, 1H), 3.02 (s (br), 2H, NH$_2$), 3.19-3.21 (m, 4H), 3.48 (sex, J=5.25, 1H), 3.55 (s, 2H), 3.73-3.76 (m, 4H), 3.87 (m, 4H), 4.95 (qui, J=5.7, 1H), 7.64 (d, J=7.95, 2H, ArH), 7.82 (d, J=7.95, 2H, ArH), 7.91 (s, 1H, CH). $^{13}$C NMR (DMSO_d$_6$): 11.94, 23.62, 26.74, 31.69, 40.05, 46.28, 48.88, 51.56, 52.36, 54.28, 112.18, 115.43, 121.10, 132.43, 136.20, 146.23, 151.97, 158.81.

Example 17 (9-Cyclopentyl-2-morpholin-4-yl-9H-purin-6-yl)-(4-morpholin-4-ylmethyl-phenyl)-amine

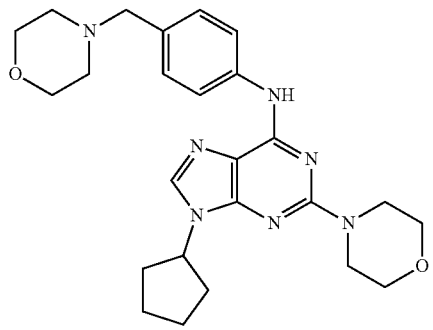 [SMILES: c1cc(Nc2nc(N3CCOCC3)nc3c2ncn3C2CCCC2)ccc1CN1CCOCC1]

Yield: 96%. Elemental analysis: Calcd. for $C_{25}H_{33}N_7O_2$ (463.58): C, 64.77; H, 7.18; N, 21.15.

Found: C, 64.69; H, 7.01; N, 21.42. HPLC-MS (ESI+): 465.69 (99.8%). $^1$H NMR (DMSO d-6): 1.02 (t, J=7.11, 3H), 1.38-1.42 (m, 2H), 1.51-1.57 (m, 2H), 1.63-1.68 (m, 2H), 1.85-2.09 (m, 6H), 2.35 (q, J=7.11, 2H), 2.55 (t, J=7.26, 2H), 2.98 (s(br), 2H, NH$_2$), 3.03-3.06 (m, 4H), 3.22-3.29 (m, 6H), 4.67 (qui, J=7.62, 1H), 6.52 (t, J=5.94, 1H, NH), 6.85 (d, J=8.70, 2H, ArH), 7.80 (d, J=8.70, 2H, ArH), 7.85 (s, 1H$_1$), 9.11 (s(br), 1H, NH).

Example 18 [9-Cyclopentyl-2-(4-methyl-piperazin-1-yl)-9H-purin-6-yl]-(4-morpholin-4-ylmethyl-phenyl)-amine

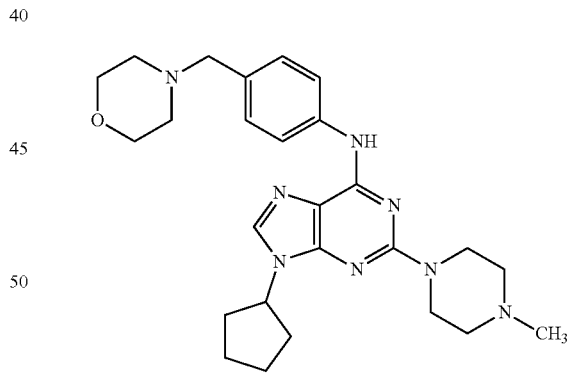

Yield: 96%. Elemental analysis: Calcd. for $C_{25}H_{33}N_7O_2$ (476.62): C, 65.52; H, 7.61; N, 23.51.

Found: C, 65.74; H, 7.92; N, 23.37. HPLC-MS (ESI+): 478.83 (99.7%). $^1$H NMR (DMSO d-6): 1.10 (s, 3H), 1.62-1.69 (m, 2H), 1.87-1.93 (m, 4H), 1.96-2.03 (m, 2H), 2.15-2.17 (m, 4H), 2.31-2.35 (m, 4H), 3.13-3.15 (m, 4H), 3.69-3.72 (m, 4H), 3.87-3.90 (m, 4H), 4.25 (s, 2H), 4.69 (qui, J=6.89, 1H), 7.31 (d, J=7.89, 2H, ArH), 7.91 (s, 1H), 8.06 (d, J=7.89, 2H, ArH).

Example 19 (9-Cyclopentyl-2-piperidin-1-yl-9H-purin-6-yl)-(4-morpholin-4-ylmethyl-phenyl)-amine

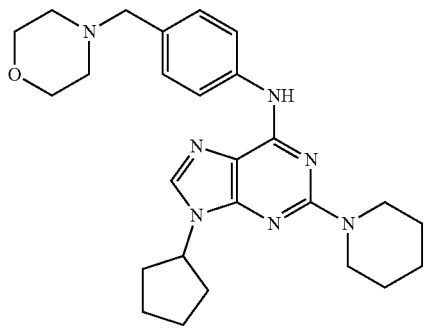 [SMILES: c1cc(Nc2nc(N3CCCCC3)nc3c2ncn3C2CCCC2)ccc1CN1CCOCC1]

Yield: 96%. Elemental analysis: Calcd. for $C_{26}H_{35}N_7O$ (461.60): C, 67.65; H, 7.64; N, 21.24.

Found: C, 67.29; H, 7.38; N, 21.03. HPLC-MS (ESI+): 463.78 (99.7%). $^1$H NMR (DMSO d-6): 1.32-1.38 (m, 2H), 1.62-1.69 (m, 2H), 1.87-1.93 (m, 4H), 1.96-2.03 (m, 2H), 2.15-2.12 (m, 8H), 2.31-2.35 (m, 4H), 3.13-3.15 (m, 4H), 3.69-3.72 (m, 4H), 4.23 (s, 2H), 4.69 (qui, J=6.75, 1H), 7.27 (d, J=8.02, 2H, ArH), 7.83 (s, 1H), 8.93 (d, J=8.02, 2H, ArH).

Example 20 $N^2$-(6-Amino-hexyl)-9-cyclopentyl-$N^6$-(4-morpholin-4-ylmethyl-phenyl)-9H-purine-2,6-diamine

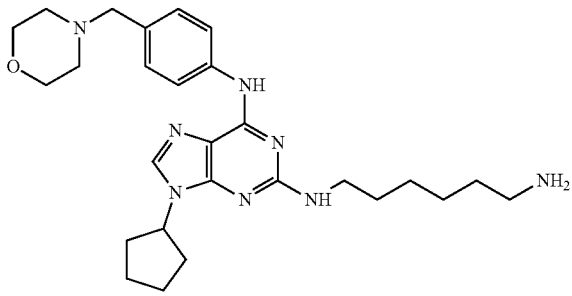 [SMILES: NCCCCCCNc1nc(Nc2ccc(CN3CCOCC3)cc2)c2ncn(C3CCCC3)c2n1]

Yield: 74%. Elemental analysis: Calcd. for $C_{27}H_{40}N_8O$ (492.66): C, 65.82; H, 8.18; N, 22.74.

Found: C, 65.96; H, 8.02; N, 22.64. HPLC-MS (ESI+): 493.93 (99.4%). $^1$H NMR (DMSO d-6): 1.25-1.34 (m, 8H), 1.51-1.57 (m, 2H), 1.63-1.70 (m, 2H), 1.87-2.09 (m, 4H), 2.31-2.35 (t, J=6.75, 2H, NH$_2$), 3.26 (q, J=6.75, 2H, CH$_2$), 3.39 (s, 2H, CH$_2$), 3.53-3.59 (m, 4H), 4.69 (qui, J=6.96, 1H, CH), 6.62 (t, J=6.18, 1H, NH), 7.17 (d, J=8.25, 2H, ArH), 7.88 (s, 1H, CH), 7.95 (d, J=8.25, 2H, ArH), 9.32 (s(br), 1H, NH).

Example 21 $N^2$-(5-Amino-pentyl)-9-cyclopentyl-$N^6$-(4-morpholin-4-ylmethyl-phenyl)-9H-purine-2,6-diamine

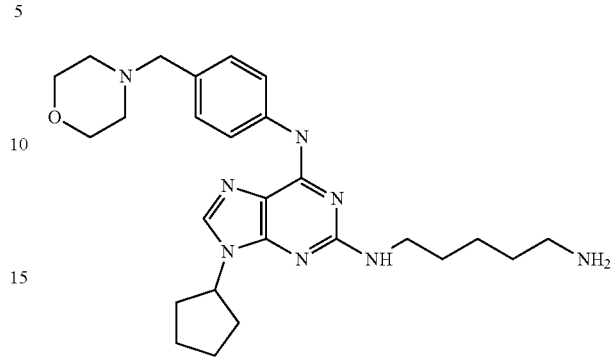

Yield: 74%. Elemental analysis: Calcd. for $C_{26}H_{38}N_8O$ (478.63): C, 65.24; H, 8.00; N, 23.14.

Found: C, 65.56; H, 8.05; N, 22.92. HPLC-MS (ESI+): 479.90 (99.7%). $^1$H NMR (DMSO-d$_6$): 1.33-1.44 (m, 4H), 1.52-1.56 (m, 2H), 1.63-1.70 (m, 2H), 1.87-2.35 (m, 8H), 2.31-2.34 (m, 4H), 2.53 (t, J=6.42, 2H, NH$_2$), 3.26 (q, J=6.42, 2H, CH$_2$), 3.40 (s, 2H, CH$_2$), 3.55-3.58 (m, 4H), 4.69 (qui, J=7.80, 1H, CH), 6.60 (t, J=4.89, 1H, NH), 7.18 (d, J=8.40, 2H, ArH), 7.88 (s, 1H, CH), 7.95 (d, J=8.40, 2H, ArH), 9.33 (s(br), 1H, NH).

Example 22 $N^2$-(4-Amino-cyclohexyl)-9-cyclopentyl-N-(6-morpholin-4-yl-pyridin-3-yl)-9H-purine-2,6-diamine

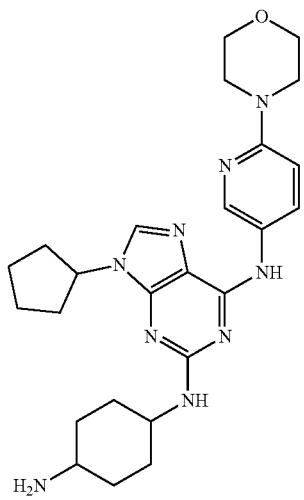 [SMILES: NC1CCC(Nc2nc(Nc3ccc(N4CCOCC4)nc3)c3ncn(C4CCCC4)c3n2)CC1]

Yield: 94%. Elemental analysis: Calcd. for $C_{25}H_{35}N_9O$ (477.61): C, 62.87; H, 7.39; N, 26.39.

Found: C, 62.61; H, 7.11; N, 26.02. HPLC-MS (ESI+): 478.57 (98.2%). $^1$H NMR (CDCl$_3$): 1.29-1.49 (m, 4H), 1.77-1.79 (m, 2H), 1.97-2.04 (m, 4H), 2.21-2.26 (m, 6H), 2.86 (sep, J=5.26, 1H), 3.14-3.18 (m, 4H), 3.83 (sex, J=4.02, 1H), 3.88-3.91 (m, 4H), 4.73 (qui, J=5.74, 1H), 4.86 (d, J=4.02, 1H, NH), 6.91 (s, 1h, ArH), 7.46-7.49 (m, 2H, ArH), 8.02 (s, 1H), 8.26 (s(br), 1H, NH).

Example 23 (9-Cyclopentyl-2-morpholin-4-yl-9H-purin-6-yl)-(6-morpholin-4-yl-pyridin-3-yl)-amine

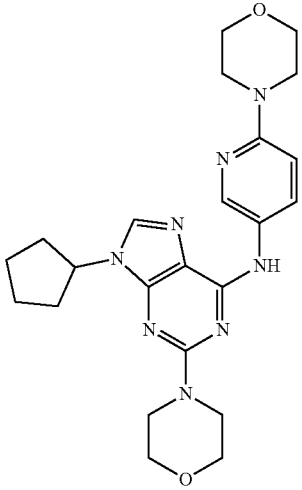 [SMILES: c1cc(N2CCOCC2)ncc1Nc1nc(N2CCOCC2)nc2c1ncn2C1CCCC1]

Yield: 87%. Elemental analysis: Calcd. for $C_{23}H_{30}N_8O$ (450.54): C, 61.31; H, 6.71; N, 24.87.

Found: C, 61.54; H, 6.48; N, 24.26. HPLC-MS (ESI+): 451.57 (97.6%). $^1$H NMR (CDCl$_3$): 1.78-1.80 (m, 2H), 1.96-2.02 (m, 4H), 2.19-2.23 (m, 2H), 3.14-3.22 (m, 8H), 3.88-3.91 (m, 4H), 4.71 (qui, J=5.26, 1H), 6.86 (s, 1H, ArH), 7.43-7.47 (m, 2H, ArH), 8.01 (s, 1H), 8.32 (s(br), 1H, NH).

Example 24 N$^2$-(4-Amino-butyl)-9-cyclopentyl-N-(4-morpholin-4-ylmethyl-phenyl)-9H-purine-2,6-diamine

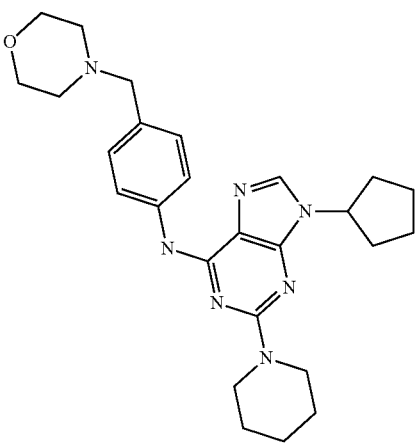 [SMILES: c1cc(Nc2nc(N3CCCCC3)nc3c2ncn3C2CCCC2)ccc1CN1CCOCC1]

Yield: 88%. Elemental analysis: Calcd. for $C_{25}H_{36}N_8O$ (464.61): C, 64.63; H, 7.81; N, 24.12.
Found: C, 64.54; H, 7.63; N, 24.00. HPLC-MS (ESI+): 465.57 (98.9%). $^1$H NMR (DMSO-d$_6$): 1.38-1.66 (m, 6H), 1.87-1.99 (m, 6H), 2.07-2.09 (m, 4H), 2.55 (t, J=6.78, 2H), 3.26 (q, J=6.39, 2H), 3.30 (s, 2H), 3.39-3.56 (m, 4H), 4.69 (qui, J=7.11, 1H), 6.64 (t, J=5.34, 1H, NH), 7.18 (d, J=8.28, 2H, ArH), 7.88 (s, 1H), 7.95 (d, J=8.28, 2H, ArH), 9.34 (s(br), 1H, NH).

Table 2. Examples of the substances prepared according to general procedures A and B of the preparation of the compounds (15).

| No | NAME OF COMPOUND | ELEMENTAL ANALYSES Calcd./Found [%] | MS (ZMD) [M − H]$^-$ | MS (ZMD) [M + H]$^+$ |
|---|---|---|---|---|
| 1 | N$^2$-(4-amino-cyclohexyl)-9-cyclopentyl-N$^6$-(4-morpholin-4-yl-phenyl)-9H-purine-2,6-diamine | C, 65.52/65.41; H, 7.61/7.36; N 23.51/23.25 | 475.64 | 477.55 |
| 2 | N$^2$-(4-amino-cyclohexyl)-9-cyclopentyl-N$^6$-(4-piperazin-1-ylmethyl-phenyl)-9H-purine-2,6-diamine | C, 66.23/66.18; H, 8.03/8.29; N, 25.74/25.65 | 488.59 | 490.62 |
| 3 | {4-[2-(4-amino-cyclohexylamino-9-cyclopentyl-9H-purin-6-ylamino]-phenyl}-(4-methyl-piperazin-1-yl)-methanone | C, 64.96/64.78; H, 7.59/7.64; N, 24.35/24.48 | 516.54 | 518.72 |
| 4 | N$^2$-(4-amino-cyclohexyl)-9-cyclopentyl-N$^6$-[6-(4-ethyl-piperazin-1-yl)-pyridin-3-yl]-9H-purine-2,6-diamine | C, 66.23/66.38; H 8.03/8.15; N, 25.74/25.62 | 488.41 | 490.78 |
| 5 | N$^2$-(4-amino-cyclohexyl)-9-cyclopentyl-N$^6$-[6-(2-oxa-6-aza-spiro[3.3]hept-6-ylmethyl)-pyridin-3-yl]-9H-purine-2,6-diamine | C, 64.39/64.21; H, 7.40/7.56; N, 25.03/25.14 | 502.43 | 505.68 |
| 6 | {5-[2-(4-amino-cyclohexylamino)-9-cyclopentyl-9H-purin-6-ylamino]-pyridin-2-yl}-(2,6-diaza-spiro[3.3]hept-2-yl)-methanone | C, 62.77/62.64; H, 7.02/7.14; N, 27.11/27.26 | 515.48 | 517.52 |
| 7 | 4-{9-cyclopentyl-6-[4-(6-methyl-2,6-diaza-spiro[3.3]hept-2-yl)-phenylamino]-9H-purin-2-ylamino}-cyclohexanol | C, 66.91/66.78; H, 7.62/7.47; N, 22.29/22.41 | 501.62 | 503.48 |
| 7 | 4-{9-cyclopentyl-6-[4-(6-methyl-2,6-diaza-spiro[3.3]hept-2-yl)-phenylamino]-9H-purin-2-ylamino}-cyclohexanol | C, 66.91/66.78; H, 7.62/7.47; N, 22.29/22.41 | 501.62 | 503.48 |
| 8 | 4-{9-cyclopentyl-6-[4-(6-ethyl-2,6-diaza-spiro[3.3]hept-2-ylmethyl)-phenylamino]-9H-purin-2-ylamino}-cyclohexanol | C, 67.90/67.74; H, 7.98/7.82; N, 21.11/21.26 | 529.81 | 531.64 |
| 9 | {4-[2-(4-hydroxy-cyclohexylamino)-9-cyclopentyl-9H-purin-6-ylamino]-phenyl}-morpholin-4-yl-methanone | C, 64.14/64.02; H 6.98/6.74; N 19.39/19.04 | 504.61 | 506.72 |
| 10 | 4-[9-cyclopentyl-6-(6-morpholin-4-yl-pyridin-3-ylamino)-9H-purin-2-ylamino]-cyclohexanol | C, 62.74/62.47; H 7.16/7.36; N 23.41/23.56 | 477.52 | 479.81 |

-continued

| No | NAME OF COMPOUND | ELEMENTAL ANALYSES Calcd./Found [%] | MS (ZMD) [M − H]⁻ | MS (ZMD) [M + H]⁺ |
|---|---|---|---|---|
| 11 | 4-[9-cyclopentyl-6-(6-morpholin-4-ylmethyl-pyridin-3-ylamino)-9H-purin-2-ylamino]-cyclohexanol | C, 63.39/63.52; H 7.37/7.36; N 22.75/23.01 | 491.58 | 493.72 |
| 12 | {5-[2-(4-hydroxy-cyclohexylamino)-9-cyclopentyl-9H-purin-6-ylamino]-pyridin-2-yl}-morpholin-4-yl-methanone | C, 61.64/61.48; H 6.76/6.48; N 22.12/22.00 | 505.61 | 507.63 |
| 13 | $N^2$-(2-amino-ethyl)-9-cyclopentyl-$N^6$-(4-morpholin-4-yl-phenyl)-9H-purine-2,6-diamine | C, 62.54/62.65; H, 7.16/7.27; N, 26.52/26.38 | 422.47 | 424.58 |
| 14 | $N^2$-(2-amino-ethyl)-9-cyclopentyl-$N^6$-(4-piperazin-1-ylmethyl-phenyl)-9H-purine-2,6-diamine | C, 63.42/63.56; H, 7.64/7.52; N, 28.94/28.79 | 434.53 | 436.33 |
| 15 | {4-[2-(2-amino-ethylamino)-9-cyclopentyl-9H-purin-6-ylamino]-phenyl}-(4-methyl-piperazin-1-yl)-methanone | C, 62.18/62.29; H, 7.18/7.31; N, 27.19/27.38 | 462.34 | 464.52 |
| 16 | $N^2$-(2-amino-ethyl)-9-cyclopentyl-$N^6$-[4-(4-ethyl-piperazin-1-yl)-pyridin-3-yl]-9H-purine-2,6-diamine | C, 61.31/61.47; H, 7.61/7.53; N, 31.09/31.19 | 449.52 | 451.63 |
| 17 | $N^2$-(2-amino-ethyl)-9-cyclopentyl-$N^6$-[6-(2-oxa-6-aza-spiro[3.3]hept-6-ylmethyl)-pyridin-3-yl]-9H-purine-2,6-diamine | C, 61.45/61.59; H, 6.95/6.78; N, 28.04/28.14 | 448.31 | 450.57 |
| 18 | {5-[2-(2-amino-ethylamino)-9-cyclopentyl-9H-purin-6-ylamino]-pyridin-2-yl}-(2,6-diaza-spiro[3.3]hept-2-yl)-methanone | C, 59.72/59.64; H, 6.54/6.37; N, 30.28/30.17 | 461.35 | 463.74 |
| 19 | $N^2$-(3-amino-propyl)-9-cyclopentyl-$N^6$-[4-(6-methyl-2,6-diaza-spiro[3.3]hept-2-yl)-phenyl]-9H-purine-2,6-diamine | C, 65.05/65.13; H, 7.64/7.52; N, 27.31/27.47 | 460.54 | 462.37 |
| 20 | $N^2$-(3-amino-propyl)-9-cyclopentyl-$N^6$-[4-(6-ethyl-2,6-diaza-spiro[3.3]hept-2-ylmethyl)-phenyl]-9H-purine-2,6-diamine | C, 66.23/66.37; H, 8.03/8.18; N, 25.74/25.63 | 488.47 | 490.55 |
| 21 | {4-[2-(3-amino-propylamino)-9-cyclopentyl-9H-purin-6-ylamino]-phenyl}-morpholin-4-yl-methanone | C, 62.05/61.98; H, 6.94/7.12; N, 24.12/24.32 | 463.64 | 465.71 |
| 22 | $N^2$-(3-amino-propyl)-9-cyclopentyl-$N^6$-(6-morpholin-4-yl-pyridin-3-yl)-9H-purine-2,6-diamine | C, 60.39/60.59; H, 7.14/7.28; N, 28.81/29.02 | 436.50 | 438.49 |
| 23 | $N^2$-(3-amino-propyl)-9-cyclopentyl-$N^6$-(6-morpholin-4-ylmethyl-pyridin-3-yl-9H-purine-2,6-diamine | C, 61.18/61.41; H, 7.37/7.20; N, 27.92/27.74 | 450.60 | 452.49 |
| 24 | {5-[2-(3-amino-propylamino)-9-cyclopentyl-9H-purin-6-ylamino]-pyridin-2-yl}-morpholin-4-yl-methanone | C, 59.34/59.17; H, 6.71/6.54; N, 27.08/27.19 | 464.23 | 466.39 |
| 25 | $N^2$-(4-amino-butyl)-9-cyclopentyl-$N^6$-(4-piperazin-1-yl-phenyl)-9H-purine-2,6-diamine | C, 64.11/64.21; H, 7.85/7.73; N, 28.04/28.18 | 448.61 | 450.76 |
| 26 | $N^2$-(4-amino-butyl)-9-cyclopentyl-$N^6$-[4-(4-methyl-piperazin-1-ylmethyl)-phenyl]-9H-purine-2,6-diamine | C, 65.38/65.44; H, 8.23/8.37; N 26.39/26.47 | 476.53 | 478.74 |
| 27 | {4-[2-(4-amino-butylamino)-9-cyclopentyl-9H-purin-6-ylamino]-phenyl}-(4-methyl-piperazin-1-yl)-methanone | C, 63.52/63.74; H, 7.59/7.41; N, 25.64/25.44 | 490.61 | 492.55 |
| 28 | $N^2$-(4-amino-butyl)-9-cyclopentyl-$N^6$-[6-(2-oxa-6-aza-spiro[3.3]hept-6-yl)-pyridin-3-yl]-9H-purine-2,6-diamine | C, 62.18/62.22; H, 7.18/7.31; N, 27.19/27.32 | 462.58 | 464.71 |
| 29 | $N^2$-(4-amino-butyl)-9-cyclopentyl-$N^6$-[6-(2-oxa-6-aza-spiro[3.3]hept-6-ylmethyl)-pyridin-3-yl]-9H-purine-2,6-diamine | C, 62.87/62.72; H, 7.39/7.44; N, 26.39/26.51 | 476.67 | 478.74 |
| 30 | {5-[2-(4-amino-butylamino)-9-cyclopentyl-9H-purin-6-ylamino]-pyridin-2-yl}-(2,6-diaza-spiro[3.3]hept-2-yl)-methanone | C, 61.20/61.35; H, 6.99/6.82; N, 28.55/28.42 | 489.52 | 491.48 |
| 31 | $N^2$-(5-amino-pentyl)-9-cyclopentyl-$N^6$-[4-(2,6-diaza-spiro[3.3]hept-2-yl)-phenyl]-9H-purine-2,6-diamine | C, 65.66/65.47; H, 7.84/7.71; N, 26.50/26.43 | 474.67 | 476.51 |
| 32 | $N^2$-(5-amino-pentyl)-9-cyclopentyl-$N^6$-[4-(6-methyl-2,6-diaza-spiro[3.3]hept-2-ylmethyl)-phenyl]-9H-purine-2,6-diamine | C, 66.77/66.62; H, 8.20/8.37; N, 25.03/25.11 | 502.78 | 504.56 |
| 33 | {4-[2-(5-amino-pentylamino)-9-cyclopentyl-9H-purin-6-ylamino]-phenyl}-(6-ethyl-2,6-diaza-spiro[3.3]hept-2-yl)-methanone | C, 65.51/65.42; H, 7.77/7.64; N, 23.71/23.58 | 530.66 | 532.89 |
| 34 | $N^2$-(5-amino-pentyl)-9-cyclopentyl-$N^6$-(6-morpholin-4-yl-pyridin-3-yl)-9H-purine-2,6-diamine | C, 61.91/62.11; H, 7.58/7.63; N, 27.07/27.39 | 464.61 | 466.72 |
| 35 | $N^2$-(5-amino-pentyl)-9-cyclopentyl-$N^6$-(6-morpholin-4-ylmethyl-pyridin-3-yl-9H-purine-2,6-diamine | C, 62.61/62.41; H, 7.78/7.49; N, 26.28/26.18 | 478.53 | 480.54 |
| 36 | {5-[2-(5-amino-pentylamino)-9-cyclopentyl-9H-purin-6-ylamino]-pyridin-2-yl}-morpholin-4-yl-methanone | C, 60.83/60.94; 7.15/6.92; 25.54/25.74 | 492.58 | 494.59 |
| 37 | $N^2$-(6-amino-hexyl)-9-cyclopentyl-$N^6$-(4-morpholin-4-yl-phenyl)-9H-purine-2,6-diamine | C, 65.24/64.99; 8.00/7.87; 23.41/23.09 | 477.63 | 479.52 |
| 38 | $N^2$-(6-amino-hexyl)-9-cyclopentyl-$N^6$-(4-morpholin-4-ylmethyl-phenyl)-9H-purine-2,6-diamine | C, 65.82/65.68; H, 8.18/8.25; N, 22.74/22.58 | 491.55 | 493.73 |
| 39 | {4-[2-(6-amino-hexylamino)-9-cyclopentyl-9H-purin-6-ylamino]-phenyl}-piperazin-1-yl-methanone | C, 64.13/64.25; H, 7.77/7.63; N, 24.93/24.82 | 504.88 | 506.67 |
| 40 | $N^2$-(6-amino-hexyl)-9-cyclopentyl-$N^6$-[6-(4-methyl-piperazin-1-yl)-pyridin-3-yl]-9H-purine-2,6-diamine | C, 63.39/63.24; H, 8.18/8.27; N, 28.43/28.55 | 491.59 | 493.75 |

-continued

| No | NAME OF COMPOUND | ELEMENTAL ANALYSES Calcd./Found [%] | MS (ZMD) [M − H]⁻ | MS (ZMD) [M + H]⁺ |
|---|---|---|---|---|
| 41 | N²-(6-amino-hexyl)-9-cyclopentyl-N⁶-[6-(4-ethyl-piperazin-1-ylmethyl)-pyridin-3-yl]-9H-purine-2,6-diamine | C, 64.58/64.41; H, 8.52/8.64; N, 26.90/26.79 | 519.65 | 521.76 |
| 42 | {5-[2-(6-amino-hexylamino)-9-cyclopentyl-9H-purin-6-ylamino]-pyridin-2-yl}-(2,6-diaza-spiro[3.3]hept-2-yl)-methanone | C, 62.52/62.37; H, 7.38/7.46; N, 27.01/27.17 | 517.54 | 519.63 |
| 43 | (9-cyclopentyl-2-morpholin-4-yl-9H-purin-6-yl)-[4-(6-methyl-2,6-diaza-spiro[3.3]hept-2-yl)-phenyl]-amine | C, 65.80/65.67; H, 7.22/7.34; N, 23.61/23.48 | 473.72 | 475.49 |
| 44 | (9-cyclopentyl-2-morpholin-4-yl-9H-purin-6-yl)-(4-morpholin-4-ylmethyl-phenyl)-amine | C, 64.77/64.69; H, 7.18/7.01; N, 21.15/21.42 | 463.71 | 465.69 |
| 45 | [4-(9-Cyclopentyl-2-morpholin-4-yl-9H-purin-6-ylamino)-phenyl]-morpholin-4-yl-methanone | C, 62.88/62.74; H 6.54/6.76; N 20.53/20.14 | 476.51 | 478.62 |
| 46 | (9-cyclopentyl-2-morpholin-4-yl-9H-purin-6-yl)-(6-morpholin-4-yl-pyridin-3-yl)-amine | C, 61.31/61.54; H, 6.71/6.48; N, 24.87/24.26 | 449.49 | 451.57 |
| 47 | (9-Cyclopentyl-2-morpholin-4-yl-9H-purin-6-yl)-(6-morpholin-4-ylmethyl-pyridin-3-yl)-amine | C, 62.05/62.12; H, 6.94/6.78; N, 24.12/24.23 | 463.67 | 465.61 |
| 48 | [5-(9-Cyclopentyl-2-morpholin-4-yl-9H-purin-6-ylamino)-pyridin-2-yl]-piperazin-1-yl-methanone | C, 60.36/60.45; H, 6.54/6.48; N, 26.40/26.55 | 476.42 | 478.51 |
| 49 | 9-cyclopentyl-2-piperazin-1-yl-9H-purin-6-yl)-[4-(4-methyl-piperazin-1-yl)-phenyl]-amine | C, 65.05/65.21; H, 7.64/7.52; N, 27.31/27.43 | 460.72 | 462.57 |
| 50 | (9-Cyclopentyl-2-piperazin-1-yl-9H-purin-6-yl)-[4-(2-oxa-6-aza-spiro[3.3]hept-6-ylmethyl)-phenyl]-amine | C, 65.80/65.69; H, 7.22/7.14; N, 23.61/23.48 | 473.49 | 475.52 |
| 51 | [4-(9-Cyclopentyl-2-piperazin-1-yl-9H-purin-6-ylamino)-phenyl]-(6-methyl-2,6-diaza-spiro[3.3]hept-2-yl)-methanone | C, 64.65/64.53; H, 7.03/7.18; N, 25.13/25.28; | 500.57 | 502.53 |
| 52 | (9-Cyclopentyl-2-piperazin-1-yl-9H-purin-6-yl)-[6-(2,6-diaza-spiro[3.3]hept-2-yl)-pyridin-3-yl]-amine | C, 62.59/62.44; H, 7.00/7.11; N, 30.41/30.28 | 459.61 | 461.55 |
| 53 | (9-Cyclopentyl-2-piperazin-1-yl-9H-purin-6-yl)-[6-(6-methyl-2,6-diaza-spiro[3.3]hept-2-ylmethyl)-pyridin-3-yl]-amine | C, 63.91/63.83; H, 7.43/7.57; N, 28.67/28.79 | 487.71 | 489.55 |
| 54 | [5-(9-Cyclopentyl-2-piperazin-1-yl-9H-purin-6-ylamino)-pyridin-2-yl]-(6-ethyl-2,6-diaza-spiro[3.3]hept-2-yl)-methanone | C, 62.77/62.83; H, 7.02/7.17; N, 27.11/27.23 | 515.72 | 517.61 |
| 55 | [9-cyclopentyl-2-(4-methyl-piperazin-1-yl)-9H-purin-6-yl]-(4-morpholin-4-yl-phenyl)-amine | C, 64.91/65.12; H, 7.41/7.50; N 24.22/24.56 | 461.60 | 463.58 |
| 56 | [9-cyclopentyl-2-(4-methyl-piperazin-1-yl)-9H-purin-6-yl]-(4-morpholin-4-ylmethyl-phenyl)-amine | C, 65.52/65.74; H, 7.61/7.92; N, 23.51/23.37 | 476.91 | 478.83 |
| 57 | {4-[9-Cyclopentyl-2-(4-methyl-piperazin-1-yl)-9H-purin-6-ylamino]-phenyl}-morpholin-4-yl-methanone | C, 63.65/63.58; H, 6.99/6.83; N, 22.84/22.73 | 489.72 | 491.49 |
| 58 | [9-cyclopentyl-2-(4-methyl-piperazin-1-yl)-9H-purine-6-yl]-(6-piperazin-1-yl-pyridin-3-yl)-amine | C, 62.31/62.43; H, 7.41/7.53; N, 30.28/30.37 | 461.48 | 463.53 |
| 59 | [9-Cyclopentyl-2-(4-methyl-piperazin-1-yl)-9H-purin-6-yl]-[6-(4-methyl-piperazin-1-ylmethyl)-pyridin-3-yl]-amine | C, 63.65/63.57; H, 7.81/7.92; N, 28.55/28.69 | 489.74 | 491.71 |
| 60 | {5-[9-Cyclopentyl-2-(4-methyl-piperazin-1-yl)-9H-purin-6-ylamino]-pyridin-2-yl}-(4-ethyl-piperazin-1-yl)-methanone | C, 62.52/62.43; H, 7.38/7.52; N, 27.01/27.20 | 517.57 | 519.54 |
| 61 | (9-cyclopentyl-2-piperidin-1-yl-9H-purin-6-yl)-[4-(2-oxa-6-aza-spiro[3.3]hept-6-yl)-phenyl]-amine | C, 67.95/67.82; H, 7.24/7.37; N, 21.33/21.50 | 458.51 | 460.63 |
| 62 | (9-Cyclopentyl-2-piperidin-1-yl-9H-purin-6-yl)-[4-(6-methyl-2,6-diaza-spiro[3.3]hept-2-ylmethyl)-phenyl]-amine | C, 69.10/69.32; H, 7.87/7.94; N, 23.03/23.24 | 485.59 | 487.73 |
| 63 | [4-(9-Cyclopentyl-2-piperidin-1-yl-9H-purin-6-ylamino)-phenyl]-morpholin-4-yl-methanone | C, 65.66/65.42; H 6.99/6.71; 20.62/20.87 | 474.60 | 476.52 |
| 64 | (9-Cyclopentyl-2-piperidin-1-yl-9H-purin-6-yl)-[6-(6-methyl-2,6-diaza-spiro[3.3]hept-2-yl)-pyridin-3-yl]-amine | C, 65.93/65.78; H, 7.45/7.61; N, 26.62/26.74 | 472.56 | 474.67 |
| 65 | (9-Cyclopentyl-2-piperidin-1-yl-9H-purin-6-yl)-[6-(6-ethyl-2,6-diaza-spiro[3.3]hept-2-ylmethyl)-pyridin-3-yl]-amine | C, 67.04/67.21; H, 7.84/7.93; N, 25.13/25.02 | 500.64 | 502.84 |
| 66 | [5-(9-Cyclopentyl-2-piperidin-1-yl-9H-purin-6-ylamino)-pyridin-2-yl]-morpholin-4-yl-methanone | C, 63.01/62.87; 6.77/6.45; 23.51/23.11 | 475.61 | 477.63 |
| 67 | 1-{9-cyclopentyl-6-[4-(4-ethyl-piperazin-1-yl)-phenylamino]-9H-purin-2-ylamino}-propan-2-ol | C, 62.61/62.84; H, 7.78/7.52; N, 26.28/26.12 | 477.76 | 479.78 |
| 68 | 1-[9-cyclopentyl-6-(4-morpholin-4-ylmethyl-phenylamino)-9H-purin-2-ylamino]-propan-2-ol | C, 63.84/63.78; H, 7.37/7.29; N, 21.71/21.67 | 450.49 | 452.63 |
| 69 | {1-[2-(2-hydroxy-propylamino)-9-cyclopentyl-9H-purin-6-ylamino]-phenyl}-piperazin-1-yl-methanone | C, 62.05/62.14; H, 6.94/6.87; N, 24.12/24.23 | 463.51 | 465.71 |
| 70 | 1-{9-cyclopentyl-6-[6-(4-methyl-piperazin-1-yl)-pyridin-3-ylamino]-9H-purin-2-ylamino}-propan-2-ol | C, 61.17/61.31; H, 7.37/7.52; N, 27.92/27.71 | 450.41 | 452.63 |
| 71 | 1-{9-cyclopentyl-6-[6-(4-ethyl-piperazin-1-ylmethyl)-pyridin-3-ylamino]-9H-purin-2-ylamino}-propan-2-ol | C, 62.61/62.83; H, 7.78/7.65; N, 26.28/26.41 | 478.69 | 480.55 |

-continued

| No | NAME OF COMPOUND | ELEMENTAL ANALYSES Calcd./Found [%] | MS (ZMD) [M − H]⁻ | [M + H]⁺ |
|---|---|---|---|---|
| 72 | {5-[2-(2-hydroxy-propylamino)-9-cyclopentyl-9H-purin-6-ylamino]-pyridin-2-yl}-(2,6-diaza-spiro[3.3]hept-2-yl)-methanone | C, 60.36/60.22; H, 6.54/6.72; N, 26.40/26.63 | 476.44 | 478.71 |
| 73 | 2-{9-cyclopentyl-6-[4-(2-oxa-6-aza-spiro[3.3]hept-6-yl)-phenylamino]-9H-purin-2-ylamino}-butan-1-ol | C, 64.77/64.56; H, 7.18/7.24; N, 21.15/21.34 | 462.63 | 464.49 |
| 74 | 2-{9-cyclopentyl-6-[4-(6-methyl-2,6-diaza-spiro[3.3]hept-2-ylmethyl)-phenylamino]-9H-purin-2-ylamino}-butan-1-ol | C, 66.09/66.24; H, 7.81/7.97; N, 22.84/22.73 | 489.51 | 491.57 |
| 75 | {4-[2-(1-hydroxymethyl-propylamino)-9-cyclopentyl-9H-purin-6-ylamino]-phenyl}-(6-ethyl-2,6-diaza-spiro[3.3]hept-2-yl)-methanone | C, 66.09/65.82; H, 7.81/8.06; N, 22.84/22.51 | 489.60 | 491.72 |
| 76 | 2-[9-cyclopentyl-6-(6-morpholin-4-yl-pyridin-3-ylamino)-9H-purin-2-ylamino]-butan-1-ol | C, 61.04/61.32; H 7.13/6.99; N 24.76/24.55 | 451.62 | 453.55 |
| 77 | 2-[9-cyclopentyl-6-(6-morpholin-4-ylmethyl-pyridin-3-ylamino)-9H-purin-2-ylamino]-butan-1-ol | C, 61.78/61.42; H, 7.34/7.52; N 24.02/23.74 | 465.51 | 467.63 |
| 78 | {5-[2-(1-hydroxymethyl-propylamino)-9-cyclopentyl-9H-purin-6-ylamino]-pyridin-2-yl}-morpholin-4-yl-methanone | C, 59.98/59.85; H 6.71/7.11; N 23.32/23.02 | 479.55 | 481.63 |
| 79 | (9-cyclopentyl-2-pyrrolidin-1-yl-9H-purin-6-yl)-(4-morpholin-4-yl-phenyl)-amine | C, 66.49/66.62; H, 7.21/7.39; N, 22.61/22.82; O, 3.69/3.81 | 432.53 | 434.72 |
| 80 | (9-cyclopentyl-2-pyrrolidin-1-yl-9H-purin-6-yl)-[4-(4-methyl-piperazin-1-ylmethyl)-phenyl]-amine | C, 67.80/67.61; H, 7.88/7.64; N, 24.33/24.41 | 459.73 | 461.67 |
| 81 | [4-(9-cyclopentyl-2-pyrrolidin-1-yl-9H-purin-6-ylamino)-phenyl]-(2-oxa-6-aza-spiro[3.3]hept-6-yl)-methanone | C, 65.94/65.73; H, 6.60/6.43; N, 20.70/20.56; O, 6.76/6.53 | 472.44 | 474.63 |
| 82 | (9-cyclopentyl-2-pyrrolidin-1-yl-9H-purin-6-yl)-[6-(4-ethyl-piperazin-1-yl)-pyridin-3-yl]-amine | C, 65.05/65.23; H, 7.64/7.41; N, 27.31/27.16 | 460.52 | 462.74 |
| 83 | (9-cyclopentyl-2-pyrrolidin-1-yl-9H-purin-6-yl)-[6-(4-ethyl-piperazin-1-ylmethyl)-pyridin-3-yl]-amine | C, 65.66/65.78; H, 7.84/7.67; N, 26.50/26.39 | 474.40 | 476.53 |
| 84 | [5-(9-cyclopentyl-2-pyrrolidin-1-yl-9H-purin-6-ylamino)-pyridin-2-yl]-(4-ethyl-piperazin-1-yl)-methanone | C, 63.78/63.62; H, 7.21/7.37; N, 25.75/25.89; O, 3.27/3.43 | 488.54 | 490.77 |
| 85 | 2-{9-cyclopentyl-6-[4-(2,6-diaza-spiro[3.3]hept-2-yl)-phenylamino]-9H-purin-2-ylamino}-cyclopentanol | C, 65.80/65.67; H, 7.22/7.38; N, 23.61/23.79; O, 3.37/3.51 | 473.48 | 475.72 |
| 86 | 2-{9-cyclopentyl-6-[4-(2,6-diaza-spiro[3.3]hept-2-ylmethyl)-phenylamino]-9H-purin-2-ylamino}-cyclopentanol | C, 66.37/66.21; H, 7.43/7.57; N, 22.93/22.78; O, 3.27/3.15 | 487.71 | 489.52 |
| 87 | {4-[9-cyclopentyl-2-(2-hydroxy-cyclopentylamino)-9H-purin-6-ylamino]-phenyl}-(6-methyl-2,6-diaza-spiro[3.3]hept-2-yl)-methanone | C, 65.09/65.21; H, 7.02/7.18; N, 21.69/21.82; O, 6.19/6.31 | 515.69 | 517.71 |
| 88 | 2-[9-cyclopentyl-6-(6-morpholin-4-yl-pyridin-3-ylamino)-9H-purin-2-ylamino]-cyclopentanol | C, 62.05/62.36; H 6.94/6.78; N 24.12/24.02 | 463.55 | 465.63 |
| 89 | 2-[9-cyclopentyl-6-(6-morpholin-4-ylmethyl-pyridin-3-ylamino)-9H-purin-2-ylamino]-cyclopentanol | C, 62.74/62.41; H 7.16/6.99; N23.41/23.66 | 477.60 | 479.62 |
| 90 | {5-[9-cyclopentyl-2-(2-hydroxy-cyclopentylamino)-9H-purin-6-ylamino]-pyridin-2-yl}-morpholin-4-yl-methanone | C, 60.96/60.81; H, 6.55/6.43; N, 22.75/22.88; O, 9.74/9.62 | 491.43 | 493.49 |
| 91 | 3-[9-cyclopentyl-6-(4-piperazin-1-yl-phenylamino)-9H-purin-2-ylamino]-cyclopentanol | C, 64.91/64.78; H, 7.41/7.33; N, 24.22/24.41; O, 3.46/3.59 | 461.47 | 463.65 |
| 92 | 3-{9-cyclopentyl-6-[4-(4-methyl-piperazin-1-ylmethyl)-phenylamino]-9H-purin-2-ylamino}-cyclopentanol | C, 66.09/66.18; H, 7.81/7.95; N, 22.84/22.67; O, 3.26/3.18 | 489.58 | 491.73 |
| 93 | {4-[9-cyclopentyl-2-(3-hydroxy-cyclopentylamino)-9H-purin-6-ylamino]-phenyl}-(4-ethyl-piperazin-1-yl)-methanone | C, 64.84/64.93; H, 7.38/7.22; N, 21.60/21.48; O, 6.17/6.26 | 517.55 | 519.74 |
| 94 | 3-{9-cyclopentyl-6-[6-(2,6-diaza-spiro[3.3]hept-2-yl)-pyridin-3-ylamino]-9H-purin-2-ylamino}-cyclopentanol | C, 63.14/63.23; H, 6.99/6.73; N, 26.51/26.43; O, 3.36/3.54 | 474.52 | 476.55 |
| 95 | 3-{9-cyclopentyl-6-[6-(6-methyl-2,6-diaza-spiro[3.3]hept-2-ylmethyl)-pyridin-3-ylaminoamino]-9H-purin-2-ylamino}-cyclopentanol | C, 64.39/64.27; H, 7.40/7.59; N, 25.03/25.17; O, 3.18/3.27 | 502.74 | 504.57 |
| 96 | {5-[9-cyclopentyl-2-(3-hydroxy-cyclopentylamino)-9H-purin-6-ylamino]-pyridin-2-yl}-(6-ethyl-2,6-diaza-spiro[3.3]hept-2-yl)-methanone | C, 63.26/63.34; H, 7.01/7.23; N, 23.71/23.54 | 530.53 | 532.59 |
| 97 | {1-[9-cyclopentyl-6-(4-morpholin-4-yl-phenylamino)-9H-purine-2-yl]-piperidin-2-yl}-methanol; | C, 65.39/65.19; H, 7.39/7.15; N, 20.53/20.64 | 476.61 | 478.62 |
| 98 | {1-[9-cyclopentyl-6-(4-morpholin-4-ylmethyl-phenylamino)-9H-purine-2-yl]-piperidin-2-yl}-methanol | C, 65.96/65.82; H 7.59/7.25; N, 19.94/20.12 | 490.52 | 492.82 |

-continued

| No | NAME OF COMPOUND | ELEMENTAL ANALYSES Calcd./Found [%] | MS (ZMD) [M − H]⁻ | [M + H]⁺ |
|---|---|---|---|---|
| 99 | {4-[9-cyclopentyl-2-(2-hydroxymethyl-piperidin-1-yl)-9H-purine-6-ylamino]-phenyl}-morpholin-4-yl-methanone | C, 64.14/64.12; H 6.98/7.12; N, 19.39/19.52 | 504.72 | 506.75 |
| 100 | {1-[9-cyclopentyl-6-(6-morpholin-4-yl-pyridin-3-ylamino)-9H-purine-2-yl]-piperidin-2-yl}-methanol | C, 62.74/62.65; H, 7.16/7.27; N, 23.41/23.57 | 477.51 | 479.67 |
| 101 | {1-[9-cyclopentyl-6-(6-piperazin-1-ylmethyl-pyridin-3-ylamino)-9H-purine-2-yl]-piperidin-2-yl}-methanol | C, 63.52/63.43; H, 7.59/7.48; N, 25.64/25.49 | 490.59 | 492.73 |
| 102 | {5-[9-cyclopentyl-2-(2-hydroxymethyl-piperidin-1-yl)-9H-purine-6-ylamino]-pyridin-2-yl}-(4-ethyl-piperazin-1-yl)-methanone | C, 63.02/63.17; H, 7.37/7.43; N, 23.62/23.54 | 532.59 | 534.71 |
| 103 | 2-(1-{9-cyclopentyl-6-[4-(2,6-diaza-spiro[3.3]hept-2-yl)-phenylamino]-9H-purine-2-yl}-piperidin-2-yl)-ethanol | C, 66.90/66.82; H, 7.62/7.74; N, 22.29/22.41 | 501.69 | 503.54 |
| 104 | 2-{1-[9-cyclopentyl-6-(4-morpholin-4-ylmethyl-phenylamino)-9H-purine-2-yl]-piperidin-2-yl}-ethanol | C, 66.51/66.82; H 7.77/7.52; N, 19.39/19.22 | 504.63 | 506.71 |
| 105 | (4-{9-cyclopentyl-2-[2-(2-hydroxy-ethyl)-piperidin-1-yl]-9H-purine-6-ylamino}-phenyl)-morpholin-4-yl-methanone | C, 64.72/64.98; H, 7.18/7.32; N 18.87/18.95 | 518.45 | 520.74 |
| 106 | 2-{1-[9-cyclopentyl-6-(6-morpholin-4-yl-pyridin-3-ylamino)-9H-purine-2-yl]-piperidin-2-yl}-ethanol | C, 63.39/63.58; H, 7.37/7.54; N, 22.75/22.46 | 491.63 | 493.62 |
| 107 | 2-{1-[9-cyclopentyl-6-(6-morpholin-4-ylmethyl-pyridin-3-ylamino)-9H-purine-2-yl]-piperidin-2-yl}-ethanol | C, 64.01/64.13; H, 7.56/7.43; N, 22.12/22.09 | 505.57 | 507.62 |
| 108 | (5-{9-cyclopentyl-2-[2-(2-hydroxy-ethyl)-piperidin-1-yl]-9H-purine-6-ylamino}-pyridin-2-yl)-piperazin-1-yl-methanone | C, 62.41/62.55; H, 7.18/7.29; N, 24.26/24.17 | 518.59 | 520.61 |
| 109 | 2-{9-cyclopentyl-6-[4-(4-methyl-piperazin-1-yl)-phenylamino]-9H-purin-2-ylamino}-ethanol | C, 63.26/63.37; H, 7.39/7.45; N, 25.67/25.59 | 435.48 | 437.61 |
| 110 | 2-{9-cyclopentyl-6-[4-(2-oxa-6-aza-spiro[3.3]hept-6-ylmethyl)-phenylamino]-9H-purin-2-ylamino}-ethanol | C, 64.12/64.23; H, 6.95/6.73; N,21.81/21.75 | 448.61 | 450.66 |
| 111 | {4-[9-cyclopentyl-2-(2-hydroxy-ethylamino)-9H-purine-6-ylamino]-phenyl}-(2,6-diaza-spiro[3.3]hept-2-yl)-methanone | C, 62.32/62.45; H, 6.54/6.42; N, 24.23/24.50 | 461.51 | 463.60 |
| 112 | 2-[9-cyclopentyl-6-(6-morpholin-4-yl-pyridin-3-ylamino)-9H-purin-2-ylamino]-ethanol | C, 59.42/59.12; H, 6.24/6.55; N 26.40/26.12 | 423.50 | 425.52 |
| 113 | 2-[9-cyclopentyl-6-(6-morpholin-4-ylmethyl-pyridin-3-ylamino)-9H-purin-2-ylamino]-ethanol | C, 60.26/59.85; H, 6.24/6.25; N, 24.76/24.55 | 437.50 | 439.52 |
| 114 | {5-[9-cyclopentyl-2-(2-hydroxy-ethylamino)-9H-purine-6-ylamino]-pyridin-2-yl}-morpholin-4-yl-methanone | C, 58.39/58.69; H, 6.24/6.53; N, 24.76/24.63 | 451.62 | 453.52 |
| 115 | 3-[9-cyclopentyl-6-(4-morpholin-4-yl-phenylamino)-9H-purin-2-ylamino]-propan-1-ol | C, 63.14/62.88; H, 7.14/6.95; N, 22.41/22.13 | 436.52 | 438.62 |
| 116 | 3-[9-cyclopentyl-6-(4-morpholin-4-ylmethyl-phenylamino)-9H-purin-2-ylamino]-propan-1-ol | C, 63.84/63.56; H, 7.37/3.18; N 21.71/21.95 | 450.55 | 452.62 |
| 117 | {4-[9-cyclopentyl-2-(3-hydroxy-propylamino)-9H-purine-6-ylamino]-phenyl}-morpholin-4-yl-methanone | C, 61.92/61.78; H, 6.71/6.93; N, 21.06/21.22 | 464.59 | 466.48 |
| 118 | 3-[9-cyclopentyl-6-(6-piperazin-1-yl-pyridin-3-ylamino)-9H-purin-2-ylamino]-propan-1-ol | C, 60.39/60.22; H, 7.14/7.31; N, 28.81/28.66 | 436.41 | 438.67 |
| 119 | 3-{9-cyclopentyl-6-[6-(4-methyl-piperazin-1-ylmethyl)-pyridin-3-ylamino]-9H-purin-2-ylamino}-propan-1-ol | C, 61.91/61.78; H, 7.58/7.44; N, 27.08/27.24 | 464.52 | 466.63 |
| 120 | {5-[9-cyclopentyl-2-(3-hydroxy-propylamino)-9H-purine-6-ylamino]-pyridin-2-yl}-(4-ethyl-piperazin-1-yl)-methanone | C, 60.83/60.72; H, 7.15/7.29; N, 25.54/25.43 | 492.69 | 494.55 |
| 121 | 3-{9-cyclopentyl-6-[4-(2-oxa-6-aza-spiro[3.3]hept-6-yl)-phenylamino]-9H-purin-2-ylamino}-butan-1-ol | C, 64.77/64.56; H, 7.18/7.26; N, 21.15/21.24 | 464.47 | 462.58 |
| 122 | 3-{9-cyclopentyl-6-[4-(2-oxa-6-aza-spiro[3.3]hept-6-ylmethyl)-phenylamino]-9H-purin-2-ylamino}-butan-1-ol | C, 65.39/65.12; H, 7.39/7.26; N, 20.53/20.78 | 476.12 | 478.71 |
| 123 | {4-[9-cyclopentyl-2-(4-hydroxy-butylamino)-9H-purine-6-ylamino]-phenyl}-(6-methyl-2,6-diaza-spiro[3.3]hept-2-yl)-methanone | C, 64.26/64.34; H, 7.19/7.25; N, 22.21/22.36 | 503.55 | 505.74 |
| 124 | 4-{9-cyclopentyl-6-[6-(6-ethyl-2,6-diaza-spiro[3.3]hept-2-yl)-pyridin-3-ylamino]-9H-purin-2-ylamino}-butan-1-ol | C, 63.52/63.48; H, 7.19/7.26; N, 25.64/25.48 | 490.51 | 492.60 |
| 125 | 4-{9-cyclopentyl-6-[6-(6-ethyl-2,6-diaza-spiro[3.3]hept-2-ylmethyl)-pyridin-3-ylamino]-9H-purin-2-ylamino}-butan-1-ol | C, 64.13/64.22; H, 7.77/7.63; N, 24.93/24.72 | 504.73 | 506.64 |
| 126 | {5-[9-cyclopentyl-2-(4-hydroxy-butylamino)-9H-purine-6-ylamino]-pyridin-2-yl}-morpholin-4-yl-methanone | C, 59.98/60.10; H 6.71/6.55; N, 23.32/23.51 | 479.55 | 481.54 |
| 127 | 5-[9-cyclopentyl-6-(4-morpholin-4-yl-phenylamino)-9H-purin-2-ylamino]-pentan-1-ol | C, 64.49/64.55; H, 7.58/7.70; N, 21.06/20.85 | 464.60 | 466.62 |

-continued

| No | NAME OF COMPOUND | ELEMENTAL ANALYSES Calcd./Found [%] | MS (ZMD) [M − H]⁻ | [M + H]⁺ |
|---|---|---|---|---|
| 128 | 5-[9-cyclopentyl-6-(4-morpholin-4-ylmethyl-phenylamino)-9H-purin-2-ylamino]-pentan-1-ol | C, 65.11/65.27; H, 7.78/7.64; N, 20.44/20.59 | 478.54 | 480.55 |
| 129 | {4-[9-cyclopentyl-2-(5-hydroxy-pentylamino)-9H-purin-6-ylamino]-phenyl}-piperazin-1-yl-methanone | C, 63.39/63.42; H, 7.37/7.55; N, 22.75/22.87 | 491.67 | 493.58 |
| 130 | 5-{9-cyclopentyl-6-[6-(4-methyl-piperazin-1-yl)-pyridin-3-ylamino]-9H-purin-2-ylamino}-pentan-1-ol | C, 62.61/62.77; H, 7.78/7.85; N, 26.28/26.36 | 478.51 | 480.67 |
| 131 | 5-{9-cyclopentyl-6-[6-(4-ethyl-piperazin-1-ylmethyl)-pyridin-3-ylamino]-9H-purin-2-ylamino}-pentan-1-ol | C, 63.88/63.73; H, 8.14/8.23; N, 24.83/24.72 | 506.54 | 508.72 |
| 132 | {5-[9-cyclopentyl-2-(5-hydroxy-pentylamino)-9H-purin-6-ylamino]-pyridin-2-yl}-(2-oxa-6-aza-spiro[3.3]hept-6-yl)-methanone | C, 61.64/61.57; H, 6.76/6.85; N, 22.12/22.26 | 505.48 | 507.65 |
| 133 | 6-{9-cyclopentyl-6-[4-(2,6-diaza-spiro[3.3]hept-2-yl)-phenylamino]-9H-purin-2-ylamino}-hexan-1-ol | C, 66.09/66.21; H, 7.81/7.95; N, 22.84/22.61 | 489.67 | 491.61 |
| 134 | 6-{9-cyclopentyl-6-[4-(6-methyl-2,6-diaza-spiro[3.3]hept-2-ylmethyl)-phenylamino]-9H-purin-2-ylamino}-hexan-1-ol | C, 67.15/67.23; H, 8.16/8.29; N, 21.60/21.77 | 517.77 | 519.65 |
| 135 | {4-[9-cyclopentyl-2-(6-hydroxy-hexylamino)-9H-purin-6-ylamino]-phenyl}-(6-ethyl-2,6-diaza-spiro[3.3]hept-2-yl)-methanone | C, 65.91/65.77; H, 7.74/7.55; N, 20.50/20.44 | 545.70 | 547.73 |
| 136 | 6-[9-cyclopentyl-6-(6-morpholin-4-yl-pyridin-3-ylamino)-9H-purin-2-ylamino]-hexan-1-ol | C, 62.48/62.51; H, 7.55/7.25; N, 23.32/23.12 | 479.60 | 481.72 |
| 137 | 6-[9-cyclopentyl-6-(6-morpholin-4-ylmethyl-pyridin-3-ylamino)-9H-purin-2-ylamino]-hexan-1-ol | C, 63.13/63.45; H, 7.74/7.51; N, 22.65/22.23 | 493.60 | 495.72 |
| 138 | {5-[9-cyclopentyl-2-(6-hydroxy-hexylamino)-9H-purin-6-ylamino]-pyridin-2-yl}-morpholin-4-yl-methanone | C, 61.40/61.12; H, 7.13/6.88; N, 22.03/22.16 | 507.70 | 509.80 |
| 139 | 2-[9-cyclopentyl-6-(4-morpholin-4-yl-phenylamino)-9H-purin-2-ylamino]-acetamide | C, 60.53/60.72; H, 6.47/6.17; N 25.67/25.85 | 435.63 | 437.61 |
| 140 | 2-[9-cyclopentyl-6-(4-morpholin-4-ylmethyl-phenylamino)-9H-purin-2-ylamino]-acetamide | C, 61.31/61.19; H, 6.71/6.53; N, 24.87/24.64 | 449.43 | 451.58 |
| 141 | 2-{9-cyclopentyl-6-[4-(piperazine-1-carbonyl)-phenylamino]-9H-purin-2-ylamino}-acetamide | C, 59.60/59.44; H, 6.31/6.22; N, 27.20/27.41 | 462.57 | 464.42 |
| 142 | 2-{9-cyclopentyl-6-[6-(4-methyl-piperazin-1-yl)-pyridin-3-ylamino]-9H-purin-2-ylamino}-acetamide | C, 58.65/58.71; H, 6.71/6.63; N, 31.09/31.24 | 449.48 | 451.43 |
| 143 | 2-{9-cyclopentyl-6-[6-(4-methyl-piperazin-1-ylmethyl)-pyridin-3-ylamino]-9H-purin-2-ylamino}-acetamide | C, 59.46/59.39; H, 6.94/6.73; N, 30.15/30.28 | 463.52 | 465.63 |
| 144 | 2-{9-cyclopentyl-6-[6-(4-ethyl-piperazine-1-carbonyl)-pyridin-3-ylamino]-9H-purin-2-ylamino}-acetamide | C, 58.52/58.64; H, 6.55/6.67; N, 28.44/28.39 | 491.51 | 493.65 |
| 145 | 3-{9-cyclopentyl-6-[4-(2-oxa-6-aza-spiro[3.3]hept-6-yl)-phenylamino]-9H-purin-2-ylamino}-propionamide | C, 62.32/62.51; H, 6.54/6.42; N, 24.23/24.11 | 461.51 | 463.60 |
| 146 | 3-{9-cyclopentyl-6-[4-(2,6-diaza-spiro[3.3]hept-2-ylmethyl)-phenylamino]-9H-purin-2-ylamino}-propionamide | C, 63.14/63.22; H, 6.99/6.87; N, 26.51/26.73 | 474.53 | 476.57 |
| 147 | 3-{9-cyclopentyl-6-[4-(6-methyl-2,6-diaza-spiro[3.3]heptane-2-carbonyl)-phenylamino]-9H-purin-2-ylamino}-propionamide | C, 62.01/62.12; H, 6.60/6.52; N, 25.03/25.20 | 502.55 | 504.61 |
| 148 | 3-{9-cyclopentyl-6-[6-(6-ethyl-2,6-diaza-spiro[3.3]hept-2-ylmethyl)-pyridin-3-ylamino]-9H-purin-2-ylamino}-propionamide | C, 61.88/61.96; H, 7.19/7.08; N, 27.76/27.62 | 503.57 | 505.68 |
| 149 | 3-{9-cyclopentyl-6-[6-(morpholine-4-carbonyl)-pyridin-3-ylamino]-9H-purin-2-ylamino}-propionamide | C, 57.61/57.81; H, 6.10/5.98; N, 26.29/26.51 | 478.52 | 480.62 |
| 150 | 4-[9-cyclopentyl-6-(4-morpholin-4-yl-phenylamino)-9H-purin-2-ylamino]-butyramide | C, 62.05/62.13; H, 6.94/7.05; N, 24.12/24.16 | 463.57 | 465.62 |
| 151 | 4-[9-cyclopentyl-6-(4-morpholin-4-ylmethyl-phenylamino)-9H-purin-2-ylamino]-butyramide | C, 62.74/62.84; H, 7.16/7.18; N, 23.41/23.56 | 477.58 | 479.62 |
| 152 | 4-{9-cyclopentyl-6-[4-(morpholine-4-carbonyl)-phenylamino]-9H-purin-2-ylamino}-butyramide | C, 60.96/60.78; H, 6.55/6.67; N, 22.75/22.51 | 491.51 | 493.56 |
| 153 | 4-[9-cyclopentyl-6-(6-piperazin-1-yl-pyridin-3-ylamino)-9H-purin-2-ylamino]-butyramide | C, 59.46/59.37; H, 6.94/6.75; N, 30.15/30.26 | 463.52 | 465.63 |
| 154 | 4-{9-cyclopentyl-6-[6-(4-methyl-piperazin-1-ylmethyl)-pyridin-3-ylamino]-9H-purin-2-ylamino}-butyramide | C, 60.95/60.79; H, 7.37/7.41; N, 28.43/28.55 | 491.59 | 493.66 |
| 155 | 4-{9-cyclopentyl-6-[6-(4-ethyl-piperazine-1-carbonyl)-pyridin-3-ylamino]-9H-purin-2-ylamino}-butyramide | C, 59.98/59.81; H, 6.97/6.89; N, 26.90/26.77 | 519.56 | 521.67 |
| 156 | 5-{9-cyclopentyl-6-[4-(2,6-diaza-spiro[3.3]hept-2-yl)-phenylamino]-9H-purin-2-ylamino}-pentanoic acid amide | C, 63.78/63.64; H, 7.21/7.36; N, 25.75/25.64 | 488.61 | 490.59 |
| 157 | 5-{9-cyclopentyl-6-[4-(6-methyl-2,6-diaza-spiro[3.3]hept-2-ylmethyl)-phenylamino]-9H-purin-2-ylamino}-pentanoic acid amide | C, 64.96/64.81; H, 7.59/7.47; N, 24.35/24.17; O, 3.09/3.22 | 516.64 | 518.61 |

-continued

| No | NAME OF COMPOUND | ELEMENTAL ANALYSES Calcd./Found [%] | MS (ZMD) [M − H]⁻ | MS (ZMD) [M + H]⁺ |
|---|---|---|---|---|
| 158 | 5-{9-cyclopentyl-6-[4-(morpholine-4-carbonyl)-phenylamino]-9H-purin-2-ylamino}-pentanoic acid amide | C, 61.64/61.88; H, 6.76/6.45; N, 22.12/21.96 | 505.60 | 507.72 |
| 159 | 5-[9-cyclopentyl-6-(6-morpholin-4-yl-pyridin-3-ylamino)-9H-purin-2-ylamino]-pentanoic acid amide | C, 60.11/59.88; H, 6.94/6.74; N, 26.29/26.00 | 478.63 | 480.66 |
| 160 | 5-[9-cyclopentyl-6-(6-morpholin-4-ylmethyl-pyridin-3-ylamino)-9H-purin-2-ylamino]-pentanoic acid amide | C, 60.83/60.63; H 7.15/7.18; N, 25.54/25.63 | 492.62 | 494.64 |
| 161 | 5-{9-cyclopentyl-6-[6-(morpholine-4-carbonyl)-pyridin-3-ylamino]-9H-purin-2-ylamino}-pentanoic acid amide | C, 59.16/59.42; H, 6.55/6.89; N, 24.83/24.55 | 506.58 | 508.62 |
| 162 | 6-[9-cyclopentyl-6-(4-morpholin-4-yl-phenylamino)-9H-purin-2-ylamino]-hexanoic acid amide | C, 63.39/63.47; H, 7.37/7.21; N, 22.75/22.67; O, 6.50/6.61 | 491.59 | 493.57 |
| 163 | 6-[9-cyclopentyl-6-(4-piperazin-1-ylmethyl-phenylamino)-9H-purin-2-ylamino]-hexanoic acid amide | C, 64.13/64.27; H, 7.77/7.64; N, 24.93/24.87 | 504.61 | 506.73 |
| 164 | 6-{9-cyclopentyl-6-[4-(4-methyl-piperazine-1-carbonyl)-phenylamino]-9H-purin-2-ylamino}-hexanoic acid amide | C, 63.02/63.14; H, 7.37/7.50; N, 23.62/23.43 | 532.71 | 534.64 |
| 165 | 6-{9-cyclopentyl-6-[6-(4-ethyl-piperazin-1-yl)-pyridin-3-ylamino]-9H-purin-2-ylamino}-hexanoic acid amide | C, 62.28/62.37; H, 7.74/7.65; N, 26.90/26.79 | 519.63 | 521.70 |
| 166 | 6-{9-cyclopentyl-6-[6-(2-oxa-6-aza-spiro[3.3]hept-6-ylmethyl)-pyridin-3-ylamino]-9H-purin-2-ylamino}-hexanoic acid amide | C, 62.41/62.55; H, 7.18/7.24; N, 24.26/24.17 | 518.57 | 520.69 |
| 167 | 6-{9-cyclopentyl-6-[6-(6-methyl-2,6-diaza-spiro[3.3]heptane-2-carbonyl)-pyridin-3-ylamino]-9H-purin-2-ylamino}-hexanoic acid amide | C, 61.52/61.44; H, 7.01/7.16; N, 25.62/25.58 | 545.65 | 547.64 |
| 168 | 9-cyclopentyl-$N^2$-(2-dimethylamino-ethyl)-$N^6$-[4-(6-ethyl-2,6-diaza-spiro[3.3]hept-2-yl)-phenyl]-9H-purine-2,6-diamine | C, 66.25/66.15; H, 8.03/8.18; N, 25.74/25.82 | 488.61 | 490.72 |
| 169 | 9-cyclopentyl-$N^2$-(2-dimethylamino-ethyl)-$N^6$-(4-morpholin-4-ylmethyl-phenyl)-9H-purine-2,6-diamine | C, 64.63/64.05; H, 7.18/7.32; N, 24.12/24.15 | 463.60 | 465.58 |
| 170 | {4-[9-cyclopentyl-2-(2-dimethylamino-ethylamino)-9H-purine-6-ylamino]-phenyl}-morpholin-4-yl-methanone | C, 62.74/62.46; H, 7.16/6.93; N, 23.41/23.66 | 477.63 | 479.70 |
| 171 | 9-cyclopentyl-$N^2$-(2-dimethylamino-ethyl)-$N^6$-(6-morpholin-4-yl-pyridin-3-yl)-9H-purine-2,6-diamine | C, 61.91/61.88; H, 7.58/7.40; N, 27.07/26.83 | 464.61 | 466.72 |
| 172 | 9-cyclopentyl-$N^2$-(2-dimethylamino-ethyl)-$N^6$-(6-morpholin-4-ylmethyl-pyridin-3-yl)-9H-purine-2,6-diamine | C, 61.91/61.87; H, 7.58/7.46; N, 27.08/27.15 | 464.55 | 466.61 |
| 173 | {5-[9-cyclopentyl-2-(2-dimethylamino-ethylamino)-9H-purine-6-ylamino]-pyridin-2-yl}-piperazin-1-yl-methanone | C, 60.23/60.31; H, 7.16/7.25; N, 29.27/29.18 | 477.57 | 479.70 |
| 174 | 9-cyclopentyl-$N^2$-(3-dimethylamino-propyl)-$N^6$-[4-(4-methyl-piperazin-1-yl)-phenyl]-9H-purine-2,6-diamine | C, 65.38/65.27; H, 8.23/8.37; N, 26.39/26.45 | 476.57 | 479.63 |
| 175 | 9-cyclopentyl-$N^2$-(3-dimethylamino-propyl)-$N^6$-[4-(4-ethyl-piperazin-1-ylmethyl)-phenyl]-9H-purine-2,6-diamine | C, 66.50/66.42; H, 8.57/8.51; N, 24.93/24.88 | 504.62 | 506.73 |
| 176 | {4-[9-cyclopentyl-2-(3-dimethylamino-propylamino)-9H-purine-6-ylamino]-phenyl}-(2-oxa-6-aza-spiro[3.3]hept-6-yl)-methanone | C, 64.26/64.18; H, 7.19/7.27; N, 22.21/22.37 | 503.59 | 505.61 |
| 177 | 9-cyclopentyl-$N^6$-[6-(2,6-diaza-spiro[3.3]hept-2-yl)-pyridin-3-yl]-$N^2$-(3-dimethylamino-propyl)-9H-purine-2,6-diamine | C, 63.00/63.14; H, 7.61/7.58; N, 29.39/29.45 | 475.60 | 477.48 |
| 178 | 9-cyclopentyl-$N^2$-(3-dimethylamino-propyl)-$N^6$-[6-(6-ethyl-2,6-diaza-spiro[3.3]hept-2-ylmethyl)-pyridin-3-yl]-9H-purine-2,6-diamine | C, 64.84/64.75; H, 8.16/8.24; N, 27.00/27.09 | 517.67 | 519.75 |
| 179 | {5-[9-cyclopentyl-2-(3-dimethylamino-propylamino)-9H-purine-6-ylamino]-pyridin-2-yl}-morpholin-4-yl methanone | C, 60.83/60.66; H, 7.15/6.93; N, 25.54/25.12 | 492.60 | 494.63 |
| 180 | 9-cyclopentyl-$N^2$-(4-dimethylamino-butyl)-$N^6$-(4-morpholin-4-yl-phenyl)-9H-purine-2,6-diamine | C, 65.24/65.13; H, 8.00/7.81; N, 23.41/23.11 | 477.63 | 479.62 |
| 181 | 9-cyclopentyl-$N^2$-(4-dimethylamino-butyl)-$N^6$-(4-morpholin-4-ylmethyl-phenyl)-9H-purine-2,6-diamine | C, 65.82/65.59; H, 8.18/8.39; N, 22.74/22.56 | 491.65 | 493.68 |
| 182 | {4-[9-cyclopentyl-2-(4-dimethylamino-butylamino)-9H-purine-6-ylamino]-phenyl}-morpholin-4-yl-methanone | C, 64.01/63.82; H, 7.56/7.39; N, 22.12/21.88 | 505.65 | 507.72 |
| 183 | 9-cyclopentyl-$N^2$-(4-dimethylamino-butyl)-$N^6$-(6-morpholin-4-yl-pyridin-3-yl)-9H-purine-2,6-diamine | C, 62.61/62.55; H, 7.78/7.85; N, 26.28/26.36 | 478.57 | 480.60 |
| 184 | 9-cyclopentyl-$N^2$-(4-dimethylamino-butyl)-$N^6$-(6-piperazin-1-ylmethyl-pyridin-3-yl)-9H-purine-2,6-diamine | C, 63.39/63.47; H, 8.18/8.27; N, 28.43/28.32 | 491.61 | 493.68 |

-continued

| No | NAME OF COMPOUND | ELEMENTAL ANALYSES Calcd./Found [%] | MS (ZMD) [M − H]⁻ | MS (ZMD) [M + H]⁺ |
|----|---|---|---|---|
| 185 | {5-[9-cyclopentyl-2-(4-dimethylamino-butylamino)-9H-purine-6-ylamino]-pyridin-2-yl}-(4-methyl-piperazin-1-yl)-methanone | C, 62.28/62.39; H, 7.74/7.86; N, 26.90/26.71 | 519.58 | 521.69 |
| 186 | 9-cyclopentyl-$N^2$-(5-dimethylamino-pentyl)-$N^6$-[4-(4-ethyl-piperazin-1-yl)-phenyl]-9H-purine-2,6-diamine | C, 67.02/67.14; H, 8.73/8.65; N, 24.26/24.35 | 518.65 | 520.70 |
| 187 | 9-cyclopentyl-$N^2$-(5-dimethylamino-pentyl)-$N^6$-[4-(2-oxa-6-aza-spiro[3.3]hept-6-ylmethyl)-phenyl]-9H-purine-2,6-diamine | C, 67.15/67.22; H, 8.16/8.23; N, 21.60/21.78 | 517.69 | 519.65 |
| 188 | {4-[9-cyclopentyl-2-(5-dimethylamino-pentylamino)-9H-purine-6-ylamino]-phenyl}-(2,6-diaza-spiro[3.3]hept-2-yl)-methanone | C, 65.51/65.42; H, 7.77/7.82; N, 23.71/23.65 | 530.68 | 532.72 |
| 189 | 9-cyclopentyl-$N^2$-(5-dimethylamino-pentyl)-$N^6$-[6-(6-ethyl-2,6-diaza-spiro[3.3]hept-2-yl)-pyridin-3-yl]-9H-purine-2,6-diamine | C, 65.38/65.31; H, 8.32/8.40; N, 26.29/26.35 | 531.70 | 533.69 |
| 190 | 9-cyclopentyl-$N^2$-(5-dimethylamino-pentyl)-$N^6$-(6-morpholin-4-ylmethyl-pyridin-3-yl)-9H-purine-2,6-diamine | C, 63.88/63.51; H, 8.14/8.02; N, 24.83/24.51 | 506.71 | 508.75 |
| 191 | {5-[9-cyclopentyl-2-(5-dimethylamino-pentylamino)-9H-purine-6-ylamino]-pyridin-2-yl}-morpholin-4-yl-methanone | C, 62.17/62.36; H, 7.54/7.78; N, 24.16/23.96 | 520.74 | 522.71 |
| 192 | 9-cyclopentyl-$N^2$-(6-dimethylamino-hexyl)-$N^6$-(4-morpholin-4-yl-phenyl)-9H-purine-2,6-diamine | C, 66.37/66.51; H, 8.35/8.61; N, 22.01/21.95 | 505.74 | 507.68 |
| 193 | 9-cyclopentyl-$N^2$-(6-dimethylamino-hexyl)-$N^6$-(4-morpholin-4-ylmethyl-phenyl)-9H-purine-2,6-diamine | C, 66.89/66.75; H, 8.52/8.57; N, 21.52/21.57 | 519.65 | 521.74 |
| 194 | {4-[9-cyclopentyl-2-(6-dimethylamino-hexylamino)-9H-purine-6-ylamino]-phenyl}-piperazin-1-yl-methanone | C, 65.26/65.21; H, 8.12/8.19; N, 23.62/23.55 | 532.67 | 534.75 |
| 195 | 9-cyclopentyl-$N^2$-(6-dimethylamino-hexyl)-$N^6$-[6-(4-methyl-piperazin-1-yl)-pyridin-3-yl]-9H-purine-2,6-diamine | C, 64.58/64.51; H, 8.52/8.48; N, 26.90/26.86 | 519.65 | 521.69 |
| 196 | 9-cyclopentyl-$N^2$-(6-dimethylamino-hexyl)-$N^6$-[6-(4-ethyl-piperazin-1-ylmethyl)-pyridin-3-yl]-9H-purine-2,6-diamine | C, 65.66/65.59; H, 8.82/8.87; N, 25.52/25.59 | 547.74 | 549.83 |
| 197 | {5-[9-cyclopentyl-2-(6-dimethylamino-hexylamino)-9H-purine-6-ylamino]-pyridin-2-yl}-(2-oxa-6-aza-spiro[3.3]hept-6-yl)-methanone | C, 63.60/63.55; H, 7.55/7.59; N, 23.02/23.09; 5.84/5.79 | 546.67 | 548.71 |
| 198 | 1-amino-3-{9-cyclopentyl-6-[4-(6-methyl-2,6-diaza-spiro[3.3]hept-2-yl)-phenylamino]-9H-purin-2-ylamino}-propan-2-ol | C, 62.87/62.83; H, 7.39/7.34; N, 26.39/26.27 | 476.59 | 478.65 |
| 199 | 1-amino-3-{9-cyclopentyl-6-[4-(6-methyl-2,6-diaza-spiro[3.3]hept-2-ylmethyl)-phenylamino]-9H-purin-2-ylamino}-propan-2-ol | C, 63.52/63.48; H, 7.59/7.63; N, 25.64/25.61 | 490.61 | 492.57 |
| 200 | {4-[2-(3-amino-2-hydroxy-propylamino)-9-cyclopentyl-9H-purin-6-ylamino]-phenyl}-morpholin-4-yl-methanone | C, 59.98/59.64; H 6.71/6.50; N, 23.32/23.01 | 479.55 | 481.63 |
| 201 | 1-amino-3-[9-cyclopentyl-6-(6-morpholin-4-yl-pyridin-3-ylamino)-9H-purin-2-ylamino]-propan-2-ol | C, 58.26/58.41; H, 6.89/6.63; N, 27.79/27.55 | 452.61 | 454.63 |
| 202 | 1-amino-3-[9-cyclopentyl-6-(6-morpholin-4-ylmethyl-pyridin-3-ylamino)-9H-purin-2-ylamino]-propan-2-ol | C, 59.08/58.78; H, 7.11/7.15; N, 26.96/26.74 | 466.48 | 468.52 |
| 203 | {5-[2-(3-amino-2-hydroxy-propylamino)-9-cyclopentyl-9H-purin-6-ylamino]-pyridin-2-yl}-morpholin-4-yl-methanone | C, 57.37/57.41; H, 6.49/6.41; N, 26.18/26.07 | 480.51 | 482.61 |
| 204 | {2-[9-cyclopentyl-6-(4-piperazin-1-yl-phenylamino)-9H-purin-2-ylamino]-ethyl}-urea | C, 59.46/59.51; H, 6.94/6.89; N, 30.15/30.08 | 463.62 | 465.53 |
| 205 | (2-{9-cyclopentyl-6-[4-(4-methyl-piperazin-1-ylmethyl)-phenylamino]-9H-purin-2-ylamino}-ethyl)-urea | C, 60.95/60.88; H, 7.37/7.31; N, 28.43/28.37 | 491.60 | 493.65 |
| 206 | (2-{9-cyclopentyl-6-[4-(morpholine-4-carbonyl)-phenylamino]-9H-purin-2-ylamino}-ethyl)-urea | C, 58.40/58.11; H, 6.33/6.56; N, 25.54/25.13 | 492.55 | 494.57 |
| 207 | {2-[9-cyclopentyl-6-(6-morpholin-4-yl-pyridin-3-ylamino)-9H-purin-2-ylamino]-ethyl}-urea | C, 56.64/56.93; H, 6.48/6.19; N, 30.02/29.85 | 465.54 | 467.58 |
| 208 | {2-[9-cyclopentyl-6-(6-morpholin-4-ylmethyl-pyridin-3-ylamino)-9H-purin-2-ylamino]-ethyl}-urea | C, 57.48/57.14; H, 6.71/6.48; N, 29.15/29.00 | 479.55 | 481.56 |
| 209 | (2-{9-cyclopentyl-6-[6-(morpholine-4-carbonye-pyridin-3-ylamino]-9H-purin-2-ylamino}-ethyl)-urea | C, 55.86/55.91; H, 6.11/6.15; N, 28.32/28.22 | 493.51 | 495.59 |
| 210 | {3-[9-cyclopentyl-6-(4-piperazin-1-yl-phenylamino)-9H-purin-2-ylamino]-propyl}-urea | C, 60.23/60.18; H, 7.16/7.24; N, 29.27/29.19 | 477.53 | 479.62 |
| 211 | (3-{9-cyclopentyl-6-[4-(4-methyl-piperazin-1-ylmethyl)-phenylamino]-9H-purin-2-ylamino}-propyl)-urea | C, 61.64/61.60; H, 7.56/7.63; N, 27.65/27.59 | 505.66 | 507.73 |
| 212 | (3-{9-cyclopentyl-6-[4-(4-ethyl-piperazine-1-carbonyl)-phenylamino]-9H-purin-2-ylamino}-propyl)-urea | C, 60.65/60.73; H, 7.16/7.22; N, 26.20/26.14; H, 5.98/5.79 | 533.59 | 535.62 |

-continued

| No | NAME OF COMPOUND | ELEMENTAL ANALYSES Calcd./Found [%] | MS (ZMD) [M − H]⁻ | [M + H]⁺ |
|---|---|---|---|---|
| 213 | (3-{9-cyclopentyl-6-[6-(2-oxa-6-aza-spiro[3.3]hept-6-yl)-pyridin-3-ylamino]-9H-purin-2-ylamino}-propyl)-urea | C, 58.52/58.66; H, 6.55/6.71; N, 28.44/28.32 | 491.55 | 493.51 |
| 214 | (3-{9-cyclopentyl-6-[6-(6-ethyl-2,6-diaza-spiro[3.3]hept-2-ylmethyl)-pyridin-3-ylamino]-9H-purin-2-ylamino}-propyl)-urea | C, 60.77/60.69; H, 7.37/7.45; N, 28.87/28.71 | 532.72 | 534.65 |
| 215 | (3-{9-cyclopentyl-6-[6-(morpholine-4-carbonyl)-pyridin-3-ylamino]-9H-purin-2-ylamino}-propyl)-urea | C, 56.68/56.47; H, 6.34/6.55; N, 27.54/27.69 | 507.54 | 509.51 |
| 216 | {4-[9-cyclopentyl-6-(4-morpholin-4-yl-phenylamino)-9H-purin-2-ylamino]-butyl}-urea | C, 60.83/60.52; H, 7.15/6.98; N, 25.54/25.13 | 492.60 | 494.62 |
| 217 | {4-[9-cyclopentyl-6-(4-morpholin-4-ylmethyl-phenylamino)-9H-purin-2-ylamino]-butyl}-urea | C, 61.52/61.52; H, 7.35/7.28; N, 24.83/24.78 | 506.62 | 508.60 |
| 218 | (4-{9-cyclopentyl-6-[4-(morpholine-4-carbonyl)-phenylamino]-9H-purin-2-ylamino}-butyl)-urea | C, 59.87/59.66; H, 6.76/6.75; N, 24.17/24.00 | 520.70 | 522.69 |
| 219 | {4-{9-cyclopentyl-6-(6-morpholin-4-yl-pyridin-3-ylamino)-9H-purin-2-ylamino]-butyl}-urea | C, 58.28/58.61; H, 6.93/6.72; N, 28.32/28.55 | 493.55 | 495.63 |
| 220 | {4-{9-cyclopentyl-6-(6-morpholin-4-ylmethyl-pyridin-3-ylamino)-9H-purin-2-ylamino]-butyl}-urea | C, 59.04/59.16; H, 7.13/7.20; N, 27.54/27.45 | 507.59 | 509.55 |
| 221 | (4-{9-cyclopentyl-6-[6-(piperazine-1-carbonyl)-pyridin-3-ylamino]-9H-purin-2-ylamino}-butyl)-urea | C, 57.56/57.50; H, 6.76/6.84; N, 29.54/29.48 | 520.60 | 522.74 |
| 222 | (5-{9-cyclopentyl-6-[4-(4-ethyl-piperazin-1-yl)-phenylamino]-9H-purin-2-ylamino}-pentyl)-urea | C, 62.90/62.81; H, 7.92/7.87; N, 26.20/26.15; O, 2.99/2.75 | 533.73 | 535.69 |
| 223 | (5-{9-cyclopentyl-6-[4-(2-oxa-6-aza-spiro[3.3]hept-6-ylmethyl)-phenylamino]-9H-purin-2-ylamino}-pentyl)-urea | C, 63.02/63.15; H, 7.37/7.45; N, 23.62/23.53; O, 6.00/6.07 | 532.64 | 534.60 |
| 224 | (5-{9-cyclopentyl-6-[4-(6-methyl-2,6-diaza-spiro[3.3]heptane-2-carbonyl)-phenylamino]-9H-purin-2-ylamino}-pentyl)-urea | C, 62.12/62.20; H, 7.19/7.25; N, 24.98/24.82; O, 5.71/5.66 | 559.65 | 561.71 |
| 225 | (5-{9-cyclopentyl-6-[6-(6-ethyl-2,6-diaza-spiro[3.3]hept-2-yl)-pyridin-3-ylamino]-9H-purin-2-ylamino}-pentyl)-urea | C, 61.40/61.34; H, 7.55/7.67; N, 28.13/28.25; O, 2.92/2.84 | 546.63 | 548.73 |
| 226 | {5-[9-cyclopentyl-6-(6-morpholin-4-ylmethyl-pyridin-3-ylamino)-9H-purin-2-ylamino]-pentyl}-urea | C, 59.75/59.55; H, 7.33/7.01; N, 26.80/26.97 | 521.64 | 523.66 |
| 227 | (5-{9-cyclopentyl-6-[6-(morpholine-4-carbonyl)-pyridin-3-ylamino]-9H-purin-2-ylamino}-pentyl)-urea | C, 58.19/58.22; H, 6.76/6.45; N, 26.10/25.88 | 535.60 | 537.70 |
| 228 | {6-[9-cyclopentyl-6-(4-morpholin-4-yl-phenylamino)-9H-purin-2-ylamino]-hexyl}-urea | C, 62.17/62.00; H, 7.54/7.33; N, 24.17/24.29 | 520.61 | 522.64 |
| 229 | {6-[9-cyclopentyl-6-(4-morpholin-4-ylmethyl-phenylamino)-9H-purin-2-ylamino]-hexyl}-urea | C, 62.78/62.59; H, 7.71/7.52; N, 23.53/23.67 | 534.66 | 536.72 |
| 230 | (6-{9-cyclopentyl-6-[4-(morpholine-4-carbonyl)-phenylamino]-9H-purin-2-ylamino}-hexyl)-urea | C, 61.18/61.24; H, 7.15/7.26; N, 22.93/22.78; O, 8.73/8.60 | 548.62 | 550.60 |
| 231 | {6-[9-cyclopentyl-6-(6-piperazin-1-ylmethyl-pyridin-3-ylamino)-9H-purin-2-ylamino]-hexyl}-urea | C, 60.54/60.62; H, 7.71/7.78; N, 28.76/28.65; O, 2.99/2.80 | 534.65 | 536.72 |
| 232 | (6-{9-cyclopentyl-6-[6-(4-methyl-piperazine-1-carbonyl)-pyridin-3-ylamino]-9H-purin-2-ylamino}-hexyl)-urea | C, 59.66/59.73; H, 7.33/7.29; N, 27.33/27.27; O, 5.68/5.72 | 562.69 | 564.75 |
| 233 | N-(2-{9-cyclopentyl-6-[4-(4-ethyl-piperazin-1-ylmethyl)-phenylamino]-9H-purin-2-ylamino}-ethyl)-guanidine | C, 61.76/61.83; H, 7.77/7.65; N, 30.47/30.39 | 504.61 | 506.70 |
| 234 | N-(2-{9-cyclopentyl-6-[4-(2-oxa-6-aza-spiro[3.3]heptane-6-carbonyl)-phenylamino]-9H-purin-2-ylamino}-ethyl)-guanidine | C, 59.51/59.62; H, 6.39/6.43; N, 27.76/27.65; O, 6.34/6.29 | 503.57 | 505.61 |
| 235 | N-(2-{9-cyclopentyl-6-[6-(6-methyl-2,6-diaza-spiro[3.3]hept-2-yl)-pyridin-3-ylamino]-9H-purin-2-ylamino}-ethyl)-guanidine | C, 58.76/58.82; H, 6.99/6.84; N, 34.26/34.18 | 489.55 | 491.63 |
| 236 | N-{2-[9-cyclopentyl-6-(6-morpholin-4-ylmethyl-pyridin-3-ylamino)-9H-purin-2-ylamino]-ethyl}-guanidine | C, 57.60/57.23; H, 6.94/6.72; N, 32.13/32.00 | 478.55 | 480.52 |
| 237 | N-(2-{9-cyclopentyl-6-[6-(morpholine-4-carbonyl)-pyridin-3-ylamino]-9H-purin-2-ylamino}-ethyl)-guanidine | C, 55.97/55.84; H, 6.33/6.12; N, 31.22/31.05 | 492.51 | 494.63 |
| 238 | N-{3-[9-cyclopentyl-6-(4-morpholin-4-yl-phenylamino)-9H-purin-2-ylamino]-propyl}-guanidine | C, 60.23/60.54; H, 7.16/6.95; N, 29.27/29.36 | 477.54 | 479.62 |
| 239 | N-{3-[9-cyclopentyl-6-(4-morpholin-4-ylmethyl-phenylamino)-9H-purin-2-ylamino]-propyl}-guanidine | C, 60.95/60.87; H, 7.37/7.43; N, 28.43/28.32; O, 3.25/3.14 | 491.57 | 493.65 |
| 240 | N-(3-{9-cyclopentyl-6-[4-(piperazine-1-carbonyl)-phenylamino]-9H-purin-2-ylamino}-propyl)-guanidine | C, 59.39/59.48; H, 6.98/6.83; N, 30.47/30.39; O, 3.16/3.22 | 504.60 | 506.67 |

-continued

| No | NAME OF COMPOUND | ELEMENTAL ANALYSES Calcd./Found [%] | MS (ZMD) [M − H]⁻ | [M + H]⁺ |
|---|---|---|---|---|
| 241 | N-(3-{9-cyclopentyl-6-[4-(2,6-diaza-spiro[3.3]heptane-2-carbonyl)-phenylamino]-9H-purin-2-ylamino}-propyl)-guanidine | C, 60.33/60.25; H, 6.82/6.75; N, 29.77/29.81; O, 3.09/3.15 | 516.59 | 518.62 |
| 242 | N-(3-{9-cyclopentyl-6-[6-(6-ethyl-2,6-diaza-spiro[3.3]hept-2-yl)-pyridin-3-ylamino]-9H-purin-2-ylamino}-propyl)-guanidine | C, 60.21/60.15; H, 7.38/7.44; N, 32.41/32.35 | 517.61 | 519.63 |
| 243 | N-{3-[9-cyclopentyl-6-(6-morpholin-4-ylmethyl-pyridin-3-ylamino)-9H-purin-2-ylamino]-propyl}-guanidine | C, 58.40/58.11; H, 7.15/6.99; N, 31.21/31.45 | 492.61 | 494.61 |
| 244 | N-(3-{9-cyclopentyl-6-[6-(morpholine-4-carbonyl)-pyridin-3-ylamino]-9H-purin-2-ylamino}-propyl)-guanidine | C, 56.79/56.48; H, 6.55/6.85; N, 30.35/30.00 | 506.59 | 508.62 |
| 245 | N-{4-[9-cyclopentyl-6-(4-morpholin-4-yl-phenylamino)-9H-purin-2-ylamino]-butyl}-guanidine | C, 60.95/60.87; H, 7.37/7.12; N, 28.43/28.09 | 491.64 | 493.58 |
| 246 | N-{4-[9-cyclopentyl-6-(4-morpholin-4-ylmethyl-phenylamino)-9H-purin-2-ylamino]-butyl}-guanidine | C, 61.64/61.73; H, 7.56/7.63; N, 27.65/27.51; O, 3.16/3.09 | 505.67 | 507.71 |
| 247 | N-(4-{9-cyclopentyl-6-[4-(piperazine-1-carbonyl)-phenylamino]-9H-purin-2-ylamino}-butyl)-guanidine | C, 60.09/60.17; H, 7.18/7.11; N, 29.65/29.60; O, 3.08/3.15 | 518.63 | 520.69 |
| 248 | N-(4-{9-cyclopentyl-6-[6-(4-methyl-piperazin-1-yl)-pyridin-3-ylamino]-9H-purin-2-ylamino}-butyl)-guanidine | C, 59.27/59.33; H, 7.56/7.49; N, 33.17/33.09 | 505.66 | 507.60 |
| 249 | N-(4-{9-cyclopentyl-6-[6-(4-ethyl-piperazin-1-ylmethyl)-pyridin-3-ylamino]-9H-purin-2-ylamino}-butyl)-guanidine | C, 60.65/60.71; H, 7.92/7.89; N, 31.43/31.39 | 533.73 | 535.79 |
| 250 | N-(4-{9-cyclopentyl-6-[6-(2,6-diaza-spiro[3.3]heptane-2-carbonyl)-pyridin-3-ylamino]-9H-purin-2-ylamino}-butyl)-guanidine | C, 58.63/58.59; H, 6.81/6.89; N, 31.56/31.48; O, 3.00/3.09 | 531.68 | 533.71 |
| 251 | N-(5-{9-cyclopentyl-6-[4-(6-ethyl-2,6-diaza-spiro[3.3]hept-2-yl)-phenylamino]-9H-purin-2-ylamino}-pentyl)-guanidine | C, 63.83/63.92; H, 7.94/7.87; N, 28.23/28.17 | 544.71 | 546.75 |
| 252 | N-{5-[9-cyclopentyl-6-(4-morpholin-4-ylmethyl-phenylamino)-9H-purin-2-ylamino]-pentyl}-guanidine | C, 62.28/61.95; H, 7.74/7.85; N, 26.90/26.65 | 519.63 | 521.72 |
| 253 | N-(5-{9-cyclopentyl-6-[4-(morpholine-4-carbonyl)-phenylamino]-9H-purin-2-ylamino}-pentyl)-guanidine | C, 60.65/60.95; H, 7.16/7.20; N, 26.20/26.10 | 533.62 | 535.70 |
| 254 | N-{5-[9-cyclopentyl-6-(6-morpholin-4-yl-pyridin-3-ylamino)-9H-purin-2-ylamino]-pentyl}-guanidine | C, 59.15/59.00; H, 7.35/7.62; N, 30.35/30.42 | 506.58 | 508.60 |
| 255 | N-{5-[9-cyclopentyl-6-(6-morpholin-4-ylmethyl-pyridin-3-ylamino)-9H-purin-2-ylamino]-pentyl}-guanidine | C, 59.86/60.11; H, 7.54/7.21; N, 29.54/29.33 | 520.63 | 522.70 |
| 256 | N-(5-{9-cyclopentyl-6-[6-(morpholine-4-carbonyl)-pyridin-3-ylamino]-9H-purin-2-ylamino}-pentyl)-guanidine | C, 58.30/58.39; H, 6.96/6.87; N, 28.76/28.64; O, 5.97/5.89 | 534.66 | 536.60 |
| 257 | N-{6-[9-cyclopentyl-6-(4-piperazin-1-yl-phenylamino)-9H-purin-2-ylamino]-hexyl}-guanidine | C, 62.40/62.53; H, 7.95/7.90; N, 29.65/29.59 | 518.66 | 520.72 |
| 258 | N-{6-[9-cyclopentyl-6-[4-(4-methyl-piperazin-1-ylmethyl)-phenylamino]-9H-purin-2-ylamino}-hexyl)-guanidine | C, 63.59/63.65; H, 8.28/8.36; N, 28.13/28.06 | 546.70 | 548.77 |
| 259 | N-(6-{9-cyclopentyl-6-[4-(4-ethyl-piperazine-1-carbonyl)-phenylamino]-9H-purin-2-ylamino}-hexyl)-guanidine | C, 62.58/62.64; H, 7.88/7.71; N, 26.76/26.66; O, 2.78/2.83 | 574.81 | 576.76 |
| 260 | N-(6-{9-cyclopentyl-6-[6-(2-oxa-6-aza-spiro[3.3]hept-6-yl)-pyridin-3-ylamino]-9H-purin-2-ylamino}-hexyl)-guanidine | C, 60.77/60.69; H, 7.37/7.43; N, 28.87/28.73; O, 3.00/3.06 | 532.64 | 534.72 |
| 261 | N-(6-{9-cyclopentyl-6-[6-(2,6-diaza-spiro[3.3]hept-2-ylmethyl)-pyridin-3-ylamino]-9H-purin-2-ylamino}-hexyl)-guanidine | C, 61.51/61.63; H, 7.74/7.65; N, 30.74/30.65 | 545.65 | 547.70 |
| 262 | N-(6-{9-cyclopentyl-6-[6-(6-methyl-2,6-diaza-spiro[3.3]heptane-2-carbonyl)-pyridin-3-ylamino]-9H-purin-2-ylamino}-hexyl)-guanidine | C, 60.60/60.72; H, 7.37/7.42; N, 29.25/29.17; O, 2.78/2.69 | 573.68 | 575.74 |
| 263 | (N²-(4-amino-cyclohexyl)-9-cyclopentyl-N⁶-(4-pyrrolidin-1-yl-phenyl)-9H-purine-2,6-diamine) | C, 67.80/67.71; H, 7.88/7.92; N, 24.33/24.01 | 459.72 | 461.70 |
| 264 | N²-(4-Amino-cyclohexyl)-9-cyclopentyl-N⁶-(4-morpholin-4-ylmethyl-phenyl)-9H-purine-2,6-diamine | C, 66.09/66.04; H, 7.81/7.59; N, 22.84/22.61 | 459.64 | 491.65 |
| 265 | N²-(4-amino-butyl)-9-cyclopentyl-N⁶-(4-morpholin-4-yl-phenyl)-9H-purine-2,6-diamine | C, 63.97/64.11; H, 7.61/7.38; N, 24.87/24.59 | 449.62 | 451.58 |
| 266 | N²-(4-amino-butyl)-9-cyclopentyl-N⁶-[4-(4-ethyl-piperazin-1-yl)-phenyl]-9H-purine-2,6-diamine | C, 65.38/65.29; H, 8.23/7.89; N, 26.39/26.39 | 476.86 | 478.91 |
| 267 | N²-(5-amino-pentyl)-9-cyclopentyl-N⁶-(4-morpholin-4-ylmethyl-phenyl)-9H-purine-2,6-diamine | C, 65.24/65.56; H, 8.00/8.05; N, 23.14/22.92 | 477.82 | 479.90 |
| 268 | (9-cyclopentyl-2-piperidin-1-yl-9H-purin-6-yl)-(4-morpholin-4-yl-phenyl)-amine | C, 67.65/67.29; H, 7.64/7.38; N, 21.24/21.03 | 461.84 | 463.78 |

-continued

| No | NAME OF COMPOUND | ELEMENTAL ANALYSES Calcd./Found [%] | MS (ZMD) [M − H]⁻ | [M + H]⁺ |
|---|---|---|---|---|
| 269 | $N^2$-(4-amino-cyclohexyl)-9-cyclopentyl-$N^6$-(6-morpholin-4-yl-pyridin-3-yl)-9H-purine-2,6-diamine | C, 62.87/62.61; H, 7.39/7.11; N, 26.39/26.02 | 476.52 | 478.57 |
| 270 | $N^2$-(4-Amino-butyl)-9-cyclopentyl-$N^6$-(4-morpholin-4-ylmethyl-phenyl)-9H-purine-2,6-diamine | C, 64.63/64.54; H, 7.81/7.63; N, 24.12/24.00. | 463.60 | 465.55 |
| 271 | (9-cyclopentyl-2-piperidin-1-yl-9H-purin-6-yl)-(4-morpholin-4-ylmethyl-phenyl)-amine | C, 67.65/67.38; H, 7.64/7.50; N, 21.24/20.88. | 460.55 | 462.62 |
| 272 | $N^2$-(4-amino-cyclohexyl)-9-cyclopentyl-$N^6$-[4-(2-oxa-6-aza-spiro[3.3]hept-6-yl)-phenyl]-9H-purine-2,6-diamine | C, 66.37/66.11; H, 7.43/7.08; N, 22.93/22.69 | 487.61 | 489.72 |
| 273 | 1-amino-3-{6-[4-(4-ethyl-piperazin-1-yl)-phenylamino]-9-cyclopentyl-9H-purin-2-ylamino}-propan-2-ol | C, 62.61/62.88; 7.78/7.92; N, 26.28/26.46 | 478.60 | 480.58 |
| 274 | 2-[9-Cyclopentyl-6-(4-morpholin-4-ylmethyl-phenylamino)-9H-purin-2-ylamino]-ethanol | C, 63.14/63.18; H, 7.14/7.28; N, 2241/22.08 | 436.55 | 438.62 |
| 275 | 3-[9-Cyclopentyl-6-(4-morpholin-4-ylmethyl-phenylamino)-9H-purin-2-ylamino]-propan-1-ol | C, 63.84/63.95; H, 7.37/7.51; N, 21.71/21.39 | 450.61 | 452.60 |
| 276 | 4-[9-Cyclopentyl-6-(4-morpholin-4-ylmethyl-phenylamino)-9H-purin-2-ylamino]-butan-1-ol | C, 64.49/64.28; H, 7.58/7.62; N, 21.06/20.88 | 464.60 | 466.63 |

Example 25 Anticancer Activity of Novel Compounds In Vitro

Cytotoxicity of the compounds is the major property determining their anticancer effect in vivo. One of the parameters used, as the basis for cytotoxicity assays, is the integrity of cytoplasmic membrane of viable cells. For example, a microtiter assay, which uses acetomethoxy derivate of calcein (Calcein AM), is widely used for evaluation of cell proliferation and cytotoxicity. This assay is used in drug screening programs and in chemosensitivity testing. Intracellular esterases of viable cells convert calcein AM to green-fluorescent calcein of which signal corresponds to the number of viable cells in the culture.

We have been using the following cell lines: MV4-11 (acute myeloid leukemia, FLT3-ITD positive), MOLM-13 (acute myeloid leukemia, FLT3-ITD positive), THP-1 (acute myeloid leukemia, wt FLT3), U937 (monocytic leukemia, wt FLT3), EOL-1 (eosinophilic leukaemia, carrying the fusion FIP1L1-PDGFRA), H1703 (non-small cell lung carcinoma, PDGFRA amplification). They were maintained in RPMI-1640 supplemented with 10% fetal bovine serum, penicillin (100 U/ml) and streptomycin (100 μg/ml). Kasumi-1 (acute myeloid leukemia, KIT mutation Asn822Lys) cells were cultivated in RPMI-1640 supplemented with 15% fetal bovine serum, penicillin (100 U/ml) and streptomycin (100 μg/ml). K562 and MCF-7 cell lines were maintained in DMEM supplemented with 10% fetal bovine serum, penicilin (100 U/ml) and streptomycin (100 μg/ml). All cell lines were cultivated at 37° C. in 5% $CO_2$. For cytotoxicity assays, cells were seeded in appropriate densities into 96 well plates and the next day tested compounds were added at various concentrations in triplicates. Three days after drug addition, Calcein AM solution (final concentration 1 μg/ml; Thermo Scientific, USA) was added into each well and incubated for 1 h. After this incubation period, fluorescence of the live cells was measured at 485 nm/538 nm (ex/em) with a Fluoroskan Ascent microplate reader (Labsystems). The $EC_{50}$ value, the drug concentration lethal to 50% of the cancer cells, was calculated from the obtained dose response curves.

Cytoxicity of novel compounds was tested on a panel of cell lines with different histogenetic origin. Significant activities were obtained especially in AML cell lines MV4-11 and MOLM-13 with FLT3-ITD mutation and EOL-1 cell line expressing FIP1L1-PDGFRA fusion protein where the $EC_{50}$ values of novel derivatives reached low nanomolar ranges (for example see Table 3). In addition, several compounds were active also against H1703 non-small cell lung carcinoma cell line reported to have 24-fold amplification of the region that contains the PDGFRA locus.

TABLE 3

In vitro antiproliferative activity of selected novel compounds

| | $EC_{50}$ values (μM) | | | | | | | | | |
|---|---|---|---|---|---|---|---|---|---|---|
| Compound | MV4-11 | MOLM-13 | EOL-1 | Kasumi-1 | THP-1 | U937 | HL60 | K562 | MCF-7 | H1703 |
| 2 | 0.010 | 0.015 | 0.023 | 0.481 | 2.280 | 1.797 | 3.509 | 1.570 | 0.520 | n.a. |
| 263 | 0.018 | 0.024 | 0.030 | 0.569 | 3.114 | 3.171 | 3.931 | 1.270 | 1.330 | n.a. |
| 3 | 0.018 | 0.020 | 0.015 | 1.229 | 3.025 | 3.661 | 1.291 | 1.229 | 0.273 | n.a. |
| 5 | 0.011 | 0.014 | 0.019 | 0.588 | 0.903 | 0.440 | 1.210 | 0.432 | 0.410 | n.a. |
| 8 | 0.042 | 0.056 | 0.049 | 0.636 | 2.099 | 1.354 | 1.419 | 0.391 | 0.220 | n.a. |
| 14 | 0.083 | 0.025 | 0.054 | 0.781 | 1.862 | 1.454 | 2.681 | 1.562 | 1.520 | n.a. |
| 18 | 0.049 | 0.030 | 0.057 | 0.924 | 1.803 | 2.291 | 1.442 | 1.876 | 1.120 | n.a. |
| 27 | 0.024 | 0.019 | 0.053 | 0.637 | 0.624 | 0.794 | 0.989 | 0.570 | 0.265 | n.a. |
| 264 | 0.001 | 0.001 | 0.006 | 0.523 | 0.865 | 0.616 | n.a. | 0.450 | 0.196 | 0.156 |
| 1 | 0.001 | 0.004 | 0.008 | 0.944 | 1.013 | 2.128 | n.a. | 1.186 | 0.320 | 0.189 |
| 28 | 0.001 | 0.004 | 0.013 | 0.839 | 0.514 | 0.605 | n.a. | 1.049 | 0.925 | 0.214 |
| 172 | 0.003 | 0.017 | 0.014 | 1.501 | 1.522 | 1.484 | n.a. | 1.162 | 0.430 | 0.350 |
| 149 | 0.007 | n.a. | n.a. | 1.013 | n.a. | n.a. | n.a. | 1.173 | 0.688 | n.a. |

TABLE 3-continued

In vitro antiproliferative activity of selected novel compounds

| | EC$_{50}$ values (µM) | | | | | | | | | |
|---|---|---|---|---|---|---|---|---|---|---|
| Compound | MV4-11 | MOLM-13 | EOL-1 | Kasumi-1 | THP-1 | U937 | HL60 | K562 | MCF-7 | H1703 |
| 155 | 0.164 | n.a. | n.a. | n.a. | n.a. | n.a. | n.a. | 5.170 | 4.705 | n.a. |
| 156 | 0.001 | n.a. | n.a. | n.a. | n.a. | n.a. | n.a. | 0.840 | 0.697 | n.a. |
| 266 | 0.018 | 0.014 | 0.074 | n.a. | 2.986 | 3.769 | n.a. | 1.430 | 2.150 | 0.978 |
| 265 | 0.017 | 0.016 | 0.039 | n.a. | >4 | >4 | n.a. | 3.740 | 3.255 | 0.482 |
| 270 | 0.029 | 0.014 | 0.036 | n.a. | 1.242 | >4 | n.a. | 1.810 | 2.105 | 0.564 |
| 179 | 0.013 | 0.078 | 0.225 | n.a. | >4 | n.a. | n.a. | n.a. | 2.210 | n.a. |
| 182 | 0.002 | 0.017 | 0.040 | 1.684 | 1.503 | 0.631 | n.a. | 4.215 | 1.595 | n.a. |
| 183 | 0.0005 | 0.005 | 0.014 | 0.183 | 0.360 | 0.400 | n.a. | 0.980 | 0.665 | n.a. |
| 199 | 0.011 | 0.043 | n.a. | 0.227 | 0.925 | 1.003 | n.a. | 1.365 | 0.670 | n.a. |
| 267 | 0.032 | 0.020 | 0.071 | 1.248 | 2.418 | 3.629 | n.a. | 1.790 | 2.265 | n.a. |
| 38 | 0.086 | 0.064 | 0.276 | 1.233 | 3.590 | 2.920 | n.a. | 4.570 | 5.546 | n.a. |
| 272 | 0.003 | 0.004 | 0.022 | 0.773 | 0.693 | 0.638 | n.a. | 1.180 | 1.055 | 0.412 |
| 44 | 0.061 | 0.060 | 0.400 | 0.470 | >10 | 9.348 | n.a. | 5.105 | 6.170 | 0.927 |
| 56 | 0.066 | 0.050 | 0.378 | 0.797 | 8.971 | 8.364 | n.a. | 2.745 | 3.295 | 0.708 |
| 271 | 0.701 | 0.431 | 1.366 | 2.160 | >10 | 7.615 | n.a. | 8.275 | 12.290 | n.a. |
| 58 | 0.017 | 0.017 | 0.056 | 0.492 | 1.132 | 0.794 | n.a. | 0.695 | 0.440 | n.a. |
| 269 | 0.004 | n.a. | 0.010 | n.a. | n.a. | 1.488 | n.a. | 1.355 | 0.960 | n.a. |
| 46 | 0.020 | n.a. | 0.377 | n.a. | n.a. | n.a. | n.a. | n.a. | n.a. | n.a. |
| 274 | 0.074 | n.a. | 0.503 | n.a. | n.a. | n.a. | n.a. | n.a. | n.a. | n.a. |
| 275 | 0.066 | n.a. | 0.730 | n.a. | n.a. | n.a. | n.a. | n.a. | n.a. | n.a. |
| 276 | 0.029 | n.a. | 0.308 | n.a. | n.a. | n.a. | n.a. | n.a. | n.a. | n.a. | n.a.: not analyzed

Example 26 Kinase Inhibitory Activities of Novel Compounds

CDK1/Cyclin B and CDK2/Cyclin E kinases were produced in Sf9 insect cells via baculoviral infection and purified on a NiNTA column (Qiagen). CDK5/p35 and CDK7Cyclin H/MAT1, FLT3 WT, FLT3-ITD and FLT3 D835 were purchased from ProQinase GmbH. The kinase reactions were assayed with 1 mg/mL histone H1 (for CDK1, CDK2 and CDK5), (YSPTSPS)$_2$KK peptide (for CDK7) or AGLT substrate (for FLT3) in the presence of 15/15/0.15/1.5/1 µM ATP (for CDK1/CDK2/CDK5/CDK7/FLT3), 0.05 µCi [γ-$^{33}$P]ATP and of the test compound in a final volume of 10 µL, all in a reaction buffer (60 mM HEPES-NaOH, pH 7.5, 3 mM MgCl$_2$, 3 mM MnCl$_2$, 3 µM Na-orthovanadate, 1.2 mM DTT, 2.5 µg/50 µl PEG$_{20,000}$). The reactions were stopped by adding 5 µL of 3% aq H$_3$PO$_4$. Aliquots were spotted onto P-81 phosphocellulose (Whatman), washed 3× with 0.5% aq H$_3$PO$_4$ and finally air-dried. Kinase inhibition was quantified using digital image analyzer FLA-7000 (Fujifilm) and expressed as a residual activity of kinase or as IC$_{50}$, the concentration of the test compounds required to decrease the enzymatic activity by 50%.

As shown in Table 4, all compounds were very potent inhibitors of wild type FLT3 as well as FLT3 variants with ITD and point mutation D835. The IC$_{50}$ values ranged at low nanomolar concentrations. Moreover, novel compounds displayed activity against several CDKs.

TABLE 4

Kinase inhibitory activity of selected novel compounds expressed as IC$_{50}$.

| | IC$_{50}$ values (µM) | | | | | | |
|---|---|---|---|---|---|---|---|
| Compound | FLT3 WT | FLT3 ITD | FLT3 D835 | CDK1 | CDK2 | CDK5 | CDK7 |
| 2 | 0.015 | 0.004 | 0.003 | 0.045 | 0.008 | 0.065 | n.a. |
| 263 | 0.021 | 0.003 | 0.011 | 0.082 | 0.031 | 0.359 | n.a. |
| 3 | 0.021 | 0.007 | 0.003 | 0.034 | 0.004 | 0.058 | n.a. |
| 4 | 0.022 | 0.002 | 0.005 | 0.028 | 0.004 | 0.027 | 0.082 |
| 7 | 0.026 | 0.005 | 0.011 | 0.013 | 0.006 | 0.030 | 0.197 |
| 14 | 0.014 | 0.004 | 0.010 | 0.037 | 0.004 | 0.065 | n.a. |
| 20 | 0.015 | 0.004 | 0.004 | 0.040 | 0.005 | 0.044 | n.a. |
| 27 | 0.019 | 0.002 | 0.011 | n.a. | 0.002 | n.a. | n.a. |
| 264 | 0.013 | 0.001 | 0.009 | n.a. | 0.007 | 0.034 | 0.178 |
| 1 | 0.023 | 0.002 | 0.007 | n.a. | 0.017 | n.a. | n.a. |
| 28 | 0.010 | 0.003 | 0.002 | n.a. | 0.028 | n.a. | n.a. |
| 172 | 0.011 | 0.003 | 0.005 | n.a. | 0.016 | n.a. | n.a. |
| 171 | 0.037 | 0.015 | 0.010 | n.a. | 0.005 | n.a. | n.a. |
| 155 | n.a. | n.a. | n.a. | n.a. | 2.600 | n.a. | n.a. |
| 174 | n.a. | n.a. | n.a. | n.a. | 16.404 | n.a. | n.a. |
| 156 | n.a. | n.a. | n.a. | n.a. | 0.006 | n.a. | n.a. |
| 266 | 0.013 | 0.002 | 0.003 | n.a. | 0.586 | n.a. | n.a. |
| 265 | 0.023 | 0.004 | 0.007 | n.a. | 0.642 | n.a. | n.a. |
| 270 | 0.006 | 0.002 | 0.005 | n.a. | 0.625 | n.a. | n.a. |
| 179 | 0.090 | 0.012 | 0.023 | n.a. | 0.040 | n.a. | n.a. |
| 182 | 0.013 | n.a. | n.a. | n.a. | 0.005 | n.a. | n.a. |
| 185 | 0.020 | n.a. | n.a. | n.a. | 0.003 | n.a. | n.a. |
| 199 | 0.013 | n.a. | n.a. | n.a. | 0.005 | n.a. | n.a. |
| 267 | 0.025 | n.a. | n.a. | 6.049 | 2.039 | 3.709 | n.a. |
| 38 | 0.021 | n.a. | n.a. | 6.160 | 3.556 | 8.164 | n.a. |
| 272 | 0.013 | n.a. | n.a. | 0.094 | 0.025 | 0.059 | n.a. |
| 44 | 0.034 | n.a. | n.a. | n.a. | 1.723 | n.a. | n.a. |
| 56 | 0.088 | n.a. | n.a. | n.a. | 1.917 | n.a. | n.a. |
| 271 | 0.073 | n.a. | n.a. | n.a. | 1.977 | n.a. | n.a. |
| 60 | 0.021 | n.a. | n.a. | n.a. | 0.028 | n.a. | n.a. |
| 269 | n.a. | n.a. | n.a. | n.a. | 0.008 | n.a. | n.a. |
| 46 | n.a. | n.a. | n.a. | n.a. | 0.951 | n.a. | n.a. |
| 274 | n.a. | n.a. | n.a. | n.a. | 1.170 | n.a. | n.a. |
| 275 | n.a. | n.a. | n.a. | n.a. | 3.012 | n.a. | n.a. |
| 276 | n.a. | n.a. | n.a. | n.a. | 1.804 | n.a. | n.a. | n.a.: not analyzed

Comparative Example 27

WO 2005/016528 discloses structurally closest compounds (2,6,9-trisubstituted purines), differing from the present invention in the substituents in position 9, aliphatic cyclopentyl in the place of aryl or heteroaryl. However, it was verified that compounds of the present invention are superior (see Table 5). The inventors tested the compound 264 of the present invention, and compounds 35 and 113 from document WO 2005/016528. The structures of the compounds tested are in the Scheme 6 below:

Scheme 6.

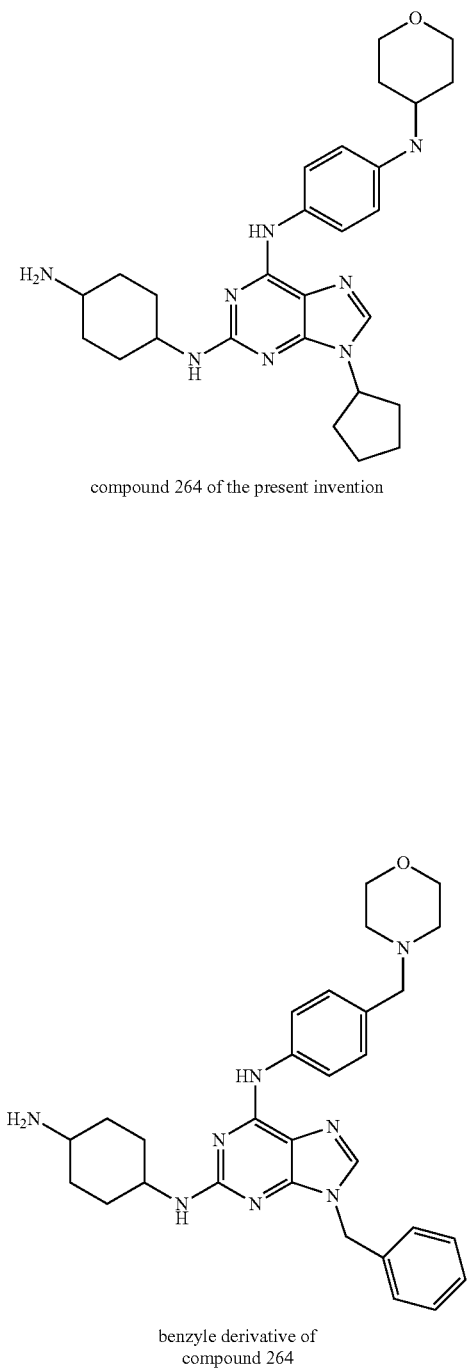

compound 264 of the present invention benzyle derivative of compound 264

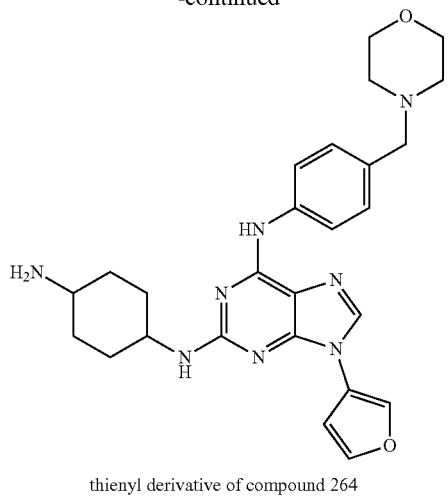

thienyl derivative of compound 264

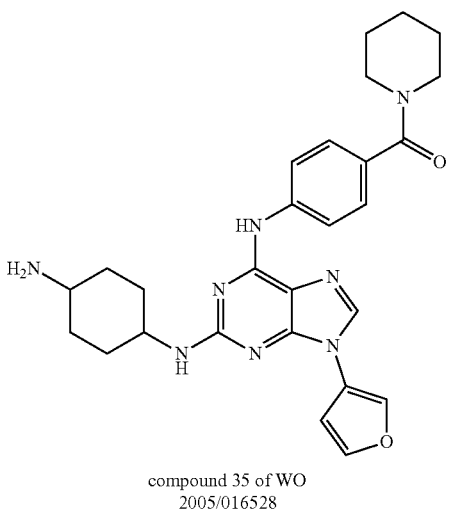

compound 35 of WO 2005/016528

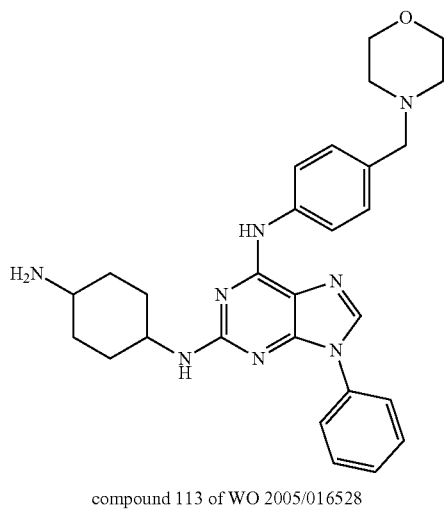

compound 113 of WO 2005/016528

The above compounds underwent tests according to Example 25 and Example 26. The results are resented in Tables 4 and 5:

TABLE 4

Influence of compounds on proliferation (72 h), $EC_{50}$ values (μM)

| | MV4-11 | MOLM-13 | EOL-1 | Kasumi-1 | THP-1 | U937 | K562 | MCF-7 | H1703 |
|---|---|---|---|---|---|---|---|---|---|
| Compound 264 (present invention) | 0.001 | 0.001 | 0.006 | 0.523 | 0.865 | 0.616 | 0.450 | 0.196 | 0.156 |
| Benzyl derivative of compound 264 (comparative) | 0.393 | 1.256 | 0.491 | n.a. | 14.767 | 2.621 | 2.690 | 4.835 | n.a. |
| Phenyl derivative of compound 264 (compound 113 of WO 2005/016528) | 0.648 | 0.912 | n.a. | 0.722 | n.a. | n.a. | 1.806 | n.a. | n.a. |
| 2-thienyl derivative of compound 264 (comparative) | 0.816 | 0.778 | n.a. | 0.758 | n.a. | n.a. | 0.742 | n.a. | n.a. |
| 2-thienyl derivative (compound 35 of WO 2005/016528) | 0.535 | 0.329 | n.a. | 1.208 | n.a. | n.a. | 1.474 | n.a. | n.a. | n.a.: not analyzed

TABLE 5

| | Influence of compounds on protein kinase inhibition, $IC_{50}$ values (μM) | |
|---|---|---|
| | FLT3 ITD | CDK2 |
| Compound 264 (present invention) | 0.001 | 0.007 |
| Benzyl derivative of compound 264 (comparative) | 1.027 | 7.510 |
| Phenyl derivative of compound 264 (compound 113 of WO 2005/016528) | 0.759 | >5 |
| 2-thienyl derivative of compound 264 (comparative) | 0.811 | >5 |
| 2-thienyl derivative (compound 35 of WO 2005/016528) | 0.637 | >5 |

The results in Tables 4 and 5 show indirect comparison that aromatic substituents (aryl, heteroaryl, arylalkyl) in position 9 have similar impact on inhibition activity on protein kinases. The substitution of aromatic substituent by aliphatic cycle increases the antiproliferative effect of the resulting compound by 2 orders of magnitude, similar improvement was observed in protein kinase inhibition.

Example 28 Kinase Selectivity of Novel Compound 264

Kinase-inhibitory properties of compound 264 were screened at single concentration of 10 nM in biochemical phosphorylation assays against other kinases (Table 6) in Carna Biosciences.

Compound 264 displayed strong inhibitory activity especially against FLT3, PDGFRα/β, significant inhibition has been measured also with TRK, CAMK2, SIK, YES, FMS, KIT (D816V), MNK2, ACK and SRC.

TABLE 6

Kinase selectivity of novel compound 264

| kinases | inhibition of kinase activity at 10 nM compound 264 |
|---|---|
| PDGFRβ, FLT3, CLK1, TRKA, TRKC, QIK, TRKB, CaMK2δ, SIK, PDGFRα, YES, FMS, CAMK2γ, KIT (D816V), MNK2, ACK, SRC, PDGFRα(V561D) | 100-90% |
| DDR1, DDR2, LCK, PDGFRα(D842V), PHKG1, MER, MNK1, ITK, CaMK2α, MUSK, SLK, FLT4, LYNb, FYN (isoform b), CLK2, LOK, LYNa, ALK (L1196M), FGR, FYN (isoform a), FLT1, CDK2/CycA2, DYRK1B, MAP4K2, HCK, MARK4, KDR, CDK5/p25, FRK, ALK (F1174L), KIT, MST1 | 89-60% |
| CDK9/CycT1, CDK2/CycE1, EPHB1, MARK3, AXL, SRPK2, ALK, IRR, MARK1, ABL, ARG, CDK7/CycH/MAT1, CAMK2β, NPM1-ALK, NuaK1, FGFR2, CDK4/CycD3, BLK, KIT (D816E), DYRK1A, PAK5, FGFR1, JAK3, HER4, MARK2, TSSK1, AMPKα2/β1/γ1, PHKG2, EML4-ALK, TEC, ALK (R1275Q), RET (S891A), IRAK4, FGFR1 (V561M) | 59-40% |
| IRAK1, EPHA1, TXK, PKN1, HGK, FGFR3, ABL (E255K), FES, LTK, TNK1, EGFR (d746-750), KIT (V560G), MLK3, EPHB4, CRIK, FER, CK1δ, NuaK2, PDGFRα(T674I), PIK3CA/PIK3R1, SYK, MLK1, TYRO3, MAP3K3, HIPK4, FGFR3 (K650E), EGFR (L858R), | <40% |

TABLE 6-continued

Kinase selectivity of novel compound 264

| kinases | inhibition of kinase activity at 10 nM compound 264 |
|---|---|
| TNIK, PAK4, CHK1, CK1α, YES (T348I), FGFR3 (K650M), PKD2, INSR, CDC2/CycB1, PKD3, PKCζ, KIT(V654A), AMPKα1/β1/γ1, PKCι, RET, CDK3/CycE1, PYK2, EPHA8, ABL (T315I), EPHB2, AurB, BTK, BMX, RET (M918T), NDR2, PKD1, RET (G691S), SRPK1, ROS, NDR1, FAK, JAK2, MELK, EGFR (L861Q), DCAMKL2, MST3, CLK3, RSK4, RSK3, EGFR, RSK2, MST4, IGF1R, MST2, EPHA4, CK1ε, Haspin, P70S6K, PAK6, LATS2, EPHA2, RET (Y791F), MOS, JNK1, PKCδ, IKKα, BRAF, PKCε, RSK1, CSK, CDK6/CycD3, PRKX, MINK, PKR, COT, ROCK1, FGFR4 (V550L), EPHA5, HIPK2, PKACβ, PKCθ, TBK1, NEK2, PKACα, skMLCK, CaMK1δ, FGFR4(V550E), MET(Y1235D), HIPK3, ROCK2, RON, EPHB3, BRK, MAP3K5, AurA/TPX2, MAP3K2, PLK2, BRSK1, JAK1, AurC, MAP2K6, FGFR4, MLK2, KIT (T670I), TYK2, PIM1, MRCKβ, AKT2, CK1γ1, KIPK1, PEK, DYRK2, CGK2, MET, SPHK2, MAP2K7, CaMK1α, NEK9, CHK2, MAP3K4, IKKε, EPHA3, DLK, TAOK2, MET (M1250T), SGK, PLK3, MAPKAPK5, DYRK3, MAP2K4, MGC42105, PKCα, NEK1, PAK1, PGK, AurA, EPHA7, Erk2, PKCβ2, SRM, MSSK1, JNK2, PKCγ, CK1γ3, SGK3, CaMK4, CK1γ2, PBK, TIE2, Erk5, DAPK1, MRCKα, PKACγ, MAP3K1, BRSK2, p70S6Kβ, PKCη, MET(D1228H), GSK3β, JNK3, EGFR(T790M/L858R), TSSK2, p38β, p38γ, WNK1, PKCβ1, TSSK3, PLK1, WNK2, RAF1, NEK6, NEK4, p38α, MSK1, CDC7/ASK, MSK2, PIM2, WNK3, EGFR(T790M), BRAF(V600E), MAP2K5, MAP2K1, PDHK2, EEF2K, TAK1-TAB1, MAPKAPK2, SPHK1, EPHA6, PIM3, p38δ, CK2α2/β, EGFR(d746-750/T790M), GSK3α, NEK7, PDK1, HER2, AKT3, IKKβ, MAPKAPK3, CK2α1/β, PDHK4, MAP2K2, PASK, MAP2K3, SGK2, AKT1, PAK2, Erk1 | |

Example 29 Compounds Inhibits Phosphorylation of FLT3 and PDGFRA and Affects their Downstream Signaling Pathways In Vitro To confirm kinase-inhibitory activity of novel compounds in cells, MV4-11 cells with FLT3-ITD and EOL-1 cells expressing FIP1L1-PDGFRA fusion protein were analyzed upon 1 hour treatment. Treated cells were harvested by centrifugation and homogenized in an extraction buffer (10 mM HEPES pH 7.4, 1 mM EDTA, 1 mM EGTA, 5 mM KC, 1.5 mM $MgCl_2$, 0.5% NP40, supplemented with 1 mM DTT, 1 mM NaF, 0.1 mM $Na_3VO_4$, 1 mM PMSF, 0.5 µg/ml Leupeptin, 2 µg/ml Aprotinin) on ice for 25 ml. The homogenates were clarified by centrifugation at 10,000 g for 30 min at 4° C., proteins were quantified by the Bradford method and then diluted to the same concentration. 30 g of total proteins were separated by SDS-polyacrylamide gel electrophoresis and transferred onto nitrocellulose membranes. Membranes were blocked in 5% BSA in TBS with 0.1% Tween 20 and probed overnight with specific antibodies for FLT3 (clone 8F2), phospho-FLT3 Y589/591 (30D4), phospho-FLT3 Y591 (33G6), phospho-FLT3 Y842 (10A8), phospho-FLT3 Y969 (C24D9), PDGFRA (D1E1E), phospho-PDGFRA Y849/PDGFRB Y857 (C43E9), phospho-PDGFRA Y1018, p44/42 MAPK (ERK1/2), phospho-p44/42 MAPK (ERK1/2) (Thr202/Tyr204), STAT5, Phospho-STAT5(Tyr694), STAT3 (79D7), phospho-STAT3 (Tyr705) (D3A7), MEK1/2 (D1A5), phospho-MEK1/2 (Ser217/221) purchased from Cell Signaling, USA, α-tubulin (DM1A, Sigma Aldrich, USA) and PCNA (PC-10, gifted by Dr. B. Vojtesek). All primary antibodies were diluted in 5% BSA in TBS with 0.1% Tween 20. Horseradish peroxidase conjugated anti-mouse IgG or anti-rabbit IgG (Cell Signaling, USA) were used as the secondary antibodies and were visualised with ECL reagents (Thermo Scientific, USA).

Figure 2:
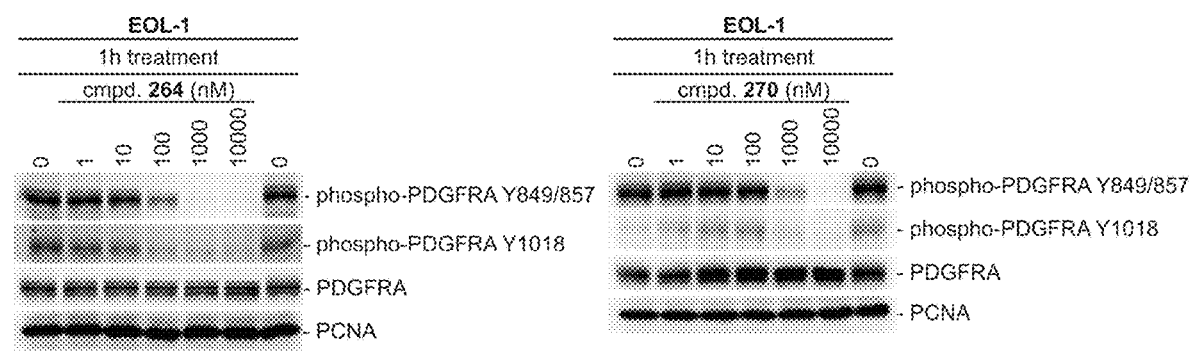
FIG. 2 shows immunoblotting analysis of PDGFR phosphorylation in EOL-1 cells treated with compounds 264 and 270. Cells were exposed for 1 hour to the indicated concentrations of 264 or 270 and then levels of phosphorylations at specific tyrosine residues of PDGFR were analyzed.

Immunoblotting analysis of MV4-11 FLT3-ITD cells treated with novel compounds revealed strong inhibition of phosphorylation of several tyrosine residues of FLT3 receptor kinase (including Y589, Y591, Y742) in low nanomolar concentrations. FIG. 1 shows an example of cellular FLT3 dephosphorylation by various doses of compounds 264 and 270. Compounds 264 and 270 also potently reduced phosphorylation of several tyrosine residues of PDGFRA in EOL-1 cells (FIG. 2).

Figure 3:
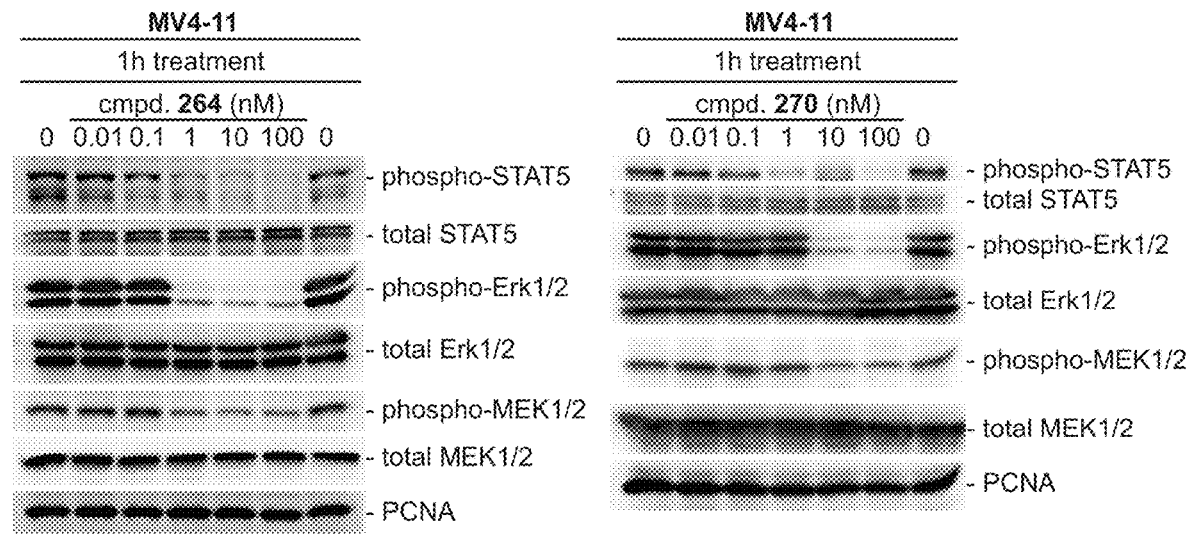
FIG. 3 shows immunoblotting analysis of proteins involved in signaling pathways downstream of FLT3 in MV4-11 cells treated with compounds 264 and 270 for 1 hour.
Figure 4:
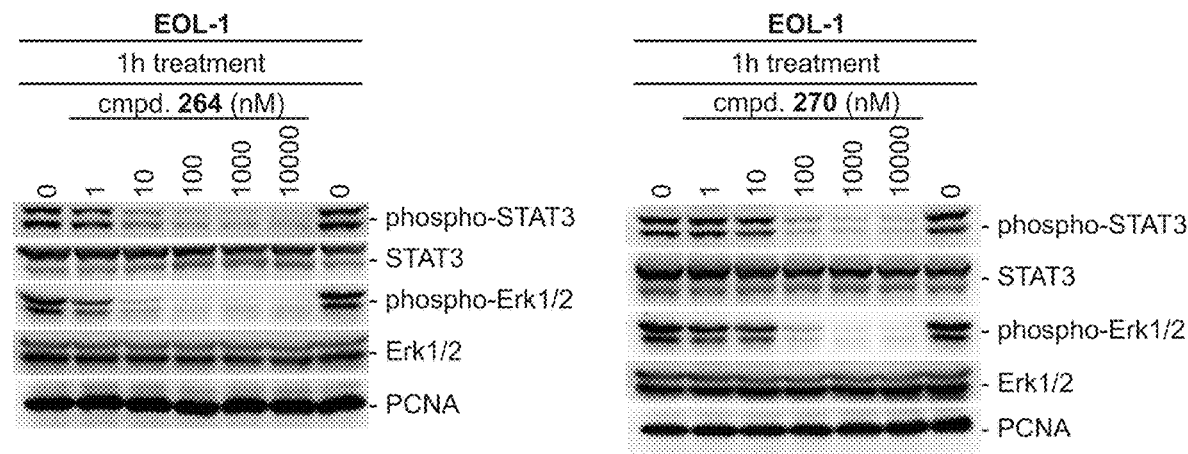
FIG. 4 shows immunoblotting analysis of proteins involved in signaling pathways downstream of PDGFR in EOL-1 cells treated with compounds 264 and 270 for 1 hour.

Novel compounds are able not only to deactivate FLT3 or PDGFR receptors in cells, but also block downstream signaling pathways. Additional analyses confirmed that compounds 264 and 270 reduced phosphorylation of ERK1/2, STAT5 and STAT3, which are involved in downstream signaling pathways of FLT3 and PDGFR in MV4-11 and EOL-1 cells, respectively (FIG. 3, 4).

Example 30 Novel Compounds Induce Caspase-Dependent Apoptosis

Measurement of proapoptotic properties of new compounds was based on quantification of enzymatic activities of caspases-3/7. Activity of cellular caspase-3/7 was measured according to Carrasco et al., 2003, BioTechniques, 34(5): 1064-67. Briefly, MV4-11 and K562 cells were incubated in the densities of 50000 or 20000 cells/well, respectively, in 96-well plates overnight. Next day, the compounds in appropriate concentrations were added and cells were incubated for the 24 hours. After incubation, 3× caspase-3/7 assay buffer (150 mM HEPES pH 7.4, 450 mM NaCl, 150 mM KCl, 30 mM MgCl2, 1.2 mM EGTA, 1.5% Nonidet P40, 0.3% CHAPS, 30% sucrose, 30 mM DTT, 3 mM PMSF) with 150 µM Ac-DEVD-AMC as a substrate (Sigma-Aldrich) was added to the wells and plates were incubated at 37° C. at room temperature. The caspase-3/7 activity was measured after 4 hours using Fluoroskan Ascent microplate reader (Labsystems) at 346 nm/442 nm (ex/em).

Figure 5:
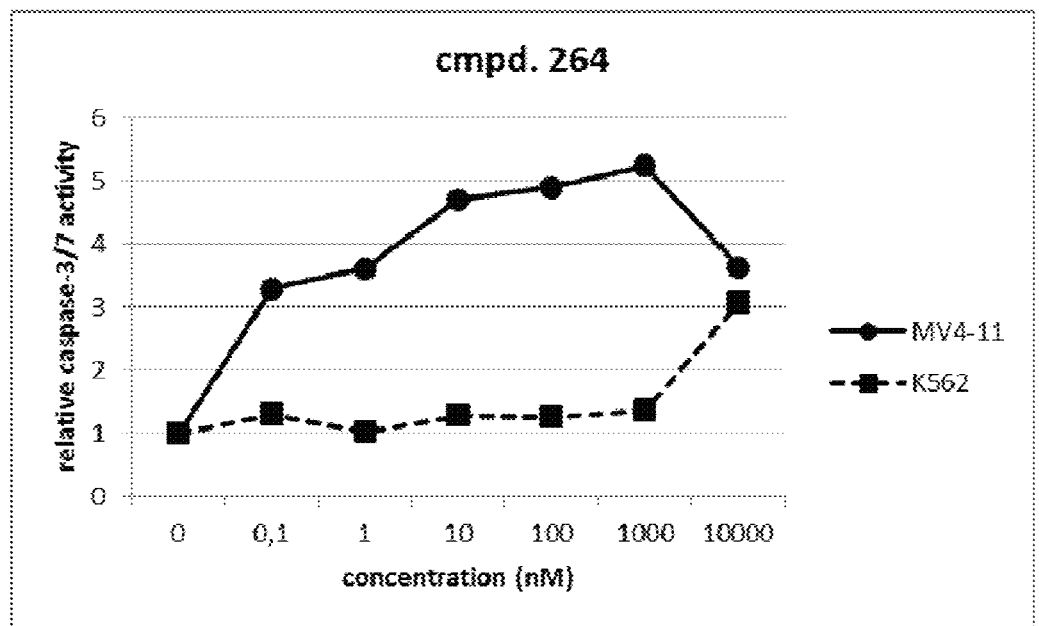
FIG. 5 shows relative caspase-3/7 activity in MV4-11 and K562 cells after treatment with compound 264.

A fluorimetry-based caspase-3/7 activity assay in MV4-11 and K562 cells treated with all novel compounds revealed potent activation of the caspases even in subnanomolar concentration in FLT3-ITD positive MV4-11 cells, while activation of caspases in K562 cells was induced in micromolar concentrations. FIG. 5 shows an example of caspase activity in cells treated with different doses of compound 264.

Figure 6:
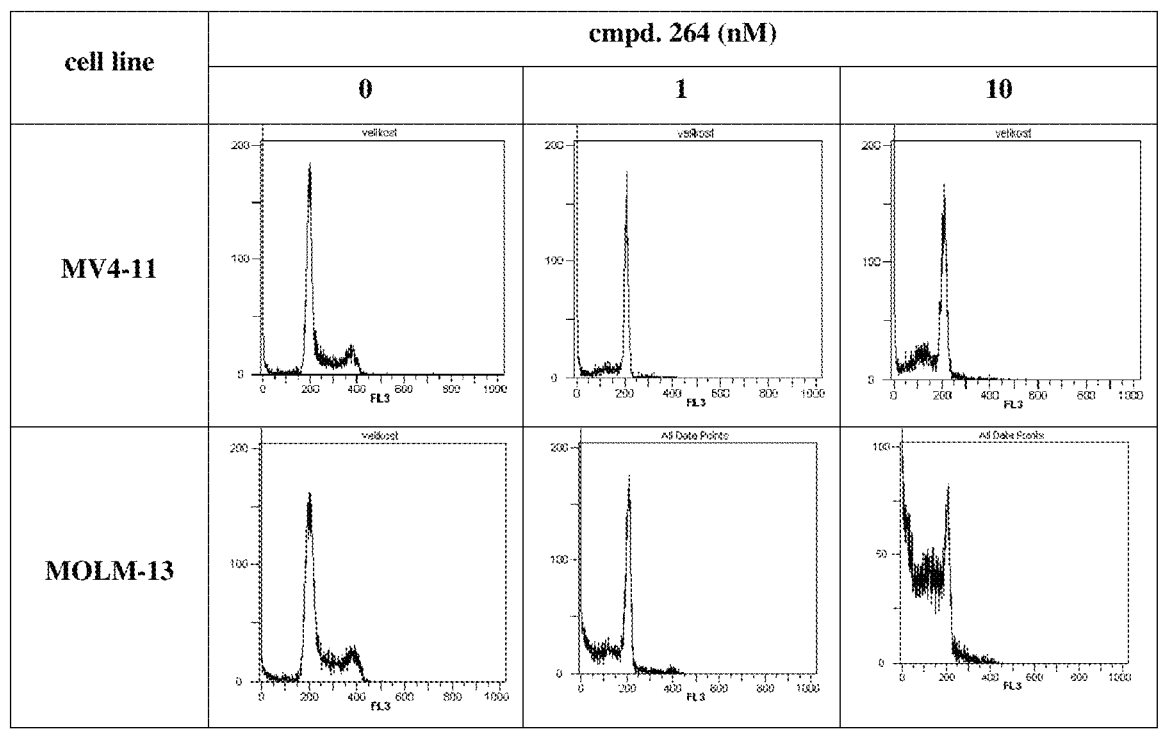
FIG. 6 shows flow cytometric analysis of cell cycle of MV4-11 and MOLM-13 cells treated with compound 264.

Example 31 Novel Compounds Induce G1 Arrest of the Cell Cycle and Activate Apoptosis MV4-11 and MOLM-13 cells (FLT3-ITD positive) treated with novel compounds for 24 hours were harvested by centrifugation and fixed with 70% ice-cold ethanol. Upon staining with propidium iodide (final concentration 10 µg/ml; Sigma-Aldrich, USA), the relative DNA content was measured by flow cytometer Cell Lab Quanta SC (Beckman Coulter, USA). Novel compounds induced massive G1 arrest of the cell cycle in both cell lines even in the concentration as low as 1 nM. Higher concentrations increased the number of cells in the sub-G1 population corresponding to the apoptotic cells. An example of the cell cycle profile of cells treated with compound 264 is shown in FIG. 6.

Example 32 Combination of Novel Compounds with Other Anticancer Drugs

Measurements of proapoptotic properties of new compounds in combinations with other anticancer drugs were based on quantification of enzymatic activities of caspases-3/7. Activity of caspase-3/7 was measured as described (Carrasco et al; BioTechniques. 2003, 34: 1064-67). Briefly, MV4-11 cells were incubated in the densities of 50000 cells/well in 96-well plates overnight. Next day, the compounds' combinations in appropriate concentrations were added and cells were incubated for 24 hours. After incubation, 3× caspase-3/7 assay buffer (150 mM HEPES pH 7.4, 450 mM NaCl, 150 mM KCl, 30 mM $MgCl_2$, 1.2 mM EGTA, 1.5% Nonidet P40, 0.3% CHAPS, 30% sucrose, 30 mM DTT, 3 mM PMSF) with 150 µM Ac-DEVD-AMC as a substrate was added to the wells and plates were incubated at 37° C. at room temperature. The caspase-3/7 activity was measured after 4 hours using Fluoroskan Ascent microplate reader (Labsystems) at 346 nm/442 nm (excitation/emission). An activity assay revealed potentiation of proapoptotic effect of novel compounds by other anticancer drugs (Table 7).

TABLE 7

Relative caspase-3/7 activity in MV4-11 cells after treatment with compound 264 combined with other drugs.

| compound combination | relative caspase activity concentration (nM) | | | |
| --- | --- | --- | --- | --- |
|  | 0 | 1 | 10 | 100 |
| 264 | 1.00 | — | 3.51 | 6.32 |
| 264 + cytarabine (500 nM) | 1.69 | 1.88 | 5.72 | >10 |
| 264 + daunorubicin (100 nM) | 1.31 | 2.16 | 6.21 | >10 |
| 264 + topotecan (50 nM) | 1.15 | 1.70 | 3.70 | 8.55 |
| 264 + paclitaxel (100 nM) | 1.27 | 2.79 | 5.67 | >10 |
| 264 + pictilisib (100 nM) | 1.00 | 0.95 | 6.28 | >10 |
| 264 + tofacitinib (100 nM) | 1.00 | — | 6.57 | >10 |

Example 33 Activity of Novel Compound 264 In Vivo

Female athymic nu/nu mice (8 weeks old) were subcutaneously implanted with $5×10^6$ MV4-11 cells in 1:1 mixture with Matrigel (High concentration basement membrane Matrigel, Corning) into the hind flank on day 0. Tumors were allowed to growth to the volume of 500-800 $mm^3$. Body weight and tumor size were recorded 3 times a week. Mice were randomized to treatment groups, 4 to 5 mice each, for target modulation studies.

A single-dose of novel compound 264 (10 mg/kg, formulated in acidified saline) or Quizartinib (10 mg/kg, formulated in 5% hydroxypropyl-β-cyclodextrin) was administered by intraperitoneal injection or oral gavage, respectively. Mice were sacrificed at 2 time points (2 hours and 24 hours) after treatment. Tumors were resected and mechanically disintegrated. Cells were washed twice with PBS (lx), then lysed in ice-cold lysis buffer (10 mM HEPES pH 7.4, 1 mM EDTA, 1 mM EGTA, 5 mM KCl, 1.5 mM $MgCl_2$) supplemented with protease and phosphatase inhibitors (10 mM β-glycerolphosphate; 1 mM NaF; 0.1 mM $Na_3VO_4$; 0.1 mM PMSF; 10 µg/ml Leupeptin; 2 µg/ml Aprotinin; 1 mM DTT) and cleared by centrifugation. Samples (50 µg of total protein amount) were separated on SDS-PAGE, followed by transfer of the separated proteins to nitrocellulose membrane. The effect of compound 264 on phosphorylation status of FLT3 kinase was compared with Quizartinib, which was previously described as FLT3 specific inhibitor.

Figure 7:
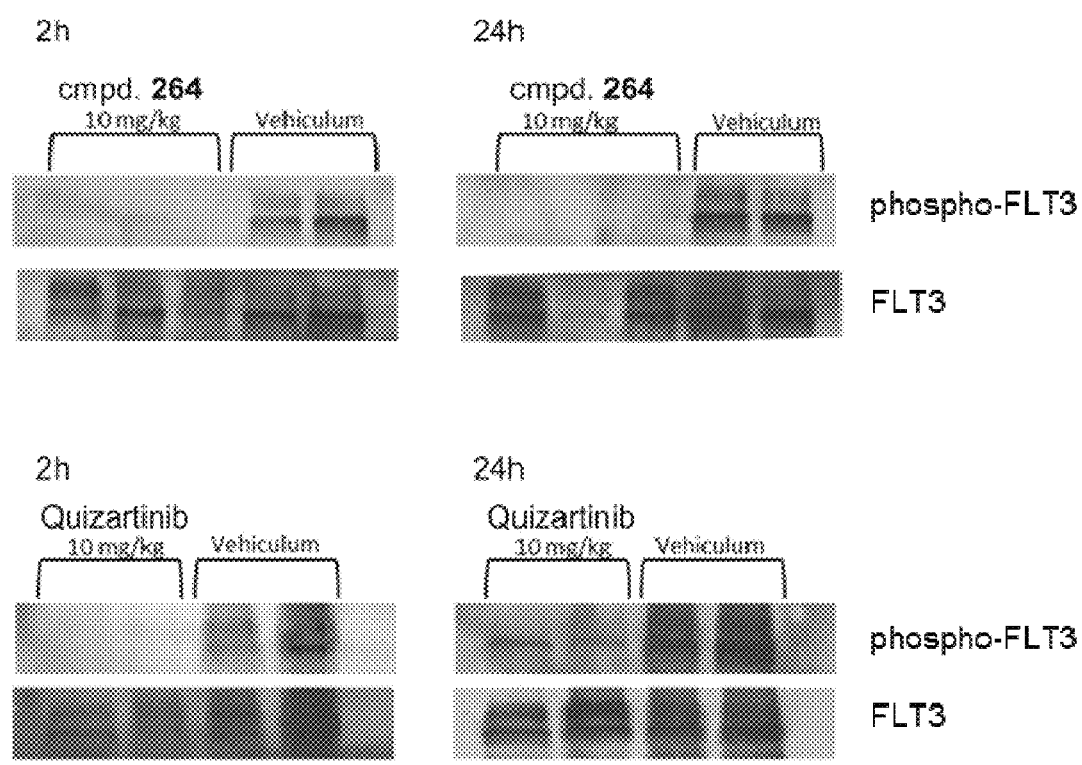
FIG. 7 shows immunoblotting analysis of FLT3 phosphorylation in MV4-11 xenograft treated with compound 264 or Quizartinib. Each lane represents a separate animal.

Quantification of pFLT3 revealed that the kinase was inhibited by 95% as early as 2 hours after administration of compound 264 and the inhibition sustained 24 hours, in contrast to elevated level of pFLT3 24 hours after Quizartinib administration (FIG. 7); the Quizartinib data are in agreement with published results (Zarrinkar et al., Blood 114 (14): 2984-92). The inhibitory effect was obvious also from analysis of phosphorylation of STAT5. Compound 264 reduced the pSTAT5 level by more than 95% after 24 hours, slightly more effectively than quizartinib.

Example 34 Dry Capsules 5000 capsules, each of which contains 0.25 g of a compound of the formula I as an active ingredient, are prepared as follows:

Composition

| Active ingredient | 1250 g |
| --- | --- |
| Talc | 180 g |
| Wheat starch | 120 g |
| Magnesium stearate | 80 g |
| Lactose | 20 g |

Preparation process: The powdered substances mentioned are pressed through a sieve of mesh width 0.6 mm. Portions of 0.33 g of the mixture are transferred to gelatine capsules with the aid of a capsule-filling machine.

Example 35 Soft Capsules 5000 soft gelatine capsules, each of which contains 0.05 g of a compound of the formula I as an active ingredient, are prepared as follows:

Composition

| Active ingredient | 250 g |
|---|---|
| Lauroglykol | 2 litres |

Preparation process: The powdered active ingredient is suspended in Lauroglykol® (propylene glycol laurate, Gattefossé S. A., Saint Priest, France) and ground in a wet-pulveriser to a particle size of about 1 to 3 µm. Portions of in each case 0.419 g of the mixture are then transferred to soft gelatine capsules by means of a capsule-filling machine.

Example 36 Soft Capsules 5000 soft gelatine capsules, each of which contains 0.05 g of a compound of the formula I as an active ingredient, are prepared as follows:

Composition

| Active ingredient | 250 g |
|---|---|
| PEG 400 | 1 litre |
| Tween 80 | 1 litre |

Preparation process: The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 µm. Portions of in each case 0.43 g of the mixture are then transferred to soft gelatine capsules by means of a capsule-filling machine.

The invention claimed is:

1. 2,6-disubstituted-9-cyclopentyl-9H-purines of the general formula I

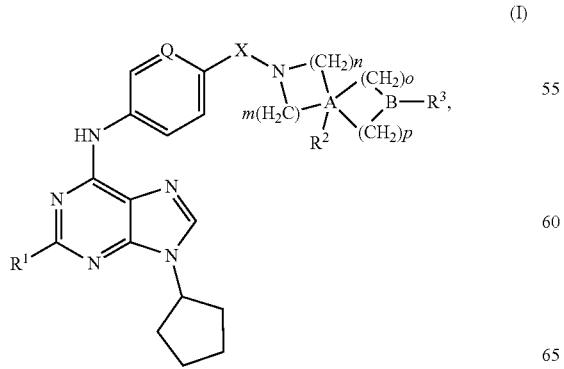

(I)

wherein $R^1$ is selected from the group consisting of:

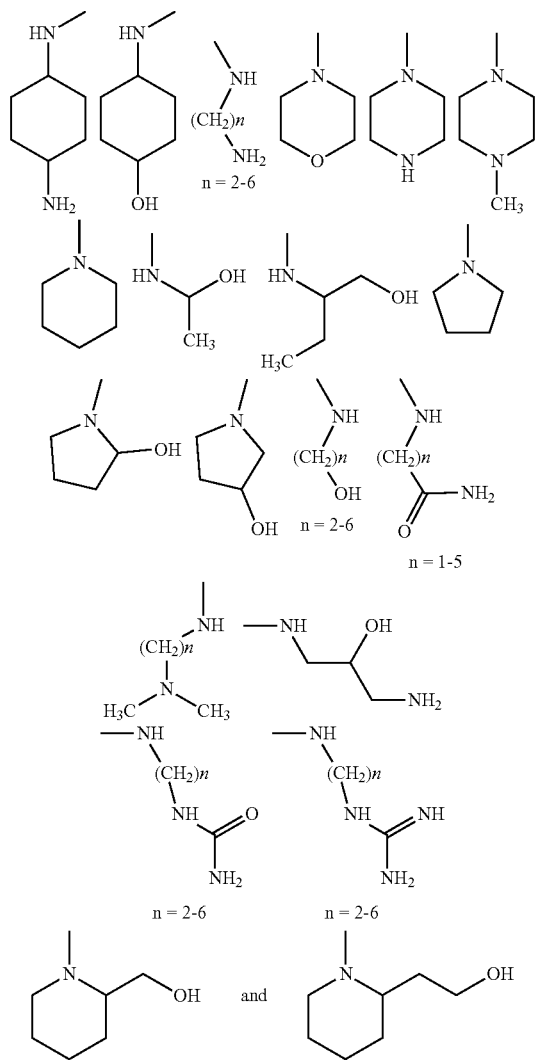

and

Q is =CH— or =N—;

X is $CH_2$, NH or C=O;

m is 1 or 2 or 3;

n is 1 or 2 or 3;

A is selected from the group consisting of O, N, CH, and C; with the proviso that:

if A is O, then o=p=0 and $R^2$, B and $R^3$ are not present, if A is N or CH, then $R^2$ is selected from H, $CH_3$, and $CH_2CH_3$, and o=p=0 and B and $R^1$ are not present, if A is C, then $R^2$ is not present, o is 1 or 2 or 3, p is 1 or 2 or 3, and B and $R^3$ are as defined below;

B is selected from O and N, with the proviso that:

if B is O, then $R^3$ is not present, if B is N, then $R^3$ is selected from H, $CH_3$, and $CH_2CH_3$; and pharmaceutically acceptable salts thereof.

2. 2,6-disubstituted-9-cyclopentyl-9H-purines of the general formula I,

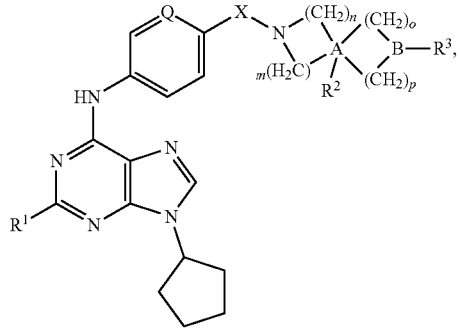

(I)

wherein R¹ is selected from the group consisting of:

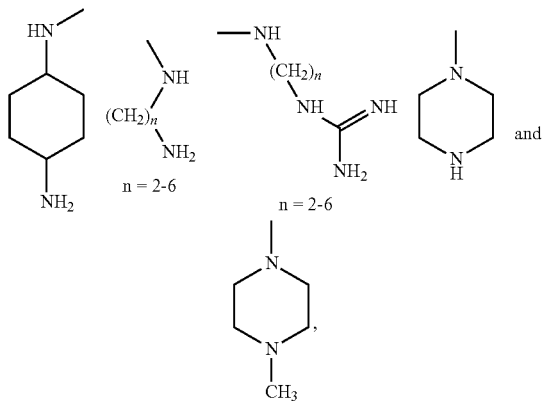

and

Q is =CH— or =N—;
X is $CH_2$, NH or C=O;
m is 1 or 2 or 3;
n is 1 or 2 or 3;
A is selected from the group consisting of O, N, CH, and C; with the proviso that:
  if A is O, then o=p=0 and R², B and R³ are not present,
  if A is N or CH, then R² is selected from H, $CH_3$, and $CH_2CH_3$, and o=p=0 and B and R³ are not present,
  if A is C, then R² is not present, o is 1 or 2 or 3, p is 1 or 2 or 3, and B and R³ are as defined below;
B is selected from O and N, with the proviso that:
  if B is O then R¹ is not present,
  if B is N, then R³ is selected from H, $CH_3$, and $CH_2CH_3$; and
pharmaceutically acceptable salts thereof.

3. 2,6-disubstituted-9-cyclopentyl-9H-purines of the general formula I according to claim 1, wherein A is O.

4. 2,6-disubstituted-9-cyclopentyl-9H-purines of the general formula I according to claim 1, wherein X is $CH_2$.

5. 2,6-disubstituted-9-cyclopentyl-9H-purines of the general formula I according to claim 1, wherein m and/or n and/or o and/or p are 1 or 2, wherein m and n are both identical and/or o and p are both identical.

6. 2,6-disubstituted-9-cyclopentyl-9H-purines of the general formula I according to claim 1, wherein A is C; m, n, o and p are 1; and B is O or N.

7. 2,6-disubstituted-9-cyclopentyl-9H-purines of the general formula I according to claim 1, wherein the entity of the general formula (II)

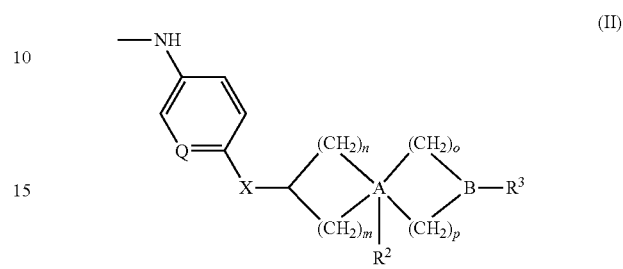

(II)

is selected from the following substituents:
4-morpholin-4-ylmethyl-phenylamino, 4-piperazin-1-ylmethyl-phenylamino, 4-(4-methyl-piperazin-1-ylmethyl)-phenylamino, 4-(4-ethyl-piperazin-1-ylmethyl)-phenylamino, 4-(2-oxa-6-aza-spiro[3.3]hept-6-ylmethyl)-phenylamino, 4-(2,6-diaza-spiro[3.3]hept-2-ylmethyl)-phenylamino, 4-(6-methyl-2,6-diaza-spiro[3.3]hept-2-ylmethyl)-phenylamino, 4-(6-ethyl-2,6-diaza-spiro[3.3]hept-2-ylmethyl)-phenylamino, 4-morpholin-4-ylcarbonyl-phenylamino, 4-piperazin-1-ylcarbonyl-phenylamino, 4-(4-methyl-piperazin-1-ylcarbonyl)-phenylamino, 4-(4-ethyl-piperazin-1-ylcarbonyl)-phenylamino, 4-(2-oxa-6-aza-spiro[3.3]hept-6-ylcarbonyl)-phenylamino, 4-(2,6-diaza-spiro[3.3]hept-2-ylcarbonyl)-phenylamino, 4-(6-methyl-2,6-diaza-spiro[3.3]hept-2-ylcarbonyl)-phenylamino, 4-(6-ethyl-2,6-diaza-spiro[3.3]hept-2-ylcarbonyl)-phenylimino, 6-morpholin-4-ylmethyl-pyridin-3-ylamino, 6-piperazin-1-ylmethyl-pyridin-3-ylamino, 6-(4-methyl-piperazin-1-ylmethyl)-pyridin-3-ylamino, 6-(4-ethyl-piperazin-1-ylmethyl)-pyridin-3-ylamino, 6-(2-oxa-6-aza-spiro[3.3]hept-6-ylmethyl)-pyridin-3-ylamino, 6-(2,6-diaza-spiro[3.3]hept-2-ylmethyl)-pyridin-3-ylamino, 6-(6-methyl-2,6-diaza-spiro[3.3]hept-2-ylmethyl)-pyridin-3-ylamino, 6-(6-ethyl-2,6-diaza-spiro[3.3]hept-2-ylmethyl)-pyridin-3-ylamino, 6-morpholin-4-ylcarbonyl-pyridin-2-ylamino, 6-piperazin-1-ylcarbonyl-pyridin-2-ylamino, 6-(4-methyl-piperazin-1-ylcarbonyl)-pyridin-2-ylamino, 6-(4-ethyl-piperazin-1-ylcarbonyl)-pyridin-2-ylamino, 6-(2-oxa-6-aza-spiro[3.3]hept-6-ylcarbonyl)-pyridin-2-ylamino, 6-(2,6-diaza-spiro[3.3]hept-2-ylcarbonyl)-pyridin-2-ylamino, 6-(6-methyl-2,6-diaza-spiro[3.3]hept-2-ylcarbonyl)-pyridin-2-ylamino, and 6-(6-ethyl-2,6-diaza-spiro[3.3]hept-2-ylcarbonyl)-pyridin-2-ylamino.

8. A pharmaceutical composition comprising at least one 2,6-disubstituted-9-cyclopentyl-9H-purine according to claim 1, optionally in combination with at least one antitumor agent selected from the group consisting of cytosine arabinoside, daunorubicin, doxorubicin, cyclophosphamide, etoposide, carboplatin, fludarabine, mitoxantrone, dexamethasone, rituximab, midostaurin, GCS factor, decitabine, azacitidine, paclitaxel, gemcitabine, motesanib and panitumumab, and further comprising at least one pharmaceutically acceptable carrier.

* * * * *